(12) United States Patent
Roth

(10) Patent No.: US 7,933,027 B1
(45) Date of Patent: *Apr. 26, 2011

(54) PROCESSING WAVEFORM-BASED NDE

(75) Inventor: Donald J Roth, Rocky River, OH (US)

(73) Assignee: The United States of America as represented by the Administrator of National Aeronautics and Space Administration, Washington, DC (US)

( * ) Notice: Subject to any disclaimer, the term of this patent is extended or adjusted under 35 U.S.C. 154(b) by 180 days.

This patent is subject to a terminal disclaimer.

(21) Appl. No.: 12/326,436

(22) Filed: Dec. 2, 2008

Related U.S. Application Data

(63) Continuation-in-part of application No. 12/163,382, filed on Jun. 27, 2008, now Pat. No. 7,876,423.

(51) Int. Cl.
*G01N 21/00* (2006.01)
*G01B 11/28* (2006.01)

(52) U.S. Cl. .......................... 356/630; 356/27

(58) Field of Classification Search .................. 356/497, 356/502, 630–636, 27; 73/655, 629, 622, 73/597, 593
See application file for complete search history.

(56) References Cited

U.S. PATENT DOCUMENTS

| | | | | |
|---|---|---|---|---|
| 4,056,970 | A | * | 11/1977 | Sollish .............................. 73/629 |
| 4,533,829 | A | | 8/1985 | Miceli et al. |
| 4,563,898 | A | * | 1/1986 | Kanda et al. ....................... 73/606 |
| 5,307,680 | A | * | 5/1994 | Drescher-Krasicka ......... 73/606 |
| 5,549,003 | A | * | 8/1996 | Drescher-Krasicka ......... 73/606 |
| 5,623,145 | A | | 4/1997 | Nuss |
| 5,710,430 | A | | 1/1998 | Nuss |
| 5,883,720 | A | * | 3/1999 | Akiyama et al. ............... 356/632 |
| 5,939,721 | A | | 8/1999 | Jacobsen et al. |
| 5,974,886 | A | * | 11/1999 | Carroll et al. .................... 73/598 |
| 6,495,833 | B1 | | 12/2002 | Alfano et al. |
| 6,810,742 | B2 | * | 11/2004 | Sauerland ........................ 73/597 |
| 6,828,558 | B1 | | 12/2004 | Arnone et al. |
| 6,849,852 | B2 | | 2/2005 | Williamson |
| 6,853,926 | B2 | | 2/2005 | Alfano et al. |
| 7,038,208 | B2 | | 5/2006 | Alfano et al. |
| 7,119,339 | B2 | | 10/2006 | Ferguson et al. |

(Continued)

OTHER PUBLICATIONS

Roth, D.J., Seebo, J.P., and Winfree, W.P. "Simultaneous Non-Contact Precision Measurement of Microstructural and Thickness Variation in Dielectric Materials Using Terahertz Energy" NASA TM-2008-2148997, Mar. 2008, 2008-214997, pp. 1-18, NASA STI, http://www.sti.nasa.gov, NASA Center for AeroSpace Information (CASI) 7115 Standard Drive, Hanover, MD 21076-1320. http://gltrs.grc.nasa.gov.

(Continued)

*Primary Examiner* — Sang Nguyen
(74) *Attorney, Agent, or Firm* — Robert H. Earp, III; Woodling, Krost & Rust

(57) ABSTRACT

A computer implemented process for simultaneously measuring the velocity of terahertz electromagnetic radiation in a dielectric material sample without prior knowledge of the thickness of the sample and for measuring the thickness of a material sample using terahertz electromagnetic radiation in a material sample without prior knowledge of the velocity of the terahertz electromagnetic radiation in the sample is disclosed and claimed. Utilizing interactive software the process evaluates, in a plurality of locations, the sample for microstructural variations and for thickness variations and maps the microstructural and thickness variations by location. A thin sheet of dielectric material may be used on top of the sample to create a dielectric mismatch. The approximate focal point of the radiation source (transceiver) is initially determined for good measurements.

19 Claims, 32 Drawing Sheets

U.S. PATENT DOCUMENTS

| | | | |
|---|---|---|---|
| 7,145,148 | B2 | 12/2006 | Alfano et al. |
| 7,174,037 | B2 | 2/2007 | Arnone et al. |
| 7,214,940 | B2 | 5/2007 | Cluff et al. |
| 2004/0026622 | A1 | 2/2004 | DiMarzio et al. |
| 2004/0095147 | A1 | 5/2004 | Cole |
| 2004/0113103 | A1 | 6/2004 | Zhikov |
| 2007/0090294 | A1 | 4/2007 | Safai et al. |
| 2007/0145276 | A1 | 6/2007 | Zhang et al. |
| 2007/0228280 | A1 | 10/2007 | Mueller |
| 2007/0235658 | A1 | 10/2007 | Zimdars et al. |

OTHER PUBLICATIONS

Columbia Accident Investigation Board (CAIB) Report, vol. 1, Aug. 2003, pp. 1-248.

Generazio, E.R., Roth, D.J., and Stang, D.B.: "Ultrasonic Imaging of Porosity Variations Produced During Sintering" J.Am. Ceram. Soc. vol. 72, No. 7, pp. 1282-1285 1989.

Hu, B.B. and Nuss, M.C., "Imaging with Terahertz Waves," Optics Letters, vol. 20, No. 16, p. 1716-1719, May 11, 1995, Optical Society of America.

Hsu. D.K. et al.: "Simultaneous determination of ultrasonic velocity, plate thickness, and wedge angle using one-sided contact measurements". NDT&E International 1994 vol. 27, No. 2, pp. 75-82, Butterworth-Heinemann Ltd.

Hull. D.R.; Kautz, H.E.; and Vary. A.: "Measurement of Ultrasonic Velocity Using Phase Slope and Cross-Correlation Methods", Materials, Evaluation. vol. 43,. No. 11, 1985, pp. 1455-1460. Presented at the 1984 ASNT Spring Conference, May 1984, Denver, CO.

Mittleman, D.M., Jacobsen, R.H., and Nuss, M.C., "T-ray imaging," J.Sel.Top. Quant. Elec., vol. 2, No. 3 p. 679-692 Sep. 1996, IEEE.

Mittleman, D.M., Gupta, M., Neelamani, R.G., Baraniuk, J.V., Rudd and Koch, M., "Recent advances in Terahertz imaging," Appl. Physics. B Lasers and Optics, vol. 68. pp. 1085-1094 (1999).

Piche, L.: "Ultrasonic velocity measurement for the determination of density in polyethylene". Polymer Engineering and Science, vol. 24, No. 17, Mid-Dec. 1984 pp. 1354-1358.

Roth, D.J.; Kiser, J.D.; Swickard, S.M., Szatmary, S., and Kerwin, D. "Quantitative Mapping of Pore Fraction Variations in Silicon Nitride Using an Ultrasonic Contact Scan Technique," Research in Nondestructive Evaluation, NASA Technical Paper 3377, Aug. 1993, pp. 1-29, National Aeronautics and Space Administration Washington, D.C. 20546-0001.

Roth, D.J., Carney, D.V., Baaklini G.Y., Bodis, J. R., Rauser, R. W., "A Novel Ultrasonic Method for Characterizing Microstructural Gradients in Tubular Structures," Materials Evaluation, vol. 56, No. 10, Sep. 1998 (paper submitted Apr. 1998), pp. 1053-1061.

Roth, D.J. and Farmer, D.A., "Thickness Independent Ultrasonic Imaging Applied to Abrasive Cut Off Wheels", Materials Evaluation, vol. 58, No. 4, Apr. 2000 (submitted Jun. 1998), pp. 551-557.

Roth, D.J., Hendricks, L., Whalen. M.F. and Martin, K: "Commercial Implementation of Ultrasonic Velocity Imaging Methods via Cooperative Agreement Between NASA Lewis Research Center and Sonix, Inc." NASA Technical Memorandum-107138, May 1996, pp. 1-40. National Aeronautics and Space Administration Washington, D.C. 20546-0001.

Winfree, W.P. and Madaras, E.I., "Detection and Characterization of Flaws in Sprayed on Foam Insulation with Pulsed Terahertz Frequency Electromagnetic Waves," American Institute of Aeronautics and Astronautics; AIAA-2005-3629, pp. 1-8 Proceedings of the 41st AIAA/ASME/SAE/ASEE Joint Propulsion Conference & Exhibit, Tuscon. Arizona, Jul. 10-13, 2005.

Dayal, V. "An Automated Simultaneous Measurement of Thickness and Wave Speed by Ultrasound," Experimental Mechanics, 32(3), pp. 197-202, Sep. 1992.

Inventor: Donald J. Roth, U.S. Appl. No. 12/163,382, entitled: "Simultaneous Noncontact Precision Imaging of Microstructural and Thickness Variation in Dielectric Materials Using Terahertz Energy"; Filing Date: Jun. 27, 2008.

\* cited by examiner

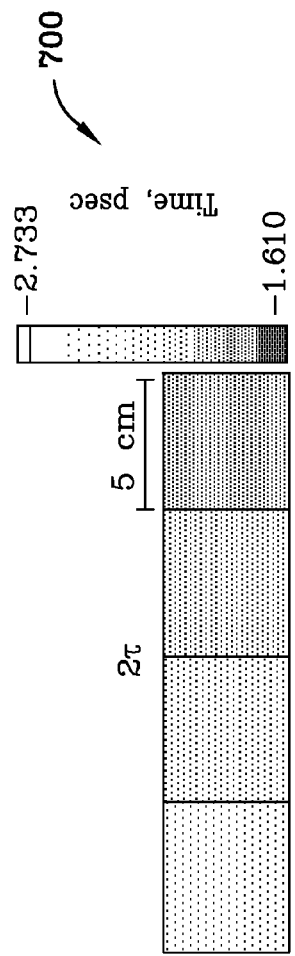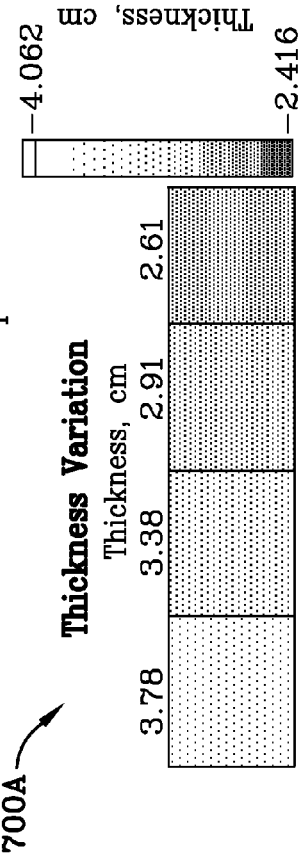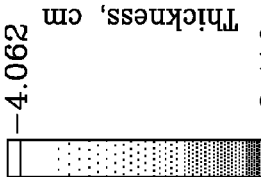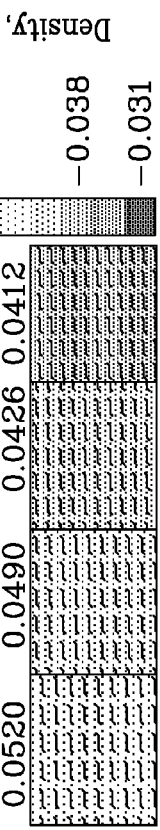

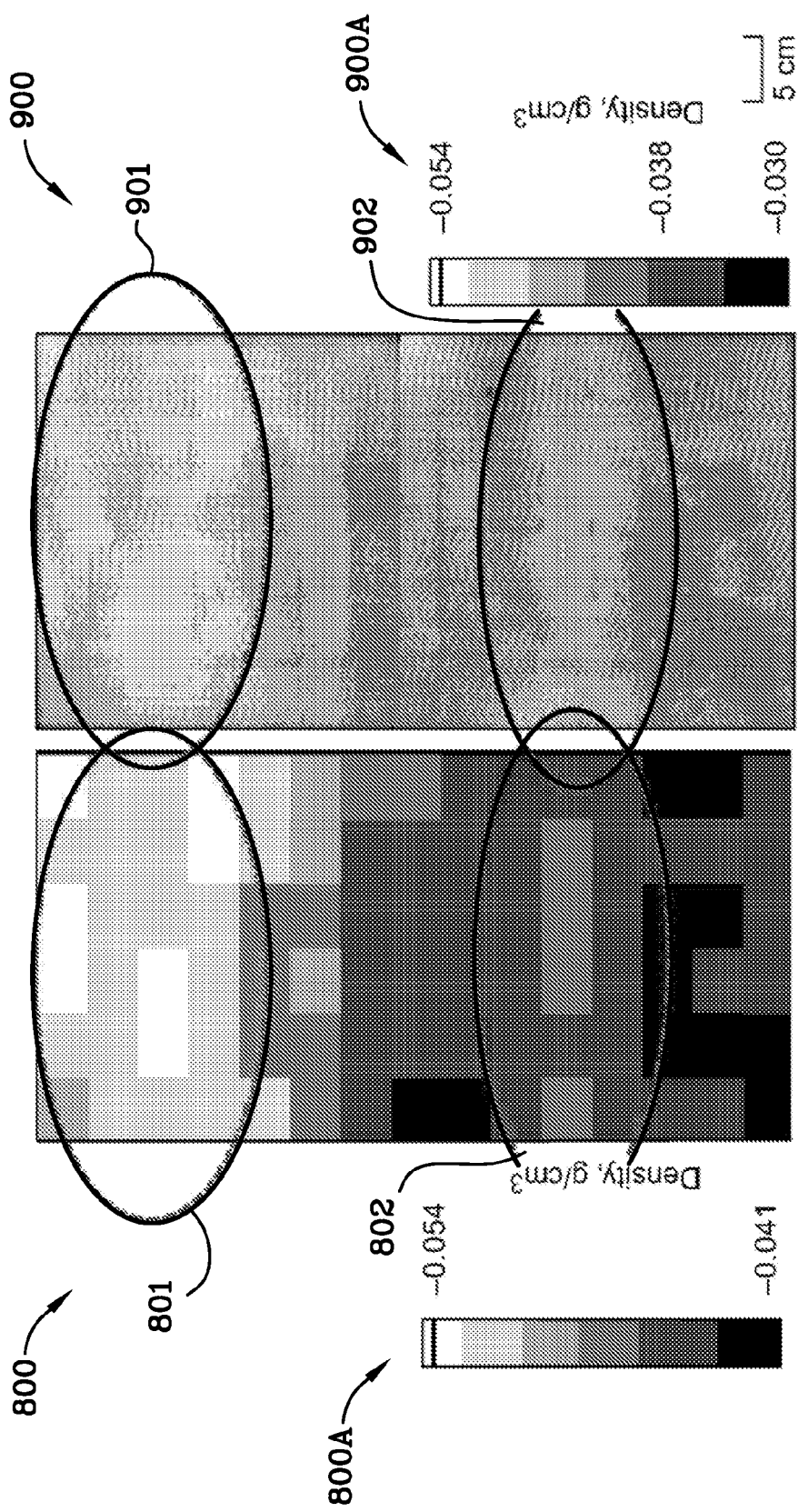

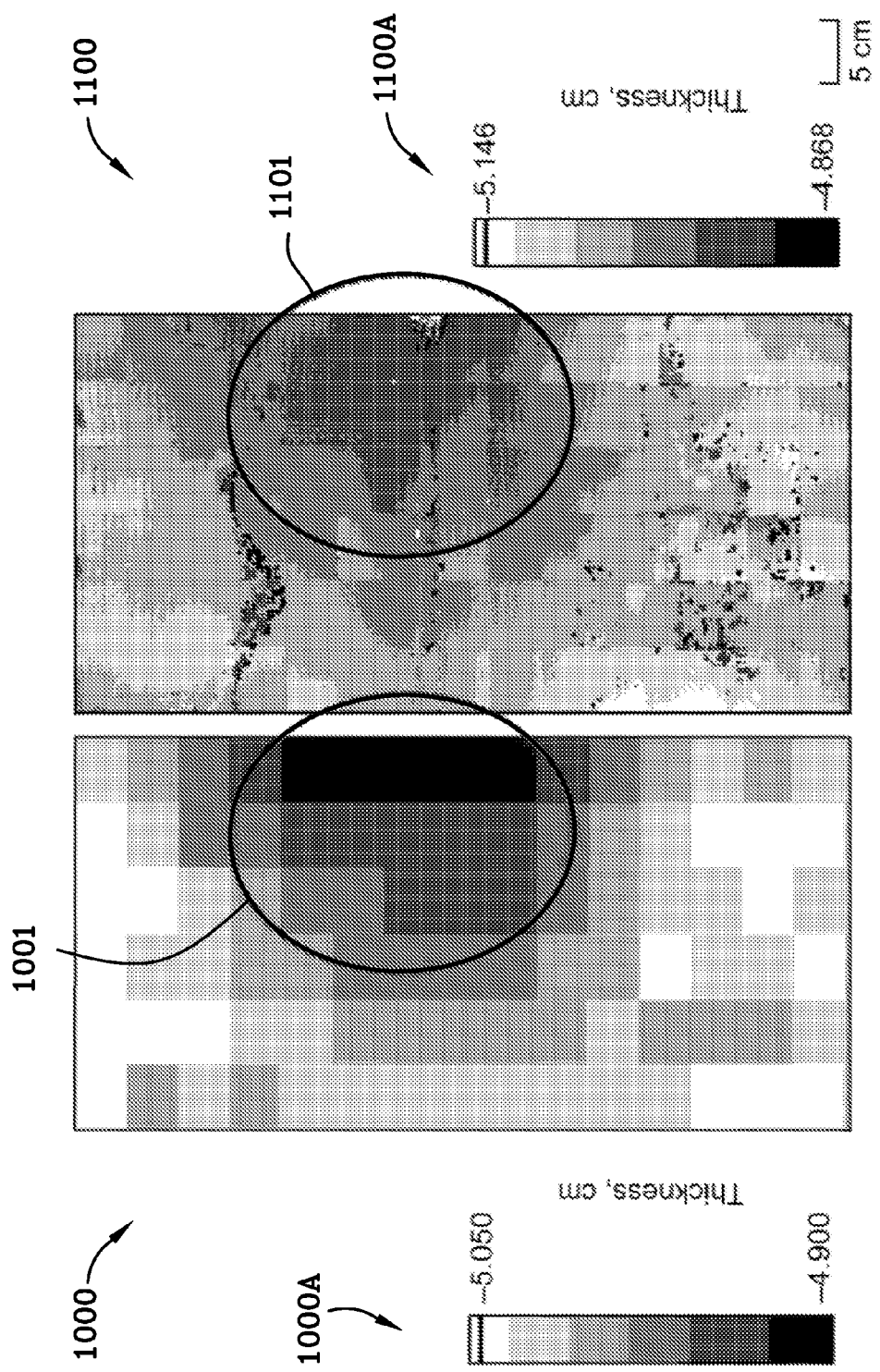

1700C

- calculating, on a scan point by scan point basis, the density of the sample without prior knowledge of the thickness of the sample 1717B
- determining and storing according to an algorithm, on a scan point by scan point basis, the velocity of terahertz electromagnetic radiation in the sample without prior knowledge of the thickness, according to the algorithm implementing the equation: $V= c(1-\Delta t/2\tau)$ 1717C
- determining according to the algorithm and storing, on a scan point by scan point basis, the thickness of the sample without prior knowledge of the velocity of the terahertz electromagnetic radiation in the sample 1718
- displaying, on a scan point by scan point basis, the thickness of the sample without prior knowledge of the velocity of the terahertz electromagnetic radiation in the sample 1718A
- determining according to the algorithm and storing, on a scan point by scan point basis, the thickness of the sample without prior knowledge of the velocity of the terahertz electromagnetic radiation in the sample, is performed according to the algorithm implementing the equation: $d= c(2\tau-\Delta t)/2$ 1718B
- step of fusing in the exemplary processes of Figs. 17 and 18 includes doubling the time base of the fused data waveform 1790
- steps of gating and conditioning the substrate echo (M") and the front surface (FS) echo waveforms in the exemplary process of Figs. 17 and 18 include the step of delaying the substrate echo in time to better gate the substrate echo and then remove the delay when the step of fusing the substrate echo (M") waveform and the front side echo (FS) waveform into the back side echo waveform (BS) is performed 1791

1807 using the stored values of $2\tau$ and $\Delta t$ in accordance with the algorithm to determine the velocity of the terahertz electromagnetic radiation in the sample on a scan point by scan point basis is performed

1808 step of determining and storing, on a scan point by scan point basis, the velocity, V, of terahertz electromagnetic radiation in the sample without prior knowledge of the thickness, velocity, V, is determined by solving the equation, $V = c(1-\Delta t/2\tau)$, for each the scan point and storing the determined velocity value in a velocity computer file on a scan point by scan point basis

1809 using the stored values of $2\tau$ and $\Delta t$ in the algorithm to determine the thickness of the sample on a scan point by scan point basis in accordance with the algorithm to determine on a scan point by scan point basis, the thickness, d, of the sample without prior knowledge of the velocity of the terahertz electromagnetic radiation in the sample, thickness is determined by solving the equation, $d = c(2\tau - \Delta t)/2$, for each the scan point and storing the thickness value in a thickness computer file

FIG. 18A

PROCESSING WAVEFORM-BASED NDE

This application is a continuation-in-part of application Ser. No. 12/163,382 filed Jun. 27, 2008 now U.S. Pat. No. 7,876,423. The instant application and application Ser. No. 12/163,382 filed Jun. 27, 2008 have the same inventor and are commonly owned by the same assignee.

ORIGIN OF THE INVENTION

The invention described herein was made by an employee of the United States Government, and may be manufactured and used by the government for government purposes without the payment of any royalties therein and therefor.

FIELD OF THE INVENTION

As a result of Space Shuttle Columbia Accident Investigation Board recommendations, an aggressive program to eliminate all External Tank Thermal Protection System debris-shedding at the source was initiated. Terahertz c-scan imaging is an emerging and very effective nondestructive evaluation (NDE) technique used for dielectric materials analysis and quality control in the pharmaceutical, biomedical, security, materials characterization, and aerospace industries.

BACKGROUND OF THE INVENTION

Flaws present in the Space Shuttle external tank thermal protection system may play a role in foam release and are therefore important to detect and characterize prior to flight. The external tank configuration has sprayed-on foam insulation placed on top of the metal container and thus lends itself to terahertz inspection. Terahertz inspection has shown significant promise for detection of voids in the foam. Other potentially undesirable foam anomalies that have been identified by NASA include density variations and crushed foam. Velocity imaging can be used to identify density variations.

Terahertz waves are electromagnetic waves with wavelengths on the order of 200 to 1000 μm. Reflections occur to varying degrees at interfaces between materials with dissimilar dielectric properties (difference in indices of refraction). Metallic materials totally reflect terahertz waves while non-polar liquids, dielectric solids, and gases are at least partially transparent to terahertz energy. Continuous wave (narrowband) and pulsed (broadband) terahertz systems exist.

Several attempts to separate thickness and microstructural variation effects in ultrasonic images are noted in the literature. Several references showed single point (non-imaging) ultrasonic measurement methodology that accounted for thickness variation effects. See, Sollish. B. D., Ultrasonic Velocity and Thickness Gage, U.S. Pat. No. 4,056,970, Nov. 8. 1977. Hsu, D. K. et al., Simultaneous determination of ultrasonic velocity, plate thickness and wedge angle using one-sided contact measurements, NDT&E International 1994 vol. 27, no. 2, pp. 75-82 and Piche, L., Ultrasonic velocity measurement for the determination of density in polyethylene, Polymer Engineering and Science, vol. 24, no. 17, Mid-December 1984 pp. 1354-1358. Hsu et. al, 1994, simultaneously determined ultrasonic velocity, plate thickness and wedge angle. Piche, 1984, described a single point ultrasonic velocity measurement method using a reflector plate located behind the sample that does not require prior knowledge of sample thickness and lends itself to multiple measurements within a sample of nonuniform thickness. Several references proceeded to scale up and automate this ultrasonic method to obtain ultrasonic velocity images for plate and cylindrical samples of various materials of non-uniform thickness. See, for example, Dayal, V., "An Automated Simultaneous Measurement of Thickness and Wave Speed by Ultrasound," Experimental Mechanics, 32(3), pp. 197-202, 1992; and, Roth, D. J., Carney, D. V., Baaklini, G. Y., Bodis, James R., Rauser, Richard W., "A Novel Ultrasonic Method for Characterizing Microstructural Gradients in Tubular Structures," Materials Evaluation, Vol. 56, No. 9, September 1998, pp. 1053-1061.

A procedure utilized in ultrasonics and terahertz in which the substrate reflector plate time-of-flight scan with no sample present is subtracted from the same scan with the sample in place is useful to characterize microstructure and correct for setup nonuniformity i.e., levelness, but it will not separate thickness and microstructural effects.

Ultrasonic methods to simultaneously measure or characterize thickness and density (or variation as such) require water coupling. Additionally, the ultrasonic methods cannot be used for foam inspections due to the highly porous nature or highly cellular structure of foams. The terahertz method is totally non-contact, requires no coupling, and works in air.

SUMMARY OF THE INVENTION

Terahertz imaging is being used at NASA for nondestructive evaluation of the Space Shuttle external tank thermal protection system sprayed-on foam insulation (SOFI). The NASA Engineering and Safety Center tasked a technical team to develop improved inspection methods to characterize foam anomalies to help alleviate foam shedding on the space shuttle tanks. Foam density variation was identified as a potential problem in which thermal expansion mismatch between areas of different density could result in crack formation, subsequent foam shedding, and endangerment of the space shuttle orbiter. Prior to implementation of the method disclosed herein it was not possible to quantitatively measure density using a totally non-contact, non-water-coupled method. Generally, terahertz is used in the pulse-echo c-scan configuration to map variations in the peak amplitude of the echo off of the metal substrate (equivalent to the location of the back surface of the foam) that occur when scanning across a section of foam in order to detect voids, cracks, disbonds, and any sort of discontinuity. Traditional c-scan imaging scales the peak amplitude values (to an 8- or 16-bit gray or color scale) at each scan location to form an image.

Since the pulse-echo terahertz method results in a waveform with echos being received off of the front surface of a dielectric material and a metal (electrically-conducting) substrate that the dielectric material rests on, obtaining the time delay between front surface and substrate (with the sample present) echos is possible. Terahertz velocity is affected by variations in a volumetric microstructural property such as physical density and thereby once a relationship between the two variables is established, a non-contact precise measurement of density can be made using terahertz energy.

If the dielectric material has flat and parallel sides such that no thickness variation exists, the time delay between the front surface echo and substrate echo with the sample present will be indicative of only microstructural variation. By obtaining the relationship between velocity and a microstructure property, such as density, using a series of samples of different density, one can then predict the density of the material and subsequently map density variations within the material using the established relation between velocity and density.

A pulse-echo terahertz velocity measurement is made by sending terahertz energy via a transceiver (device that has both a transmitter and a receiver) into and through a dielectric (insulating) material (such as the shuttle external tank thermal protection system sprayed on insulating foam) backed by a metallic (electrically-conducting) plate that reflects the terahertz energy back to the transceiver. The terahertz transceiver is separated from the dielectric sample by an air path. Velocity (V) values are calculated using the time delay between the front surface echo (FS) and substrate/reflector plate echo (BS). With a dielectric sample present between the transceiver and the reflector plate, the pulse that travels from the transceiver through the sample to the reflector plate (equivalent to the sample back surface position) and back to the transceiver is labeled BS and will be observed at time t'. Thus two "echos," FS and BS, can have their peak positions in time measured and the time difference or time delay between them is determined. Alternatively, the entire echos may be cross-correlated to obtain the precise time delay between them. If thickness is non-variable in the sample, the time-of-flight and/or velocity measured will be indicative only of the microstructure. The FS echo may require specialized signal processing to denoise and amplify it.

A process for measuring the velocity of terahertz electromagnetic radiation in a material sample without prior knowledge of the thickness of the sample is disclosed and claimed. Terahertz electromagnetic radiation is produced by a source (transceiver) spaced apart from the substrate and propagated at the speed of light, c, in a medium located between the source (transceiver) and the substrate. The process for measuring the velocity (independently of thickness) includes the following steps: emitting terahertz electromagnetic radiation from the source; measuring the travel time of the terahertz electromagnetic radiation to and from the substrate without the sample present, t" (t-double prime); placing the sample on the substrate; measuring the travel time of the terahertz electromagnetic radiation to and from the substrate with the sample present, t' (t-prime); subtracting t" from t' to determine the transmission time difference with the sample present and without the sample present, $\Delta t$; measuring the travel time of the terahertz electromagnetic radiation to and from the sample, $2t_1$; time determining the difference between the FS echo and the BS echo, $2\tau$; dividing $\Delta t$ by $2\tau$ and determining the quotient; and, subtracting the quotient from 1 to obtain a factor; multiplying the factor by, c, to determine the velocity of the terahertz electromagnetic radiation in the sample. The further step of determining the microstructural variation of the sample according to an algorithm is performed to determine, for instance, the density of the foam. The step of determining the microstructual variation of the sample includes determining the density of the material. The sample may be foam or another dielectric such as silicon nitride. The radiation may be pulsed or it may be continuous.

If the surface to be evaluated is large, then mapping microstructural variations in a plurality of locations is performed. When the terahertz electromagnetic radiation reaches the front surface of the sample, the echo therefrom may not be very prominent if the dielectric mismatch between the air path and the sample and the dielectric itself is not substantial enough. The step of measuring the travel time of the terahertz electromagnetic radiation to and from the sample, $2t_1$ optionally includes placing a sheet of plastic transparent paper onto the sample to create an adequate dielectric mismatch between the air and the sample. The plastic transparent paper is thin, for example, it may be approximately 250 μm thick or less. The plastic paper does not have to be transparent. It is necessary to know, a priori, the approximate distance between the transceiver and the front surface of the sample. As used herein "a priori" means before knowledge of the exact distances between the transceiver and the front surface of the sample.

The front surface echo (FS) from the dielectric material (sample) may be of very low signal-to-noise ratio (SNR) depending on the dielectric match between air and the sample. If a good dielectric match exists, much of the terahertz energy will be transmitted into the sample. Additionally, the focal plane sensitivity of the terahertz method disclosed herein, may, for samples of nonuniform thickness, result in the front surface echo (FS) too far out of focus and thus reduces the signal to noise ratio (SNR) even further, thus limiting the thickness variation over which the method can be used. The approximate time location of FS must be known "a priori" and the wavetrain examined manually through observation of the signal on an oscilloscope trace to determine what special post-processing needs to be applied. In this way amplification and denoising the front surface signal (FS) can be achieved. Therefore, the further process steps of controlling, approximately, the spacing between the source (transceiver) and the substrate and the spacing between the source and the front surface are usually performed preliminarily if necessary. It is also necessary to know the approximate distance between the transceiver and the metal substrate.

The step of controlling the spacing between the source and the substrate includes determining, initially, the approximate time location of the sample from the terahertz radiation source as well as the approximate time location of the substrate from the terahertz radiation source.

Identical scan data may be used for measuring the thickness of a material sample using terahertz electromagnetic radiation in a material sample without prior knowledge of the velocity of the terahertz electromagnetic radiation in the sample. In other words density and thickness can be obtained from the same scan data. The terahertz electromagnetic radiation is produced by a source (transceiver) spaced apart from the substrate and propagated at the speed of light, c, in a medium (usually air) located between the source and the substrate. The steps in the process include: emitting pulsed (or continuous) terahertz electromagnetic radiation from the source; measuring the travel time of the terahertz electromagnetic radiation to and from the substrate without the sample present, t" (t-double prime); placing the sample on the substrate; measuring the travel time of the terahertz electromagnetic radiation to and from the substrate with the sample present, t' (t-prime); subtracting t" from t' to determine the transmission time difference with the sample present and without the sample present, $\Delta t$; measuring the travel time of the terahertz electromagnetic radiation to and from the sample, $2t_1$; determining the time difference between the FS echo and the BS echo, $2\tau$; subtracting $\Delta t$ from $2\tau$ to obtain a subtraction result; dividing the subtraction result by 2 to obtain a quotient; and, multiplying the quotient by, c, to obtain the thickness of the sample. Additionally, the method for determining thickness may include evaluating, in a plurality of locations, the sample for thickness variations and mapping the thickness variations by location.

The inventor discloses and claims herein a process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample. The pulsed terahertz electromagnetic radiation is produced by a source spaced apart from the sample under test and propagated at the speed of light, c, in a medium located between the source and the sample. The medium is typically air. The process includes the steps of: emitting (pulsed or continuous) terahertz electromagnetic radiation from the source; measuring the travel time of the terahertz electromagnetic radiation to and from the substrate without the sample present, t" (t-double prime); placing the sample on the substrate; measuring the travel time of the terahertz electromagnetic radiation to and from the substrate with the sample present, t' (t-prime); subtracting t" from t' to determine the transmission time difference with the sample present and without the sample present, $\Delta t$; measuring the travel time of the terahertz electromagnetic radiation to and from the sample, $2t_1$; determining the time difference between the FS echo and the BS echo, $2\tau$; dividing $\Delta t$ by $2\tau$ and determining the quotient; subtracting the quotient from 1 to obtain a factor; multiplying the factor by, c, to determine the velocity of the terahertz electromagnetic radiation in the sample; subtracting $\Delta t$ from $2\tau$ to obtain a subtraction result; dividing the subtraction result by 2 to obtain a quotient; multiplying the quotient by, c, to obtain the thickness of the sample; and, evaluating, in a plurality of locations, the sample for microstructural variations and for thickness variations, and mapping the microstructural and thickness variations by location.

Another process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample is disclosed herein which comprises the steps of: merging the FS, BS, and M" scan data sets into a fused data file; producing a "fused" waveform; calculating time delays between FS, BS and M"echos; determining precision thickness-independent velocity images that map microstructure; and, determining precision microstructure-independent thickness images that map thickness. The steps of calculating the time delays and determining precision thickness and microstructure are performed by cross-correlating FS and BS signals (echos) and by cross correlating BS and M" signals (echos). The steps of calculating the time delays and determining precision thickness and microstructure may also be performed by precisely identifying peaks of FS, BS and M". Where FS is believed to vary across a sample, an additional step of processing and gating the FS signal prior to merging the data into a fused data file is performed. Optionally, the step of amplifying the processed FS signal prior to merging the data into a fused data file is performed. To obtain a good dielectric mismatch between the sample and the air, the step of applying a dielectric sheet on the FS, followed by gating and processing the FS signal prior to merging the data into a fused data file is performed.

The methodology disclosed herein has applicability to all dielectric materials where non-contact, non-water-immersion precision determination of microstructural (density) variation is required. It can be used for precision density mapping in dielectric ceramic materials, other types of foam, and dielectric composite materials.

C-scan imaging involves mapping variations in the time-of-flight of a terahertz echo peak, or mapping the time delay between front surface and substrate (with the sample present) echos (FS, BS). The novel implementation described herein concerns itself more with mapping thickness or global microstructural variation (such as physical density variation) as opposed to discrete flaw detection. Time delay between the front surface echo (FS) and substrate echo (BS) (with the sample present) is directly affected by thickness variation (d) and terahertz velocity in the material (V). Terahertz velocity is affected by variations in a volumetric microstructural property such as physical density.

The terahertz method of inspecting metal reflector-backed dielectric materials provides velocity images free of thickness variation effects, i.e. thickness-independent. Additionally, the same methodology can be slightly manipulated to obtain thickness images free of microstructural variation effects, i.e. microstructure-independent. In simple terms thickness can be measured without knowing velocity and density or velocity can be measured without knowing thickness. A pulse-echo terahertz velocity measurement is made by sending terahertz energy via a transceiver (device that has both a transmitter and a receiver) into and through a dielectric (insulating) material (such as the shuttle external tank thermal protection system sprayed on insulating foam) backed by a metallic (electrically-conducting) plate that reflects the terahertz energy back to the transceiver. The terahertz transceiver is separated from the dielectric sample by an air path. Velocity (V) values are calculated using the time delay (a) between the front surface echo (FS) and substrate reflection (BS) (with sample present). The novel pulse-echo method described herein for measuring velocity in a material sample uses echos off of the reflector plate without the sample present as well as the FS and BS echos with the sample present.

With a dielectric sample present between the transceiver and the reflector plate, the pulse that travels from the transceiver through the sample to the reflector plate (equivalent to the sample back surface position) and back to the transceiver is labeled BS and will be observed at time t'. Placing a dielectric sample in between the terahertz transceiver and the reflector plate slows down the terahertz pulse as compared to its travel time in air. Thus, with the sample removed, the pulse that travels from the transceiver to the reflector plate and back to the transceiver is labeled M" and will be observed at an earlier time t". For certain materials such as foams, by appropriate manipulations and substitutions of equations, the acquisition of scans of the FS, BS, and M" (echo off reflector without sample present) echos, the conditioning of the FS echo thru amplification, DC subtraction, and software denoising, the fusing (combining) of FS, BS, and M" data sets (through use of software), and the subsequent calculation of time delays between echos, precision thickness-independent velocity images (that map microstructure) and microstructure-independent thickness images (that map thickness) (through software) are obtained.

The use of terahertz energy to simultaneously determine density and thickness variation in dielectric materials is new. The method is totally non-contact, very precise, and involves no fluid immersion.

Prior to implementation of this method, it was not possible to separate out effects of thickness and microstructural variation in time-of-flight images in totally non-contact, non-water-immersion fashion. No attempts to separate thickness and microstructural effects in terahertz time-of-flight images were noted in the literature. Ultrasonic methods to simultaneously measure or characterize thickness and density (or variation as such) require water coupling. Additionally, the ultrasonic methods cannot be used for foam inspections due to the highly porous nature or highly cellular structure of foams. The terahertz method is totally non-contact, requires no coupling, and works in air.

A process for non-destructive evaluation of a sample using a computer and a computer program implementing an algorithm is disclosed and claimed. The algorithm includes determining the velocity of terahertz electromagnetic radiation in the sample without prior knowledge of the thickness of the sample and determining the thickness of the sample without prior knowledge of the velocity of the terahertz electromagnetic radiation in the sample. The terahertz electromagnetic radiation is produced by a source spaced apart from the sample under test and propagated at the speed of light, c, in a medium located between the source and the sample. The steps include emitting and scanning terahertz electromagnetic radiation from the source. The terahertz radiation is applied to a plurality of scan points arranged according to x and y coordinates of the source. The plurality of scan points includes an area at least as large as the surface of the sample. Recording and storing in a substrate echo waveform data set file, on a scan point by scan point basis, the substrate echo (M") waveform of the terahertz electromagnetic radiation received from the substrate without the sample present is performed. The next step is placing the sample on the substrate. Next, the step of recording and storing in a back surface echo waveform data set file, on a scan point by scan point basis, the back surface echo (BS) waveform of the terahertz electromagnetic radiation received from the substrate with the sample present, t' (t-prime, back surface echo (BS)). Then an additional step of recording and storing in a front surface echo (FS) waveform data set file, on a scan point by scan point basis, is undertaken. The front surface echo (FS) waveform of the terahertz electromagnetic radiation is received from the front surface of the sample.

Once the aforementioned waveform files are generated, the step of recalling the stored substrate echo (M") waveform data set file, recalling the stored back surface echo (BS) waveform data set file, and recalling the stored front surface echo (FS) waveform data set file is performed. Next the step of opening and viewing, interactively, the substrate echo (M") waveform, the front surface echo (FS) waveform and the back surface (BS) echo waveform is performed. The substrate echo (M") waveform, the front surface echo (FS) waveform, and the back surface echo (BS) waveform for a single scan point, are superimposed in a display indicating amplitude and time base. The software next permits viewing, interactively, an algorithm-generated amplitude display of all scan points and associated substrate (M") waveforms, associated front surface (FS) waveforms and associated back surface echo (BS) waveforms, for selected scan points of the sample arranged according to x and y scan coordinates. The user may canvass any of the superimposed waveforms to obtain an idea or range of values for subsequent gating. Next, the software applies gating, interactively, the front surface echo (FS) waveform and the substrate echo (M") waveform based on ranges determined from viewing selected scan points of the sample. The gating windows the FS and M" echoes of the scan points so that the windowed portions can be extracted and combined (fused) with the BS echoes at the same scan point. Conditioning, if necessary of the front surface echo (FS) waveform is facilitated by the software.

Fusing the stored substrate echo (M") waveform data set file, the stored back surface echo (BS) waveform data set file, and the stored front surface echo (FS) waveform data set file, together, producing a fused data file for each of the scan points, is performed by the software. Next the software facilitates viewing, interactively, an algorithm-generated amplitude display of the fused waveforms associated with all scan points for selected scan points of the sample arranged according to x and y scan coordinates.

Again, the software facilitates gating, interactively, the front surface (FS) echo waveform and gating, interactively, the back surface (BS) echo waveform of one of the fused waveform files based on ranges determined from viewing a range of the selected fused waveforms. A calculation of the difference in time, $2\tau$, between the front surface (FS) echo waveforms and the back surface (BS) echo waveforms on a scan point by scan point basis is made by the software and a $2\tau$ file is generated and stored.

Again, the software facilitates gating, interactively, the back surface (BS) echo waveform and gating, interactively, the substrate (M") echo waveform of one of the fused waveform files based on ranges determined from viewing one of the selected fused waveforms. Next, a calculation of the difference in time, $\Delta t$, between the front surface (BS) echo waveforms and the substrate (M") echo waveforms on a scan point by scan point basis is generated and stored as a $\Delta t$ file. The generation of the $2\tau$ and $\Delta t$ files enables the step of determining and storing, on a scan point by scan point basis, the velocity of terahertz electromagnetic radiation in the sample without prior knowledge of the thickness of the sample. Further, generation of the $2\tau$ and $\Delta t$ files enables determining and storing, on a scan point by scan point basis, the thickness of the sample without prior knowledge of the velocity of the terahertz electromagnetic radiation in the sample.

It is an object of the invention to simultaneously: (1) measure the velocity of terahertz electromagnetic radiation in a material sample without prior knowledge of the thickness of the sample; and, (2) measure the thickness of a material sample using terahertz electromagnetic radiation in a material sample without prior knowledge of the velocity of the terahertz electromagnetic radiation in the sample.

It is an object of the invention to provide a non-contact single-sided terahertz electromagnetic measurement and imaging method that simultaneously characterizes microstructural (for example, spatially-lateral density) and thickness variation in dielectric (insulating) materials.

It is an object of the present invention to provide a non-contact single-sided terahertz electromagnetic measurement and imaging method that simultaneously characterizes microstructural and thickness variation in dielectric (insulating) materials.

It is an object of the present invention to provide an inspection method for current and future thermal protection systems and for other dielectric material inspection applications where microstructural and thickness variation require precision mapping.

It is an object of the present invention to provide an inspection method which allows the separation of time-of-flight variations into its microstructural and thickness components.

It is an object of the present invention to provide simultaneous noncontact precision imaging of microstructural and thickness variation in dielectric materials using terahertz energy.

It is an object of the present invention to provide simultaneous noncontact precision imaging of microstructural and thickness variation in dielectric materials using terahertz energy using fused waveforms of terahertz energy from a fused data files produced by merging the FS, BS, and M" scan data sets for a set of foam blocks.

It is an object of the present invention to provide an imaging of microstructural and thickness variation in dielectric materials using terahertz electromagnetic through the creation of scan data arranged in an x-y matrix of scan points.

It is an object of the present invention to provide a computer algorithm which enables mapping of scan data arranged in an x-y matrix which provides information about the velocity/density of the sample under evaluation/test without knowing the thickness of the sample under evaluation/test.

It is an object of the present invention to provide a computer algorithm which enables mapping of scan data arranged in an x-y matrix which provides information about the thickness of the sample under evaluation/test without knowing the density of the sample under evaluation.

It is an object of the present invention to provide a system which includes a computer algorithm for creating back surface (BS) waveform data files, substrate echo (M") waveform data files, and front surface (FS) waveform data files.

It is an object of the present invention to provide a system which includes a computer algorithm which provides interactive viewing of the back surface (BS) waveform data files, substrate echo (M") waveform data files, and front surface (FS) waveform data files for the determination of gating (windowing) the substrate echo (M") waveforms and the front surface (FS) waveforms and the subsequent fusing of the data files on a scan point by scan point basis for the creation of fused data files for each scan point.

It is an object of the present invention to provide a system which includes a computer algorithm which provides gating the front surface (FS) echo and the back surface (BS) echo for the determination of a matrix of $2\tau$ data files on a scan point by scan point basis.

It is an object of the present invention to provide a system which includes a computer algorithm which provides gating the substrate (M") echo and the back surface (BS) echo for the determination of a matrix of $\Delta t$ data files on a scan point by scan point basis.

It is an object of the present invention to provide a system which includes an image of the velocity of the terahertz radiation in the sample, and, hence the density of the sample without prior knowledge of the thickness of the sample.

It is an object of the present invention to provide a system which includes an image of the thickness the sample without prior knowledge of the velocity of the radiation in the sample.

It is an object of the present invention to provide a computer and computer software for recording and storing front surface (FS) echo files, substrate echo (M") files and back surface (BS) echo files and superimposing them in a time based file on a scan point by scan point basis.

It is a further object of the present invention to gate (window) superimposed data after inspecting the superimposed data and to produce a fused file for each scan point which includes a front surface (FS) echo waveform, a substrate (M") waveform, and a back surface (BS) echo waveform fused together.

It is a further object of the present invention to gate a selected fused waveform for calculating $2\tau$ and $\Delta t$ on a scan point by scan point basis and then calculate and output velocity (density) and thickness plots.

These and other objects will be better understood when reference is made to the drawings, the description of the invention and claims which follow herein below.

BRIEF DESCRIPTION OF THE DRAWINGS

FIG. 7 illustrates a composite image of scans of the foam block sample set of FIG. 6 indicating $2\tau$ values of the foam blocks according to the methodology of the invention.

FIG. 7A illustrates an image of scans of the foam block sample set of FIG. 6 indicating thickness variations according to the methodology of the invention.

FIG. 7B illustrates an image of scans of the foam block sample set of FIG. 6 indicating density variations according to the methodology of the invention.

FIG. 8 illustrates a physically-measured density map in grams per cubic centimeter for a 6 by 15 set of foam blocks.

FIG. 8A illustrates the density by shade of gray in grams per cubic centimeter for the physically-measured density map shown in FIG. 8.

FIG. 9 illustrates a terahertz density map in grams per cubic centimeter for the 6 by 15 set of foam blocks of FIG. 8 derived from the velocity variations (determined independently of thickness) according to the methodology of the invention using the relationship between terahertz velocity and density for foam shown in FIG. 2.

FIG. 9A illustrates the density by shade of gray in grams per cubic centimeter for the terahertz density map of FIG. 9.

FIG. 10 illustrates a hand-measured thickness map in centimeters for the 6 by 15 set of foam blocks.

FIG. 10A illustrates the thickness by shades of gray indicated in centimeters for the thickness map of FIG. 10.

FIG. 11 illustrates a terahertz thickness map for the 6 by 15 set of foam blocks (determined independently of velocity) according to the methodology of the invention.

FIG. 11A illustrates the thickness by shade of gray in centimeters for the terahertz thickness map of FIG. 11.

FIGS. 18-18A are another schematic of an exemplary computer implemented process for nondestructively determining terahertz electromagnetic radiation velocity without prior knowledge of thickness of a sample for determining thickness without prior knowledge of the terahertz electromagnetic radiation velocity in the sample.

DESCRIPTION OF THE INVENTION

Figure 1:
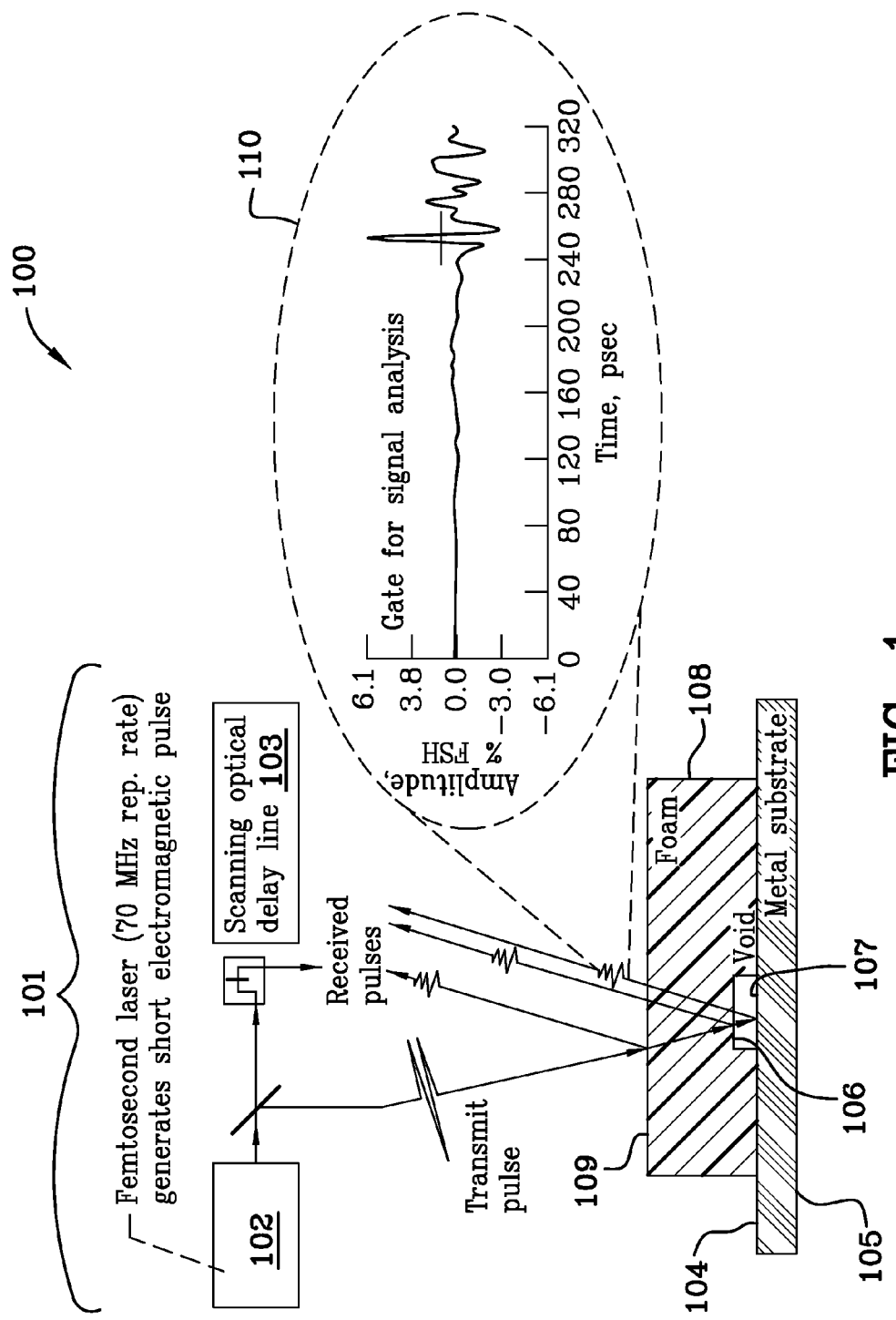
FIG. 1 is a schematic diagram of the reflection-mode terahertz methodology illustrating reflections received from the various interfaces and as an example of gating of the reflected signals.

FIG. 1 is a schematic diagram 100 of the reflection-mode terahertz methodology illustrating reflections received off of the various interfaces and gating of the reflected signal. A transceiver 101 includes a femtosecond laser (70 MHZ rep. rate) 102 which generates short terahertz electromagnetic pulses and a receiver 103. Reflections will be received from the various interfaces 109, 104. Reflection from the metal substrate 104 will be the strongest. The horizontal dotted line from the echo shows a time gate 110 typically used during signal processing. The back surface 105 of the metal substrate is illustrated as is the beginning of the void 106 in the foam, silicon nitride or other dielectric 108. The void in this example terminates 107 at the front surface of the metal substrate 104. The front surface of the foam, silicon nitride or other dielectric 109 is illustrated in FIG. 1 as is a graphical depiction of a gate 110 for signal analysis.

Terahertz imaging is being used at NASA for nondestructive evaluation of the Space Shuttle external tank thermal protection system sprayed-on foam insulation (SOFI). Generally, the terahertz method is used in the pulse-echo c-scan configuration to map variations in the peak amplitude of the echo off of the metal substrate after it has traveled through the foam. Traditional c-scan imaging scales the peak amplitude values (to an 8- or 16-bit gray or color scale) at each scan location to form an image.

An additional implementation of pulse-echo c-scan imaging involves mapping variations in the time-of-flight of a terahertz echo peak, or mapping the time delay between front surface and substrate (with the sample present) echos (FS, BS). This implementation concerns itself more with mapping thickness or global microstructural variation (such as physical density variation) as opposed to discrete flaw detection. Time delay (with the sample present $2\tau$) between the front surface echo (FS) and substrate echo (BS) is directly affected by thickness variation and terahertz velocity in the material according. See, FIG. 3. Here the designations $(2\tau)$ and $(2d)$ (versus $\tau$ and d) are used since the ultrasonic echo travels through the material thickness in the pulse-echo mode.

Figure 2:
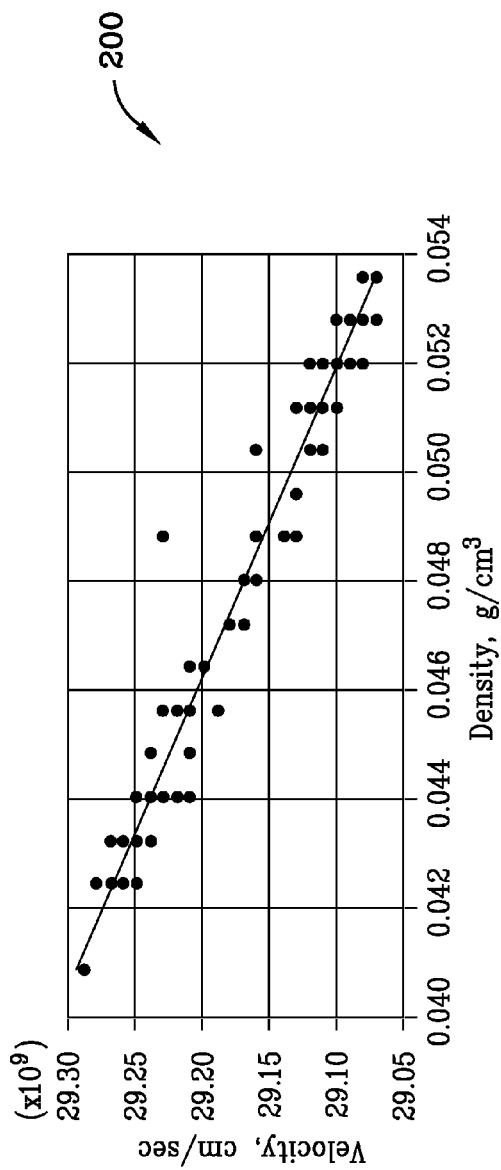
FIG. 2 is a plot of velocity versus density for foam.

Terahertz velocity is affected by variations in a volumetric microstructural property such as physical density as illustrated in FIG. 2, similar to the way ultrasonic velocity responds to microstructural variation.

Determining the relationship between velocity and density allows density maps to be obtained from velocity maps as set forth herein. Spatial variations in part thickness and/or spatially-lateral microstructural character will result in variations in maps of $2\tau$. Analagous to a complex number having real and imaginary parts, $2\tau$ images can be thought of as having thickness and microstructural components if both thickness and microstructural variation are present.

Figure 2A:
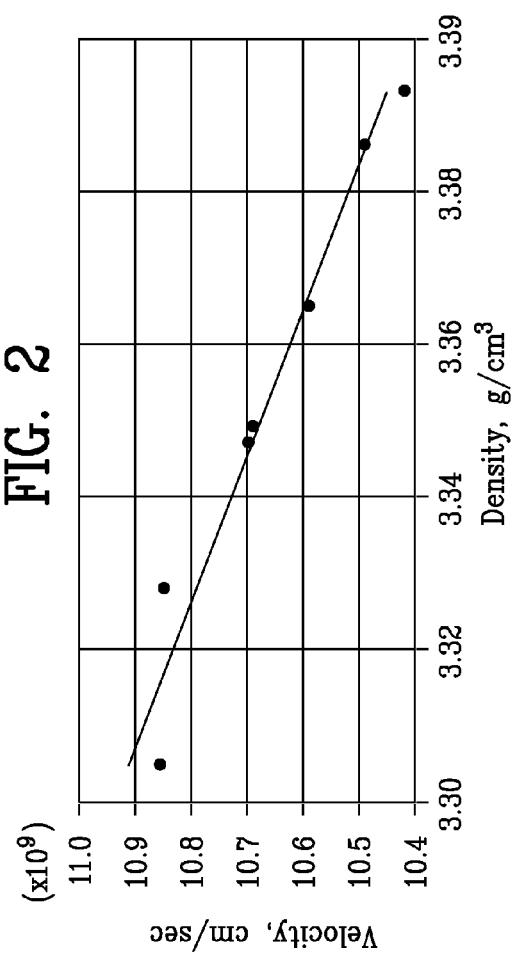
FIG. 2A is a plot of velocity versus density for silicon nitride.

A terahertz method which allows the separation of time-of-flight variations into its microstructural and thickness components is disclosed herein. This method is important because it determines the extent of microstructural variation in a part that also has thickness variation. Additionally, it provides a non-contact method for mapping thickness and/or density. FIG. 2 is a plot 200 of terahertz electromagnetic radiation velocity versus density for sprayed on foam. This enables the conversion of a given velocity into a respective density. FIG. 2A is a plot 200A of terahertz electromagnetic velocity versus density for silicon nitride.

Figure 3:
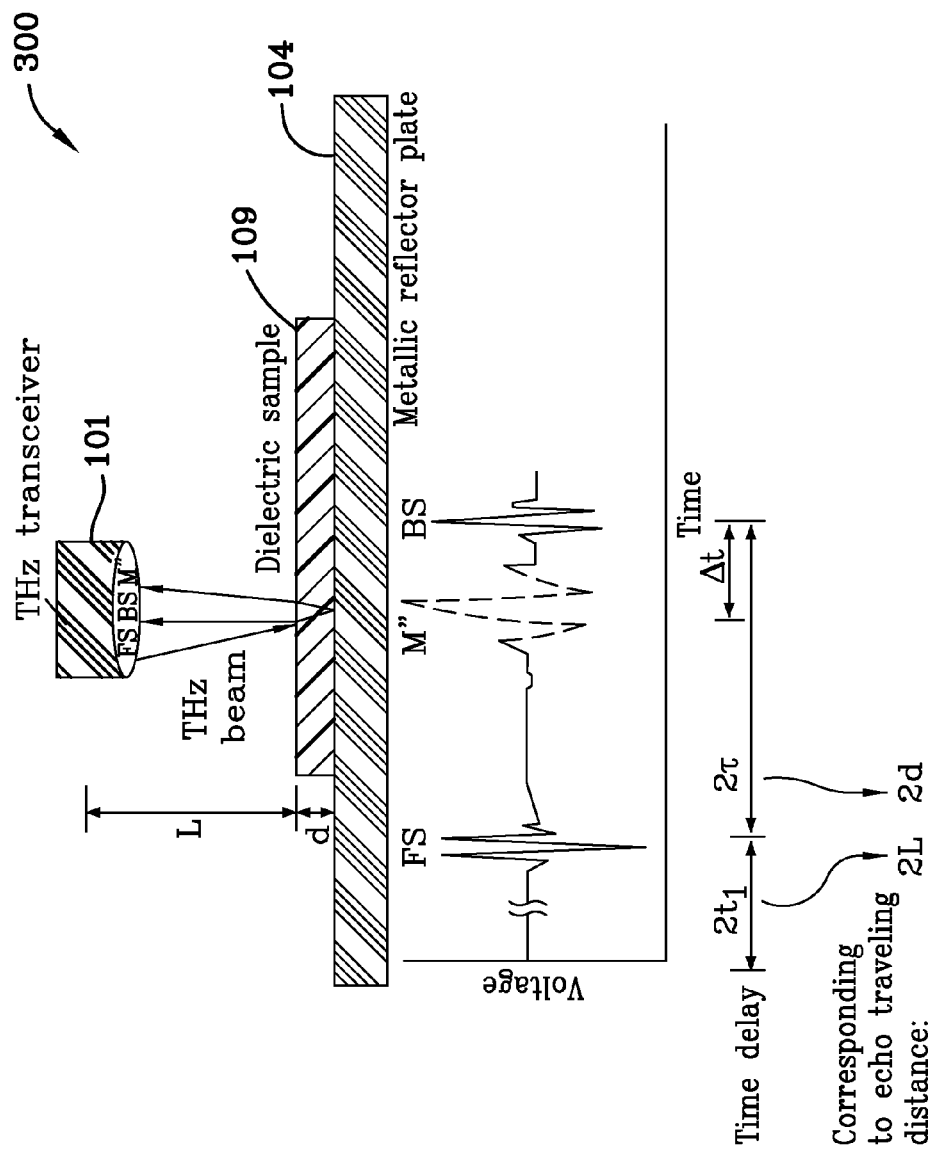
FIG. 3 illustrates a schematic of the pulse-echo terahertz testing method and resulting waveforms, including BS (time to and from the back surface of the dielectric sample), FS (time to and from the front surface of dielectric sample), L (distance between transceiver and sample), M" (pulse that travels from the transceiver to the reflector plate and back to the transceiver), d (sample thickness), t' (t-prime) (travel time of the terahertz electromagnetic radiation to and from the substrate with the sample present, equal to $2t_1$ plus $2\tau$), t" (t-double prime) (travel time of the terahertz electromagnetic radiation to and from the substrate without the sample present), $\Delta t$-(transmission time difference (t' minus t") with the sample present and without the sample present), $2t_1$ (travel time of the terahertz electromagnetic radiation to and from the front surface of the sample) and $2\tau$ (time difference between the FS echo and the BS echo).

FIG. 3 illustrates a schematic 300 of the pulse-echo terahertz testing method and resulting waveforms (output voltages), including: BS (time to and from the back surface of dielectric sample); FS (time to and from the front surface of the dielectric sample); L (distance between transceiver and sample); M"(pulse that travels from the transceiver to the reflector plate and back to the transceiver), d (sample thickness), t' (t-prime) (travel time of the terahertz electromagnetic radiation to and from the substrate with the sample present, equal to $(2t_1)$ plus $(2\tau)$; t" (t-double prime) (travel time of the terahertz electromagnetic radiation to and from the substrate without the sample present), $\Delta t$ transmission time difference (t' minus t") with the sample present and without the sample present; $2t_1$ (travel time of the terahertz electromagnetic radiation to and from the front surface of the sample); and, $2\tau$ (time difference between the FS echo and the BS echo).

As stated previously, the terahertz method of inspecting metal reflector-backed dielectric materials is utilized to simultaneously provide thickness-independent velocity (free of thickness effects) and microstructure-independent thickness (free of microstructure effects) images. A pulse-echo terahertz velocity measurement is made by sending terahertz energy via a transceiver (device that has both a transmitter and a receiver) into and through a dielectric (insulating) material backed by a plate (electrically-conducting, generally metallic) that reflects the terahertz energy back to the transceiver. The terahertz transceiver is separated from the dielectric sample by an air path.

The novel pulse-echo method described herein for measuring velocity in a material sample uses echoes off of the reflector plate with (BS) and without the sample present (M"), as well as using the echo (FS) off of the sample front surface. The following steps illustrate how velocity (V) in a sample of thickness (d) is determined without prior knowledge of thickness. With a dielectric sample present between the transceiver and the reflector plate, the pulse that travels from the transceiver through the sample to the reflector plate (equivalent to the sample back surface position) and back to the transceiver is labeled BS and will be observed at time t' where: $t'=(2t_1+2\tau)$ Referring to FIG. 3, the pulse-echo terahertz testing and resulting waveforms of FS and BS occur with the sample present. M" occurs without the sample present. $(2t_1)$ and $(2\tau)$ are the pulse-echo time delays of the terahertz pulse from the transceiver to the sample front surface and from the sample front surface to the substrate with the sample present.

Placing a dielectric sample in between the terahertz transceiver and the reflector plate slows down the terahertz pulse as compared to its travel time in air. Thus, with the sample removed, the pulse that travels from the transceiver to the reflector plate (metal substrate) 104 and back to the transceiver is labeled and will be observed at an earlier time t" where:

$$t''=(2t_1+2d/c))$$

where, c, is the velocity of terahertz energy in air and, d, is the air gap equal to the sample thickness.

The velocity of light at standard temperature and pressure was used for c in this investigation and is equal to 0.02997055434 cm/psec. Subtracting the time t" measured without the sample from the time measured with the sample, t', yields $\Delta t$, follows:

$$\Delta t=t'-t''=(2\tau-2d/c)$$

The thickness (d) of the sample can be determined in the pulse-echo configuration from:

$$2d=(2\tau)V$$

which is simply velocity times time through the sample in both the forward and reverse directions. Solving for "d" and rearranging yields an expression for the velocity:

$$V=c(1-\Delta t/2\tau)$$

As seen from the equation for velocity, sample thickness (d) is not a variable in the equation. Thus, this method does not require prior knowledge of sample thickness. If extended to multiple measurements across the sample (imaging), sample thickness variation effects are eliminated in the image allowing a true picture of microstructural variation for types of microstructural variation (such as density variation) that correlate with and will be revealed by velocity variation. For conventional time-of-flight imaging which does not separate velocity, V, and thickness, d, any thickness variation effects would corrupt the evaluation of microstructural variation (determined from velocity, V). Thus the new methodology allows true characterization of microstructural variation (i.e., density variation) in a material structure that is also nonuniformly thick.

The derived equation, namely, $V=c(1-\Delta t/2\tau)$, illustrates how the terahertz velocity in a dielectric material will be reduced fractionally from that in air by the factor:

$$(1-\Delta t/2\tau).$$

Further, rearranging $\Delta t=t'-t''=(2\tau-2d/c)$, to solve for sample thickness, d, yields:

$$d=c(2\tau-\Delta t)/2$$

which allows the calculation of absolute material thickness without prior knowledge of velocity. If extended to multiple measurements across the sample (imaging), sample microstructure variation effects are eliminated in the image allowing a true mapping of thickness variation. For conventional thickness mapping, microstructure variation effects would corrupt the evaluation of thickness variation.

Thus, the new methodology allows true characterization of thickness variation in a material structure that is of nonuniform microstructure. A key point of the methodologies disclosed and claimed herein is that both thickness-independent velocity and microstructure-independent thickness images can be derived from the same set of scan information.

In practice $2\tau$ is experimentally obtained from the pulse-echo time delay between the first front surface echo (FS) and substrate echo (BS) with the sample present. Either the time difference from FS peak location to BS peak location or cross-correlation of the waveforms of the two echoes can be used to obtain the $2\tau$ time delay. $\Delta t$ is the pulse-echo time difference between the echos off the reflector plate with (BS) and without (M") the sample present, respectively.

In fact, after the shuttle flight STS-114, the ability to nondestructively detect crushed foam became a significant priority. The microstructure-independent thickness mapping method can be used to identify and quantify areas of crushed (pushed-in) foam and precisely map thickness. The thickness-independent velocity method can be used to identify and quantify density variations in foam and other materials. It is worth noting that the previously-discussed ultrasonic methods for thickness-independent velocity and microstructure-independent thickness require water coupling while no such coupling is needed for terahertz methods. The latter fact makes the terahertz method much more practical than the ultrasonic method for dielectric materials.

Figure 3A:
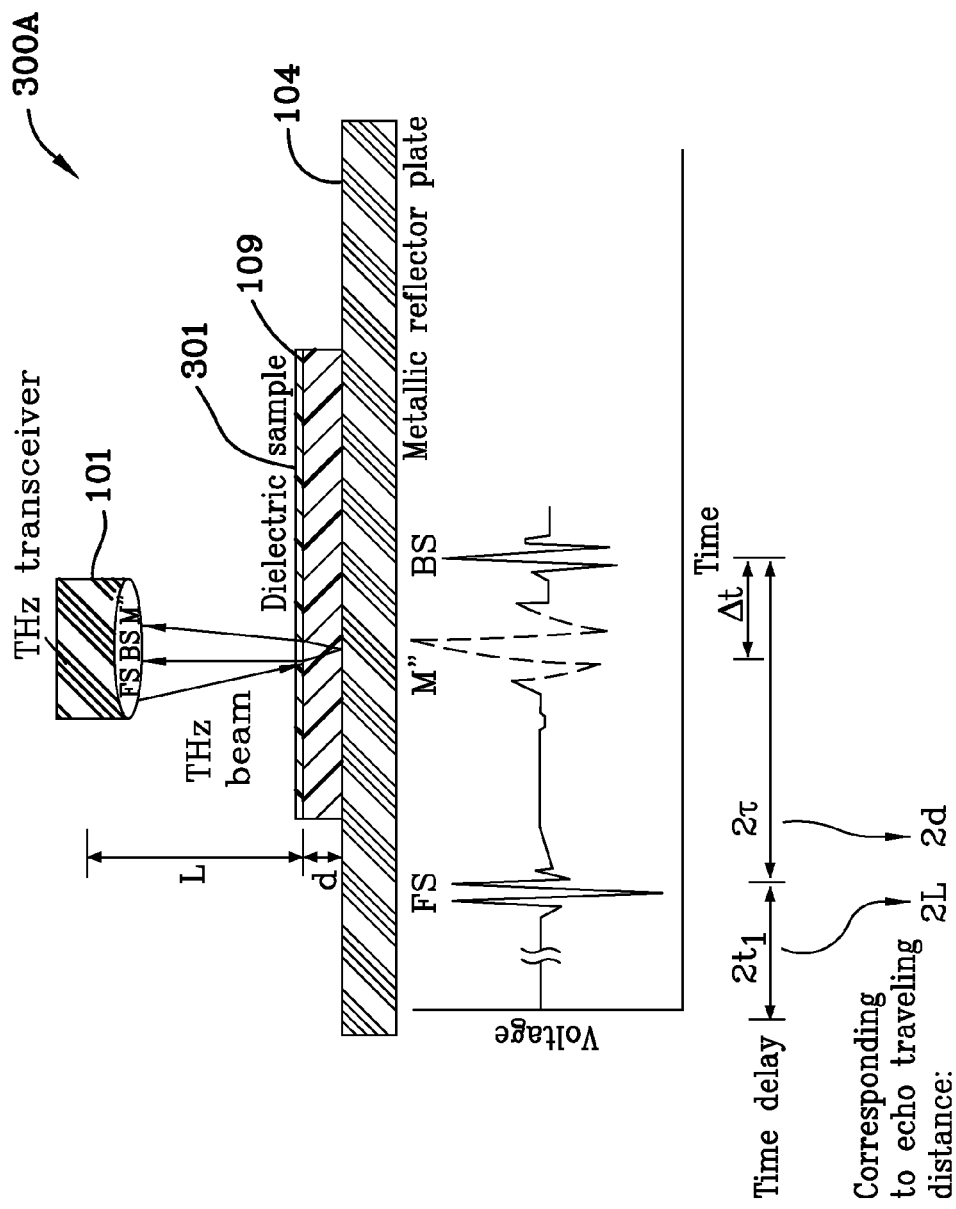
FIG. 3A illustrates a schematic similar to that illustrated in FIG. 3 with an additional thin dielectric material placed over the dielectric sample to create a dielectric mismatch.

The front surface echo (FS) from the dielectric material may be of very low signal-to-noise ratio (SNR) depending on the dielectric match between air and the sample. FIG. 3A illustrates a schematic similar to that illustrated in FIG. 3 with an additional thin dielectric material 301 placed over the dielectric sample to create a dielectric mismatch. If a good dielectric match exists, much of the terahertz energy will be transmitted into the sample and this presents somewhat of a problem. Additionally, the focal plane sensitivity of the terahertz method for samples of nonuniform thickness may result in the FS echo too far out of focus and thus reduce the signal to noise ratio (SNR) even further, thus limiting the thickness variation over which the method can be used. The approximate time location of the front surface echo (FS) off the dielectric sample must be known "a priori" and the wavetrain examined manually by an oscilloscope to determine special post-processing needs for amplification and denoising the front surface echo (FS). For the space shuttle external foam, the FS echo can be as small as $\frac{1}{100}$th the amplitude of the BS (back surface of the sample) echo. This requires signal processing/conditioning steps of denoising and/or low-pass (smoothing) filtering followed by amplification (software gain) at the time location(s) of the FS echo to clearly separate the FS echo from baseline noise.

As stated above, to create a better dielectric mismatch situation in which more of the terahertz energy is reflected back to the receiving system while an ample amount is still transmitted into the sample, a sheet of very thin (250 µm) plastic transparency paper 301 can be placed onto the sample. See, FIG. 3A. This method can be used to locate the front surface echo (FS) locations prior to scanning, or in situations where it can be tolerated during actual scanning, will provide front surface echos having much greater signal to noise ratios. Also, knowledge of the distance between scanner head and sample top surface, velocity of terahertz in air (speed of light), and any post- or pre-trigger delays should allow calculation of approximate front surface echo time location(s).

Figure 4:
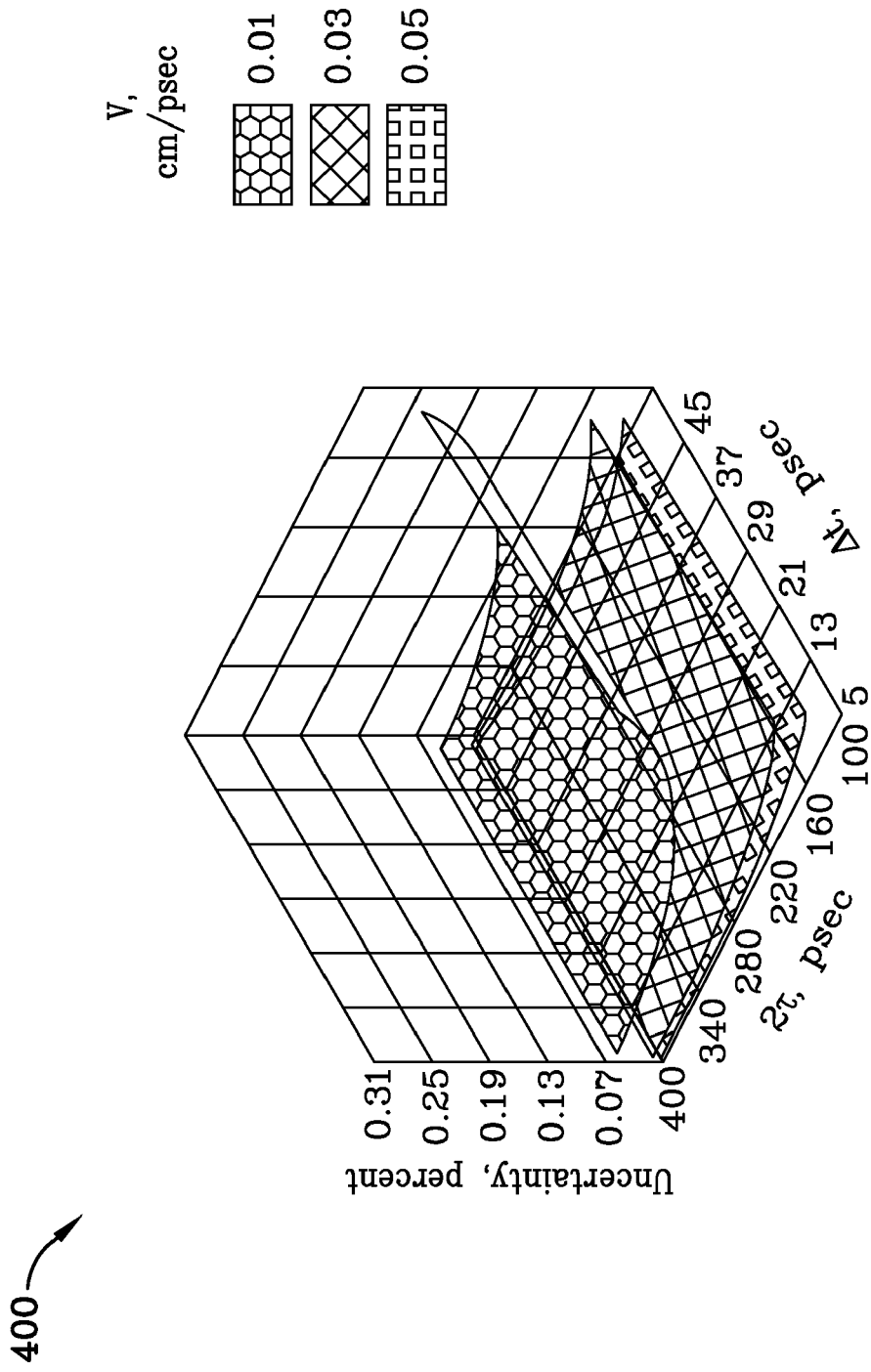
FIG. 4 is the uncertainty (in percentage) of the velocity (independent of the thickness) as a function of velocity, $2\tau$ and $\Delta t$.

FIG. 4 is a graph 400 of the uncertainty (in percentage) of the velocity (independent of the thickness) as a function of V (terahertz velocity in the material), $2\tau$ and $\Delta t$. The precision (uncertainty) in the thickness-independent velocity due to the random errors in the measurements of the variables $\Delta t$ and $2\tau$ was determined by the above equations and standard variance relation. Uncertainty in c was ignored and using typical values of $\Delta t \approx 6$ µsec, $2\tau=200$ psec, Sampling Rate=6.4 THz, c=0.02997055434 cm/psec, and V≈0.0290 cm/psec, gives Uv≈0.01 percent (uncertainty of the velocity in percent). FIG. 4 illustrates uncertainties (in percent) for three velocities, V, 0.01 cm/psec; 0.03 cm/psec; and, 0.05 cm/psec.

Figure 5:
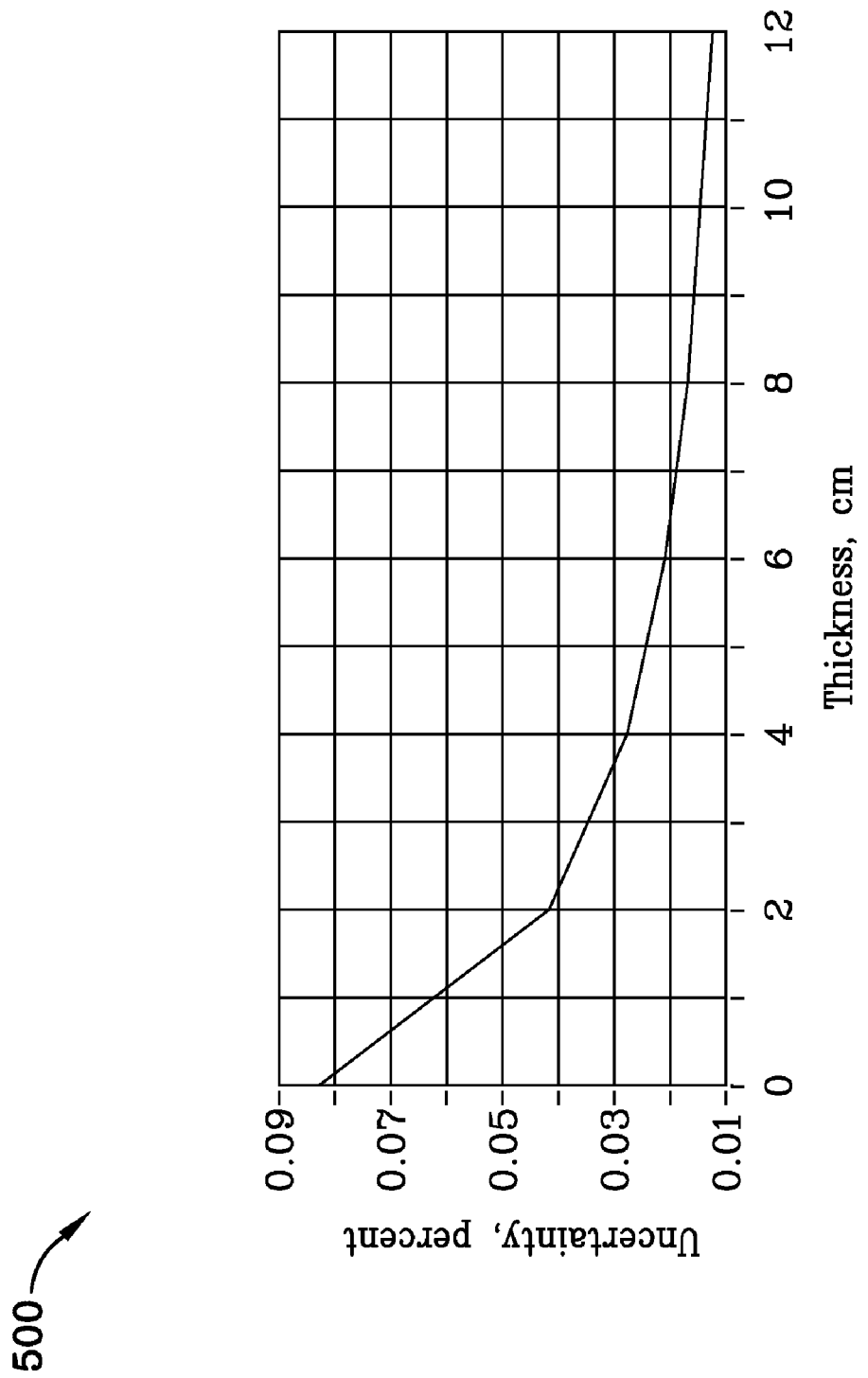
FIG. 5 is the uncertainty (in percentage) of the thickness (independent of the microstructural variations) as a function of thickness.

FIG. 5 is a graph 500 of the uncertainty (in percentage) of the thickness (independent of the microstructural variations) as a function of thickness, d. Similarly, the precision (uncertainty), Ud, of the thickness measurement is a function of the thickness as illustrated in FIG. 5. For the foam samples studied, and using typical values for SR=6.4 THz, c=0.02997055334 cm/psec, and thicknesses of approximately 3 to 5 cm, Ud=0.035 to 0.025 percent (uncertainty of the thickness in percent).

Figure 6:
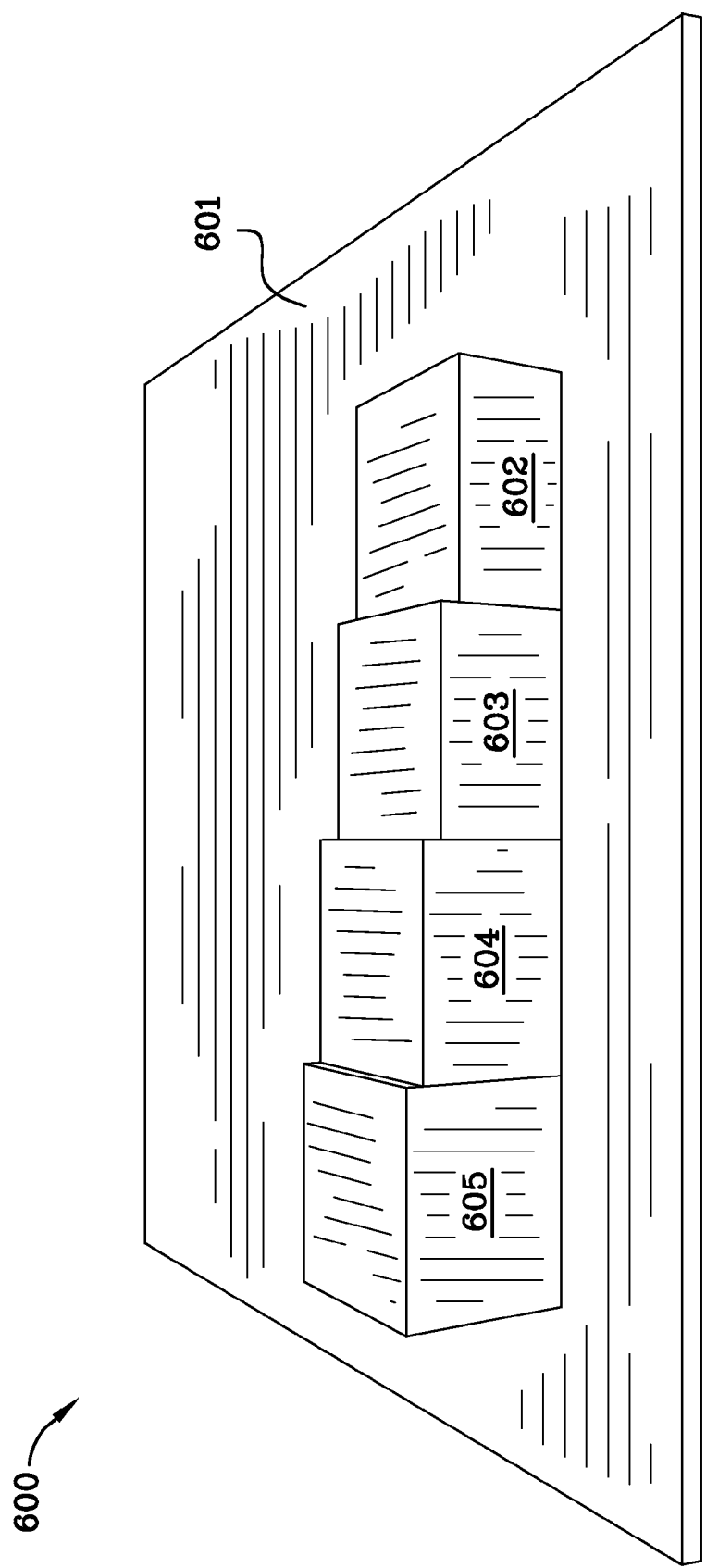
FIG. 6 is a perspective view of a foam block sample set on an aluminum plate.

FIG. 6 is a perspective view 600 of a foam block step wedge sample set on an aluminum plate 601. The first foam block 602, the second foam block 603, the third foam block 604, and the fourth foam block 605 are illustrated and arranged with increasing thickness and density from left to right. The foam block configuration of FIG. 6 is ordered as step wedges such that density and thickness variation results in an additive effect on $2\tau$.

FIG. 7 illustrates a composite image 700 of scans of the foam block sample set of FIG. 6 indicating $2\tau$ values of the foam blocks according to the methodology of the invention as a function of thickness and density. FIG. 7 shows $2\tau$, FIG. 7A shows microstructure-independent thickness image and FIG. 7B shows thickness-independent density image for the foam blocks of FIG. 6, using the novel terahertz method described in this invention. The density image was derived from thickness-independent velocity images using the relationship between terahertz velocity and density for foam shown in FIG. 2. This sample has well-defined thickness and density variation that have additive effects on the $2\tau$ image. It can be seen that the method is able to separate the thickness and density variation components as illustrated in FIGS. 7A and 7B.

FIG. 7A illustrates an image 700A of scans of the foam block sample set of FIG. 6 indicating thickness variations according to the methodology of the invention. FIG. 7B illustrates an image 700B of scans of the foam block sample set of FIG. 6 indicating density variations according to the methodology of the invention. The method of this invention separates thickness and density effects on time delay ($2\tau$) between FS and BS echos. Increasing thickness and increasing density from right-to-left in the blocks of FIG. 6 provides an additive effect in terms of increasing 2τ from right-to-left. Scan and/or analog-to-digital conversion jitter (zigzag gray level pattern) is apparent in the density image of FIG. 7B.

The terahertz experimental setup used in connection with the foam blocks of FIG. 6 was a broadband 1 THz scan system and included the following experimental and signal processing parameters:

Focus: (At substrate, or 3 cm above substrate for wedge samples)
Typical received bandwidth points (THz) (Full Width Half Max)≈0.1 to 0.3
Data Acquisition Rate (THz): 6.4
Waveform Length Acquired (psec/points): 320 psec/2048 points
Waveform Acquisition Rate (scan points/sec): ≈10
Collinear source-detector: Yes
Spatial Resolution (at Full Width Half Max of Point Spread Function): 0.5 cm
Signal Acquisition Width of dynamic (peak-centered) gates for time delay computations (psec): 25 to 100 psec
Scan Increment (cm): 0.2

Samples were placed on an aluminum plate as shown in FIG. 6 and scanned with scan increments in the X and Y direction of 0.2 cm. The minimum number of scans required to obtain thickness-independent velocity and microstructure-independent thickness is two. One scan obtains FS and BS echos (with sample present) and the second scan obtains the M" echo (without sample present). Separate scans for FS and BS can be performed if sample thickness is too large to allow simultaneous capture of both of the echos in the 320 psec/2048 point window using the 6.4 THz sampling rate. Only two scans were required when the thicknesses were <4 cm and FS and BS could be captured in one scan. For each sample set, the scans were then fused (combined using software) such that FS, BS and M" echos were placed in a single wavetrain of 640 psec/4096 points length with time relationships between the echos preserved. This occurs at each scan location to create the new fused data set. Precise time delays 2τ and Δt were determined using cross-correlation between the echos' waveforms. Phase relationships were examined for: (1) FS compared to BS; and, (2) BS compared to M". All waves appeared to be in phase for the analysis made. If echos are in-phase with respect to each other, the time occurrence of the maximum in the correlation function was used to calculate time delay. If the echos were phase-inverted, the time occurrence of the minimum in the correlation function should be used to calculate time delays.

Figure 15:
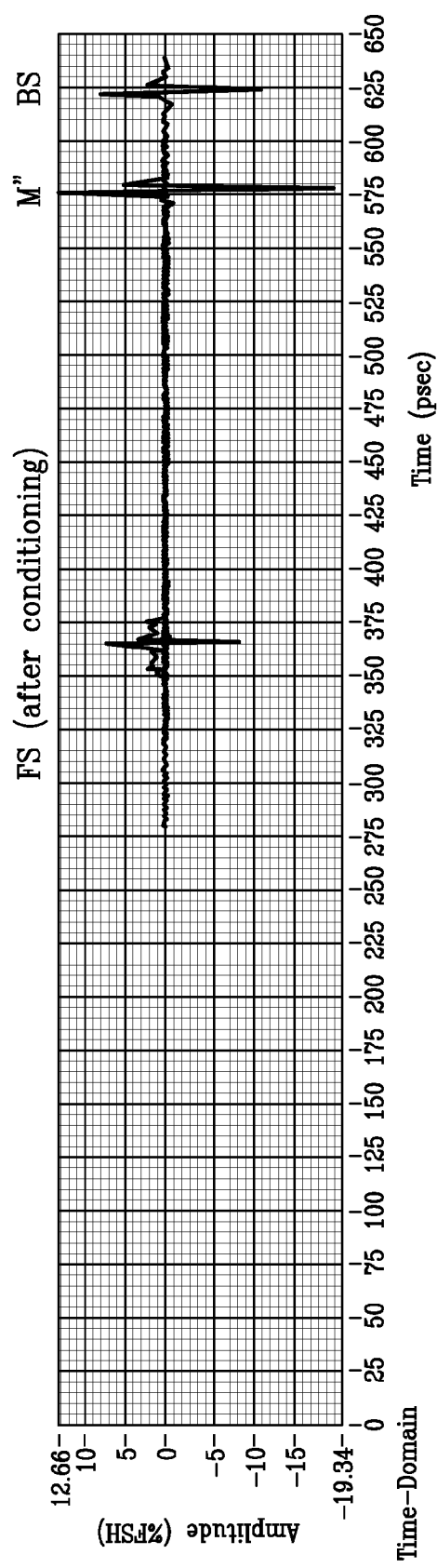
FIG. 15 is a typical "fused" waveform from a "fused" data file produced by merging the FS, BS, and M" scan data sets for a set of foam blocks.

A typical "fused" waveform from a "fused" data file is illustrated in FIG. 15. FIG. 15 is a typical "fused" waveform 1500 from a "fused" data file produced by merging the FS, BS, and M" scan data sets for a set of foam blocks.

The fused data file is produced by merging the FS, BS, and M" scan data sets for foam block sets. FS and BS occur with the sample present. M" occurs without the sample present. For visualization purposes, M" has been artificially shifted to the left an additional 40 psec in FIG. 15 to avoid overlap between the echoes. FS has been denoised, amplified, and a DC component has been subtracted therefrom so as to allow 2τ time delay calculation. A 25 to 100 psec gate (window) was applied to account for variations in FS echo position due to thickness variations in the sample. The gated region containing the FS echo was denoised using a wavelet process, then amplified by 10 to 40×, followed by subtraction of the DC component. The denoising process used the debauchies 05 mother wavelet principle. The resultant FS echo was quite useable as shown in FIG. 15. Two Tau (2τ) and Δt are determined using the fusing process and the entire waveforms are either cross-correlated or the peaks are precisely identified enabling the measurement of the time between them. A computer process with an appropriate algorithm is used to calculate 2τ and Δt.

Figure 16:
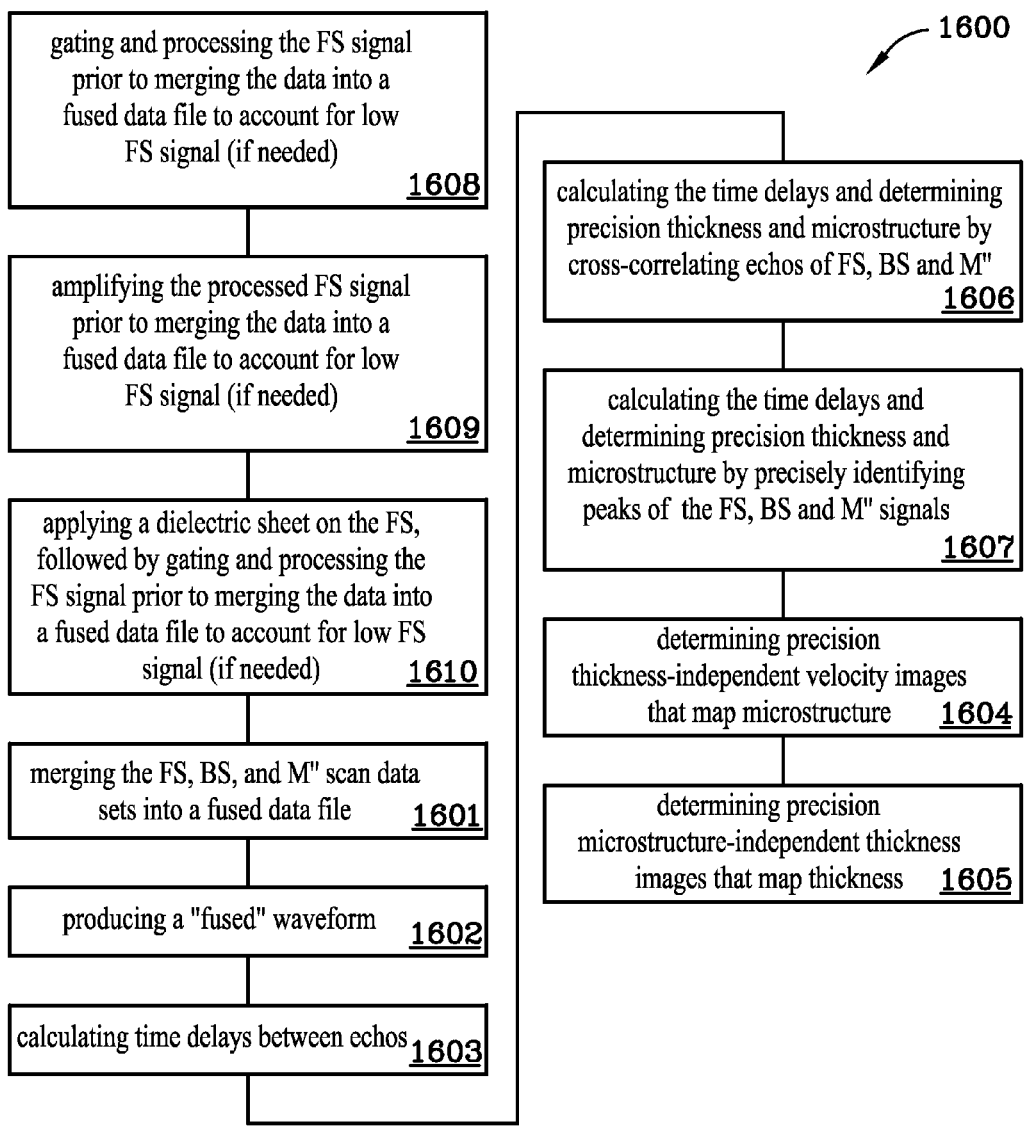
FIG. 16 is a schematic of a process (another example) for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample, the sample residing on a substrate.

FIG. 16 is a schematic 1600 of another process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample. The process includes the steps of: merging the FS, BS, and M" scan data sets into a fused data file 1601; producing a "fused" waveform 1602; calculating time delays between echos 1603; determining precision thickness-independent velocity images that map microstructure 1604; and, determining precision microstructure-independent thickness images that map thickness 1605. The steps of calculating the time delays and determining precision thickness and microstructure are performed by the step of cross-correlating the entire waveform of FS, BS and M" 1606. Alternatively, the steps of calculating the time delays and determining precision thickness and microstructure are performed by precisely identifying peaks of FS, BS and M" signals 1607.

If a poor dielectric mismatch occurs between the air and the sample, the step of gating and processing the FS signal prior to merging the data into a fused data file 1608 is performed. If the signal to noise ratio is low then the step of amplifying the processed FS signal prior to merging the data into a fused data file 1609 is performed. Further the step of applying a dielectric sheet on the FS, followed by gating and processing the FS signal prior to merging the data into a fused data file 1610 may optionally be performed to enhance the signal processing.

FIG. 8 illustrates 800 a physically-measured density map in grams per cubic centimeters for a 6 by 15 set of foam blocks with non regular thickness and density. The set of 6 by 15 foam blocks had dimensions of about 5 by 5 by 5 cm, with minor but non regular thickness variation (±0.1 cm). The blocks were of various densities ranging from about 0.042 to 0.054 g/cm$^3$ "(on the order of 20 percent)" measured from mass and dimensional measurements and were arranged randomly. FIG. 8A illustrates 800A the density by shade of gray in grams per cubic centimeter for the physically-measured density map shown in FIG. 8. FIG. 9 illustrates a terahertz density map 900 for the same 6 by 15 set of foam blocks derived from the velocity variations (determined independently of thickness) according to the methodology of the invention using the relationship between terahertz velocity and density for foam shown in FIG. 2. FIG. 9A illustrates 900A the density by shade of gray in grams per cubic centimeter for the derived terahertz density map shown in FIG. 9.

Reference numeral 801 represents an area of the physically measured density map and reference numeral 901 represents an area of the mapped terahertz density plot for the same set of foam blocks. Reference numeral 802 represents an area of the physically-measured density shown in FIG. 8 of the set of foam blocks and reference numeral 902 represents an area of the mapped terahertz density plot for the same set of foam blocks. Viewing lighter and darker areas (801, 901, 802, 902) in the images of FIGS. 8 and 9, it is clear that the physically-measured density variation agrees quite closely with that derived from the thickness-independent velocity.

FIG. 10 illustrates a hand-measured thickness map 1000 in centimeters for the same 6 by 15 set of foam blocks. FIG. 11 illustrates a terahertz thickness image 1100 for the 6 by 15 set of foam blocks (determined independently of velocity) according to the methodology of the invention. FIG. 10A illustrates the thickness in centimeters by shade of gray in a bar graph 1000A. FIG. 11A illustrates the thickness 1100A by shade of gray in centimeters for the terahertz thickness map of FIG. 11. As stated previously the blocks vary in thickness from 5 cm by ±0.1 cm. Reference numeral 1001 is an ellipse indicating an area of the hand measured thickness map to be compared to a terahertz thickness map and reference numeral 1101 is an ellipse indicating an area of the terahertz thickness map to be compared to a physically measured thickness map. Note the excellent correlation between dark and light areas in both images. Ellipses 1001 and 1101 denote the identical area under examination. Good correlation within ellipses 1001 and 1101 between light and dark areas is observable. Dark scatter spots in the terahertz generated thickness are due to the presence of an additional echo within the signal processing gate that results in improper cross-correlation delay calculation. This additional echo is likely due to the presence of extra material on the surface. These scatter spots are also in the thickness-independent velocity image of FIG. 9 but blend in better as they cause variation in that image in the same "direction" as actual velocity variations.

Figure 12:
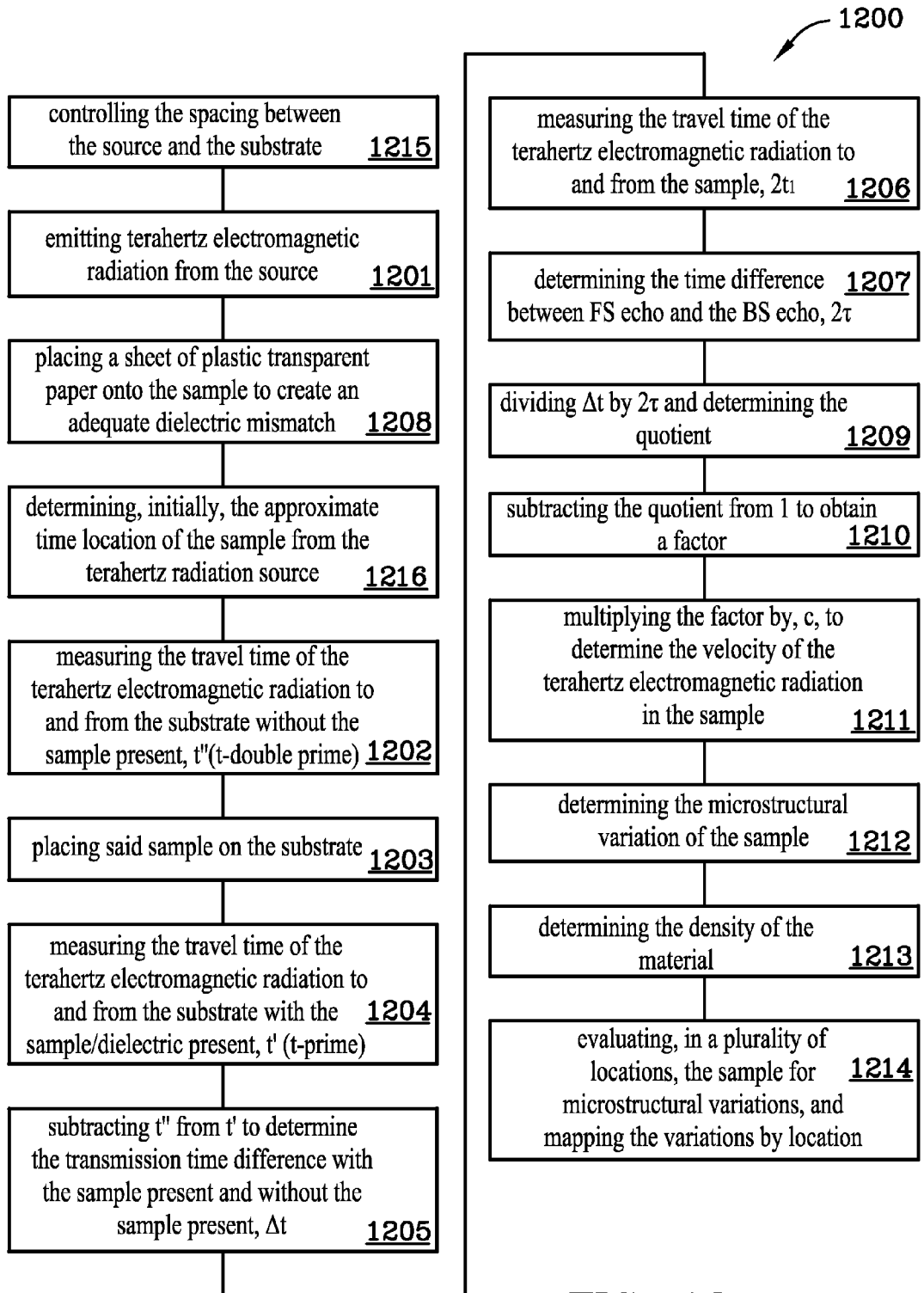
FIG. 12 is a schematic diagram of a process for measuring the velocity of terahertz electromagnetic radiation in a material sample without prior knowledge of the thickness of the sample, the terahertz electromagnetic radiation produced by a source (transceiver) spaced apart from the sample under test and propagated at the speed of light, c, in a medium located between the source (transceiver) and the sample, the sample residing on a substrate.

FIG. 12 is a schematic diagram 1200 of a process for measuring the velocity of terahertz electromagnetic radiation in a material sample without prior knowledge of the thickness of the sample, the terahertz electromagnetic radiation produced by a source (transceiver) spaced apart from the sample under test and propagated at the speed of light, c, in a medium located between the source and the sample. The steps of the process may be performed in any desired or necessary order. The process includes the steps of: emitting pulsed terahertz electromagnetic radiation from the source 1201 (the radiation may be pulsed or it may be continuous); measuring the travel time of the terahertz electromagnetic radiation to and from the substrate without the sample present, t" (t-double prime), 1202; placing the sample on the substrate 1203; measuring the travel time of the terahertz electromagnetic radiation to and from the substrate with the sample/dielectric present, t' (t-prime) 1204; subtracting t" from t' to determine the transmission time difference with the sample present and without the sample present, $\Delta t$, 1205; measuring the travel time of the terahertz electromagnetic radiation to and from the sample, $2t_1$, 1206; determining the time difference between the FS echo and the BS echo, $2\tau$, 1207; placing a sheet of plastic transparent paper onto the sample to create an adequate dielectric mismatch 1208; dividing $\Delta t$ by $2\tau$ and determining the quotient 1209; subtracting the quotient from 1 to obtain a factor 1210; multiplying the factor by, c, to determine the velocity of the terahertz electromagnetic radiation in the sample 1211; determining the microstructural variation of the sample 1212; determining the density of the material 1213; evaluating, in a plurality of locations, the sample for microstructural variations; and mapping the variations by location 1214; controlling the spacing between the source and the substrate 1215; and, determining, initially, the approximate time location of the sample from the terahertz radiation source 1216. Additionally, the step of determining the microstructual variation of the sample may include the determination of a parameter other than density. In the case of a poor dielectric mismatch between the air and the sample to be inspected, the process can include a step of placing a sheet of plastic transparent paper onto the sample to create an adequate dielectric mismatch.

Figure 13:
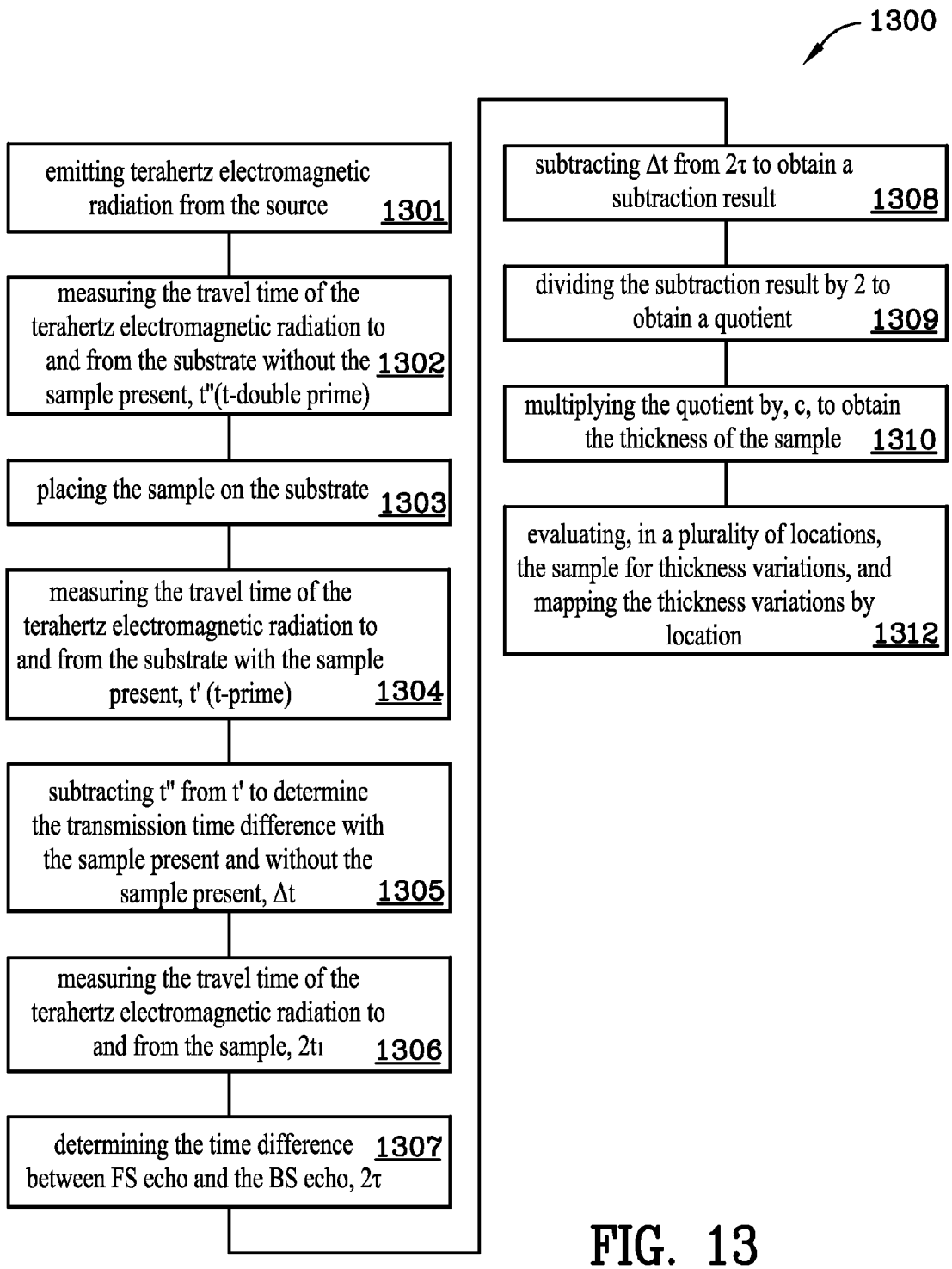
FIG. 13 is a schematic diagram of a process for measuring the thickness of a material sample using terahertz electromagnetic radiation in a material sample without prior knowledge of the velocity of the terahertz electromagnetic radiation in the sample, the terahertz electromagnetic radiation produced by a source (transceiver) spaced apart from the sample under test and propagated at the speed of light, c, in a medium located between the source (transceiver) and the sample, the sample residing on a substrate.

FIG. 13 is a schematic diagram 1300 of a process for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample. The process for measuring the thickness using terahertz electromagnetic radiation includes: emitting terahertz electromagnetic radiation from the source 1301 (the radiation may be pulsed or it may be continuous); measuring the travel time of the terahertz electromagnetic radiation to and from the substrate without the sample present, t" (t-prime), 1302; placing the sample on the substrate 1303; measuring the travel time of the terahertz electromagnetic radiation to and from the substrate with the sample present, t'(t-prime), 1304; subtracting t" from t' to determine the transmission time difference with the sample present and without the sample present, $\Delta t$, 1305; measuring the travel time of the terahertz electromagnetic radiation to and from the sample, $2t_1$, 1306; determining the time difference between the FS echo and the BS echo, $2\tau$, 1307; subtracting $\Delta t$ from $2\tau$ to obtain a subtraction result 1308; dividing the subtraction result by 2 to obtain a quotient 1309; multiplying the quotient by, c, to obtain the thickness of the sample 1310; and, evaluating, in a plurality of locations, the sample for thickness variations; and mapping the thickness variations by location 1312.

Figure 14:
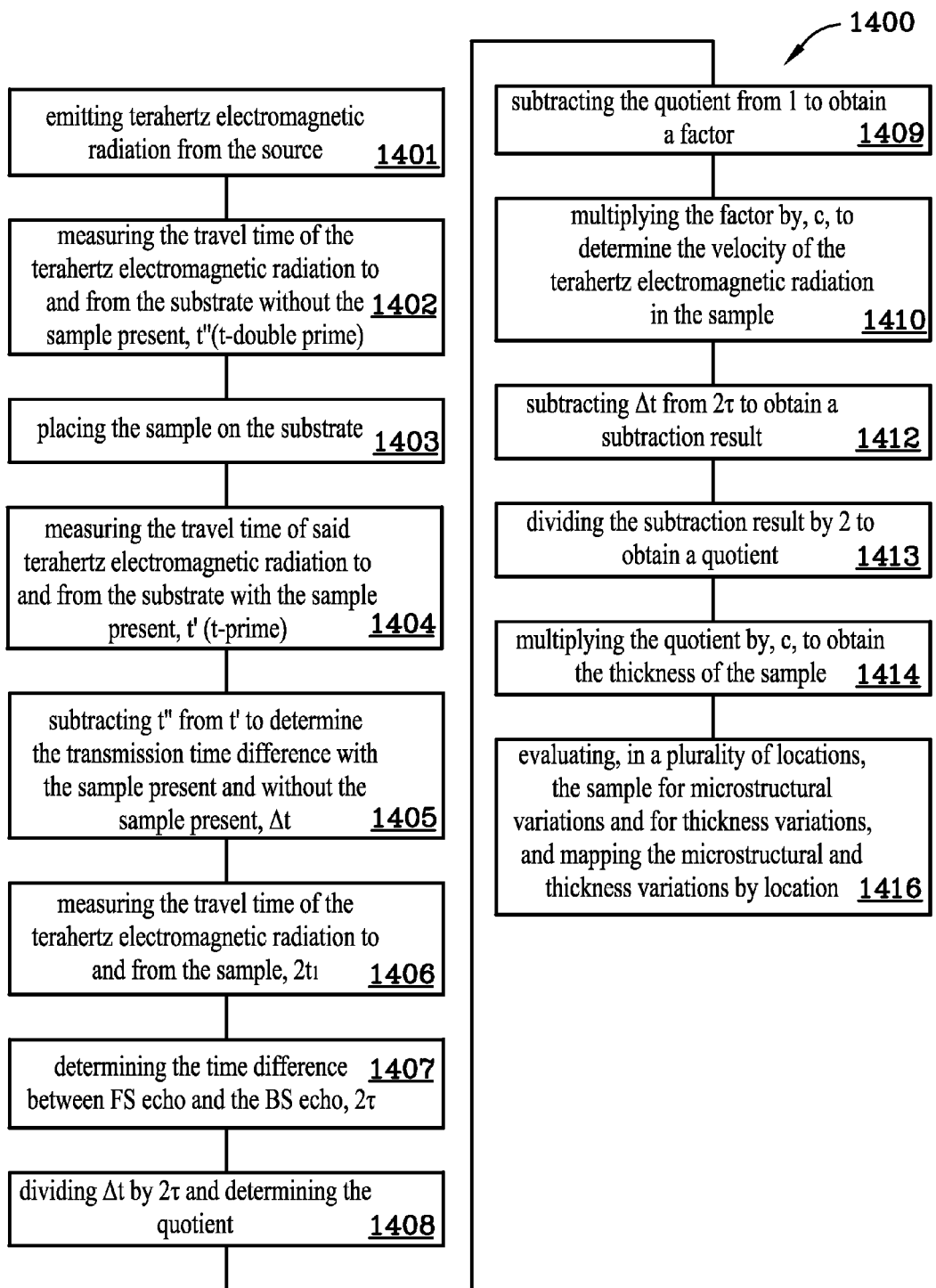
FIG. 14 is a schematic of a process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source (transceiver) spaced apart from the sample under test and propagated at the speed of light, c, in a medium located between the source (transceiver) and the sample, the sample residing on a substrate.

FIG. 14 is a schematic 1400 of a process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample. The process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample includes the steps of: emitting terahertz electromagnetic radiation from the source 1401 (the radiation may be pulsed or it may be continuous); measuring the travel time of the terahertz electromagnetic radiation to and from the substrate without the sample present, t" (t-double prime) 1402; placing the sample on the substrate 1403; measuring the travel time of the terahertz electromagnetic radiation to and from the substrate with the sample present, t' (t-prime) 1404; subtracting t" from t' to determine the transmission time difference with the sample present and without the sample present, $\Delta t$, 1405; measuring the travel time of the terahertz electromagnetic radiation to and from the sample, $2t_1$lain, 1406; determining the time difference between the FS echo and the BS echo, $2\tau$, 1407; dividing $\Delta t$ by $2\tau$ and determining the quotient 1408; subtracting the quotient from 1 to obtain a factor 1409; multiplying the factor by, c, to determine the velocity of the terahertz electromagnetic radiation in the sample 1410; subtracting $\Delta t$ from $2\tau$ to obtain a subtraction result 1412; dividing the subtraction result by 2 to obtain a quotient 1413; multiplying the quotient by, c, to obtain the thickness of the sample 1414; and, evaluating, in a plurality of locations, the sample for microstructural variations and for thickness variations, and mapping the microstructural and thickness variations by location 1416.

Operation of the computer interface (NDE Wave And Image Processor) to create fused files, determine and store data files, and output velocity/density images and thickness images is as follows:

Creating a Fused File

Figure 20:
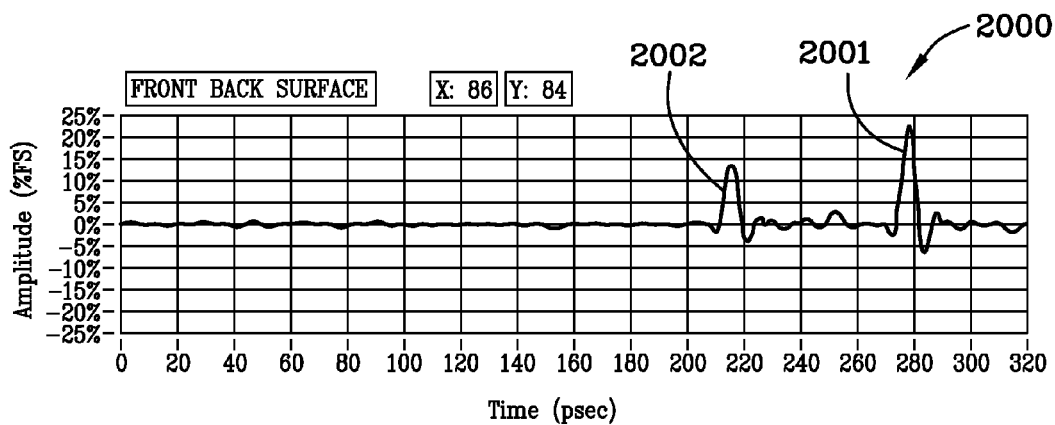
FIG. 20 is an oscilloscope-like trace of a front surface (FS) echo waveform and a back surface (BS) echo waveform for the x=86, y=84 scan point coordinate.
Figure 20A:
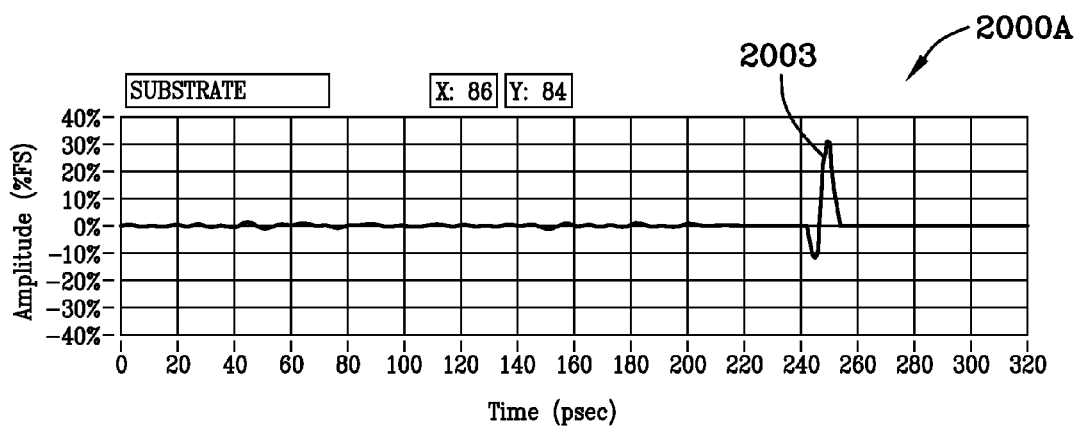
FIG. 20A is an oscilloscope-like trace of a substrate echo (M") waveform for the x=86, y=84 scan point coordinate.
Figure 20B:
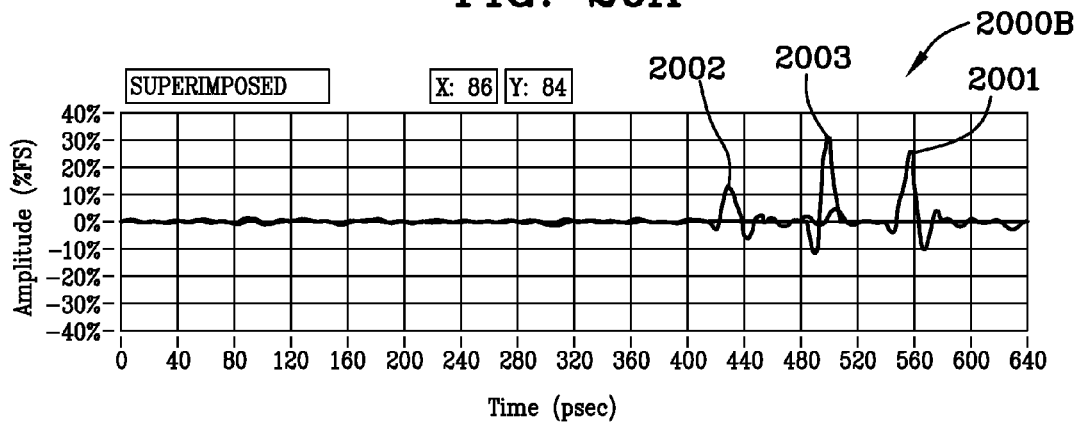
FIG. 20B is an oscilloscope-like trace of the front surface (FS) echo waveform and the substrate echo (M") waveform superimposed into the back surface (BS) echo waveform for the x=86, y=84 scan point coordinate.

A computer program for use with a computer and computer display has be created using LabVIEW® software. First, the user must select a stored waveform file to open from an opening dialog box in the NDE Wave and Image Process program opening screen. Open a back surface file when prompted to open waveform file. The underlying code of this interface uses LabVIEW® functions for the interface, code for dialog box, and basic LabVIEW® functions for opening a file, and parsing information from binary files. LabVIEW® is a registered trademark of National Instruments. Upon opening a file, a peak-to-peak amplitude image is created and shown in an image container and the waveform associated with the center point of the scan is shown in the time-domain graph. FIG. 20 illustrates a front surface (FS) echo waveform and a back surface echo waveform. FIG. 20D illustrates image windows for superimposed files.

Next, in the menu, click on density/thickness study, under the miscellaneous menu. After "density/thickness study" is selected, controls will appear on the main window in the area where the image container was and the image container box disappears. The user is then prompted to open the three files containing echoes to be fused, the first of which is back surface file which was previously opened. The user then designates the substrate echo (M") and front surface (FS) echo files next, and then the user selects "ok" to superimpose the files on the same oscilloscope-like trace. The back surface (BS) echo file and front surface (FS) echo files might actually be the same files but both files have to be entered into the respective dialog boxes when prompted to do so. The program prompts the user to enter a new file name.

This file will consist of the three echoes fused together and needed for thickness-independent velocity and microstructure-independent thickness. A new file is created and three files are superimposed in an oscilloscope trace and might look something like that shown by way of example in FIG. 20B. The echo files are not yet fused into a new file at this point but are superimposed on the same trace as the waveforms in the three files are recalled and positioned appropriately for visualization. See, FIG. 20B.

The following steps result in actual fusing of the echoes into one file. The software prompts the user to interactively select "gate" and then select "multigate" under gate type menu. Adjust substrate echo offset delay as needed to space it away from the back surface echo. FIG. 20G illustrates an interactive selection of the time shift for the substrate echo (M") waveforms to place it away from the back surface (BS) echo wave prior to gating and fusing the waveforms together. Substrate echo will have higher amplitude than back surface echo. Generally, add (−) delay so as to move the substrate echo to the left away from the back surface echo. Referring to FIG. 20H, the user places gate 1, 2013, centered over the substrate echo (M") waveform 2013, and then mouse clicks the "Add Gate" button. The user then places gate 2, 2012, to the time location where front surface (FS) echo waveform is; apply digital filtering, wavelet denoising, and wavelet reconstruction as needed, adjust FS gate amplification factor, Z-axis move distance if refocusing on FS occurred (+value), as needed. See FIGS. 2000H and I. Once gate 2, 2012, is placed the user mouse clicks "Add Gate" button. See FIGS. 20G and 20I wherein the user of the software is prompted to select boolean buttons for signal conditioning the front surface (FS) echo waveform/signal. The front surface (FS) echo waveform may be in need of conditioning as it is sometimes a weak signal if the dielectric mismatch is not significant.

Modify c (cm/sec) depending on whether experimental conditions are for electromagnetic waves in air or ultrasound in water. If the front surface (FS) echo waveform is very weak, first you must know approximate time location of FS echo in FS file since amplitude is almost in the noise and you need to properly gate.

Figure 20C:
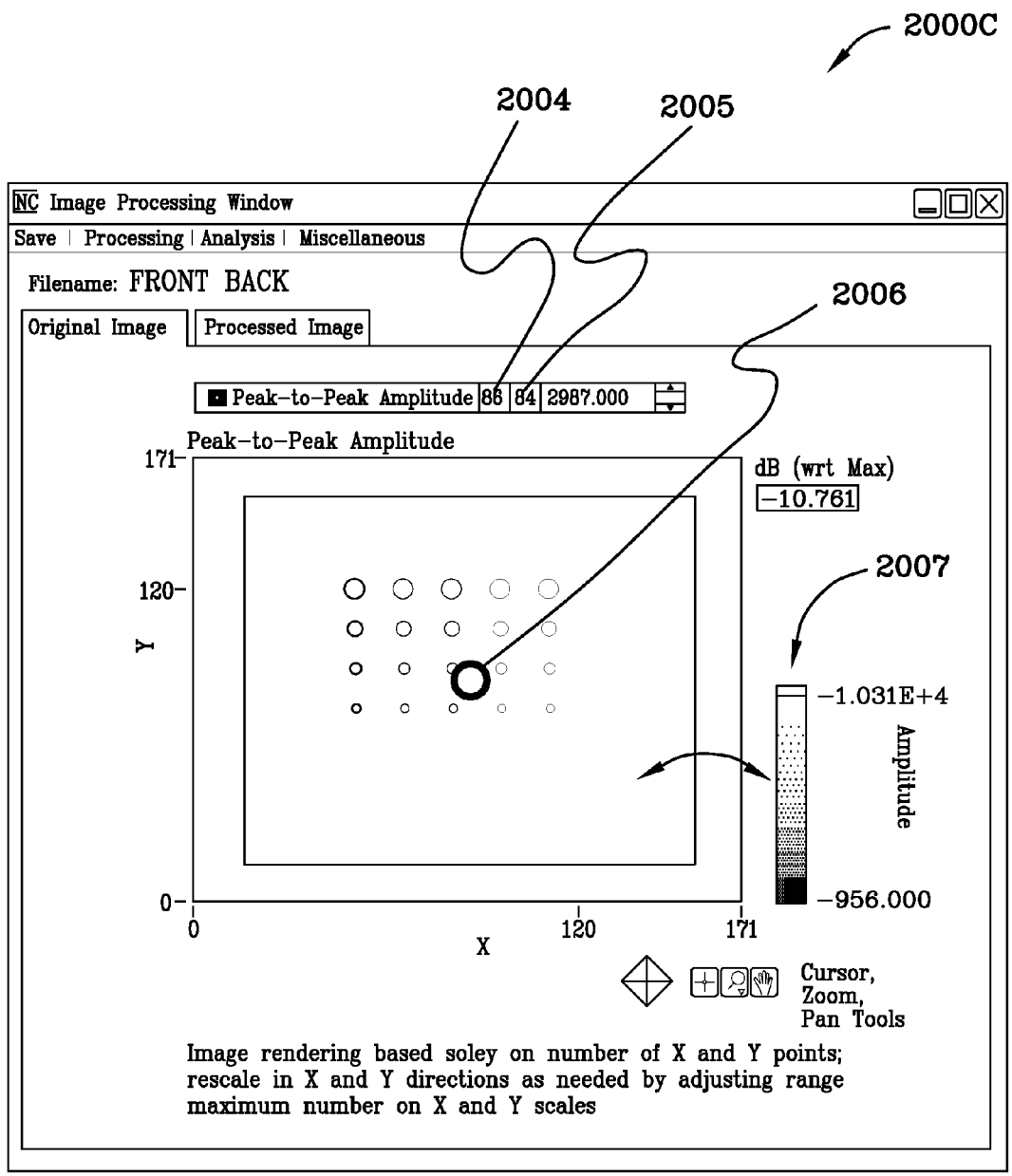
FIG. 20C is an image of the back surface (BS) echo waveform illustrating the x-y scan points ranging from x=171 to y=171 allowing the user to canvas any of the scan points to produce superimposed files having the front surface (FS) echo waveform, the substrate echo (M") waveform superimposed into and onto the back surface (BS) echo waveform.
Figure 20D:
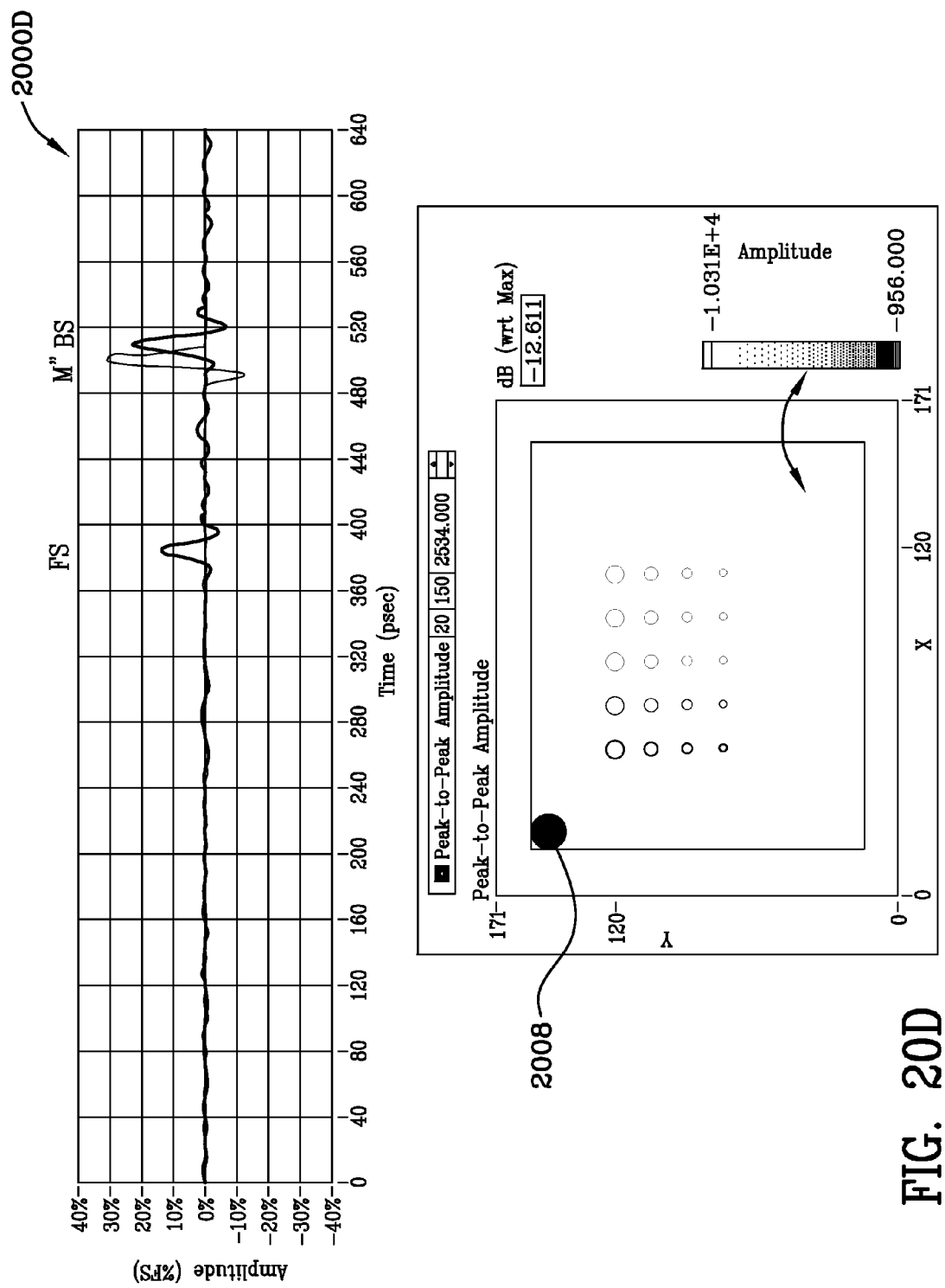
FIG. 20D is an image of the superimposed file for scan coordinates of x=20, y=150 and the corresponding oscilloscope-like trace of the superimposed files having the front surface (FS) echo waveform, the substrate echo (M") waveform superimposed into and onto the back surface (BS) echo waveform.
Figure 20E:
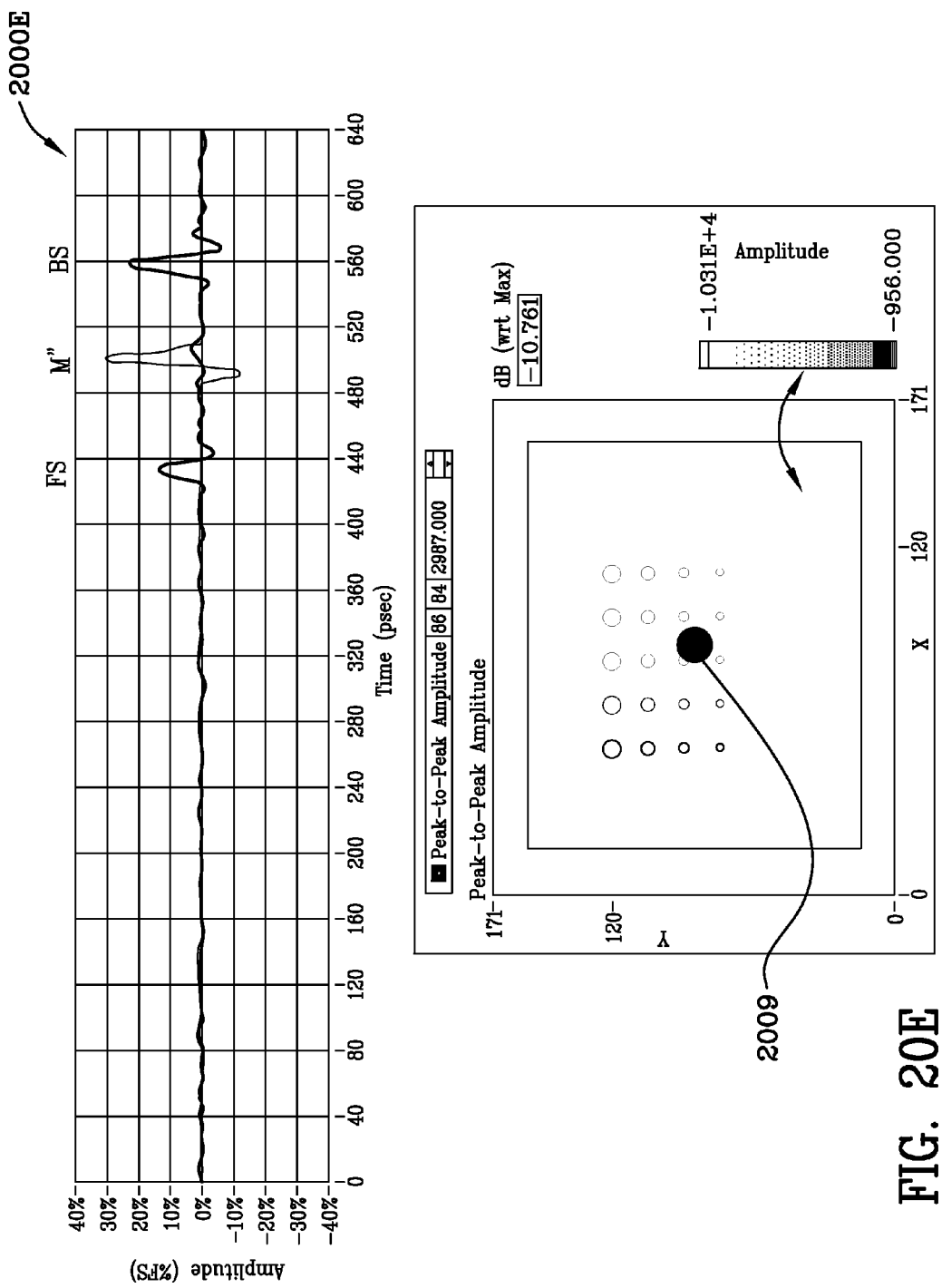
FIG. 20E is an image of the superimposed file for scan coordinates of x=86, y=84 and the corresponding oscilloscope-like trace of the superimposed files having the front surface (FS) echo waveform, the substrate echo (M") waveform superimposed into and onto the back surface (BS) echo waveform.
Figure 20F:
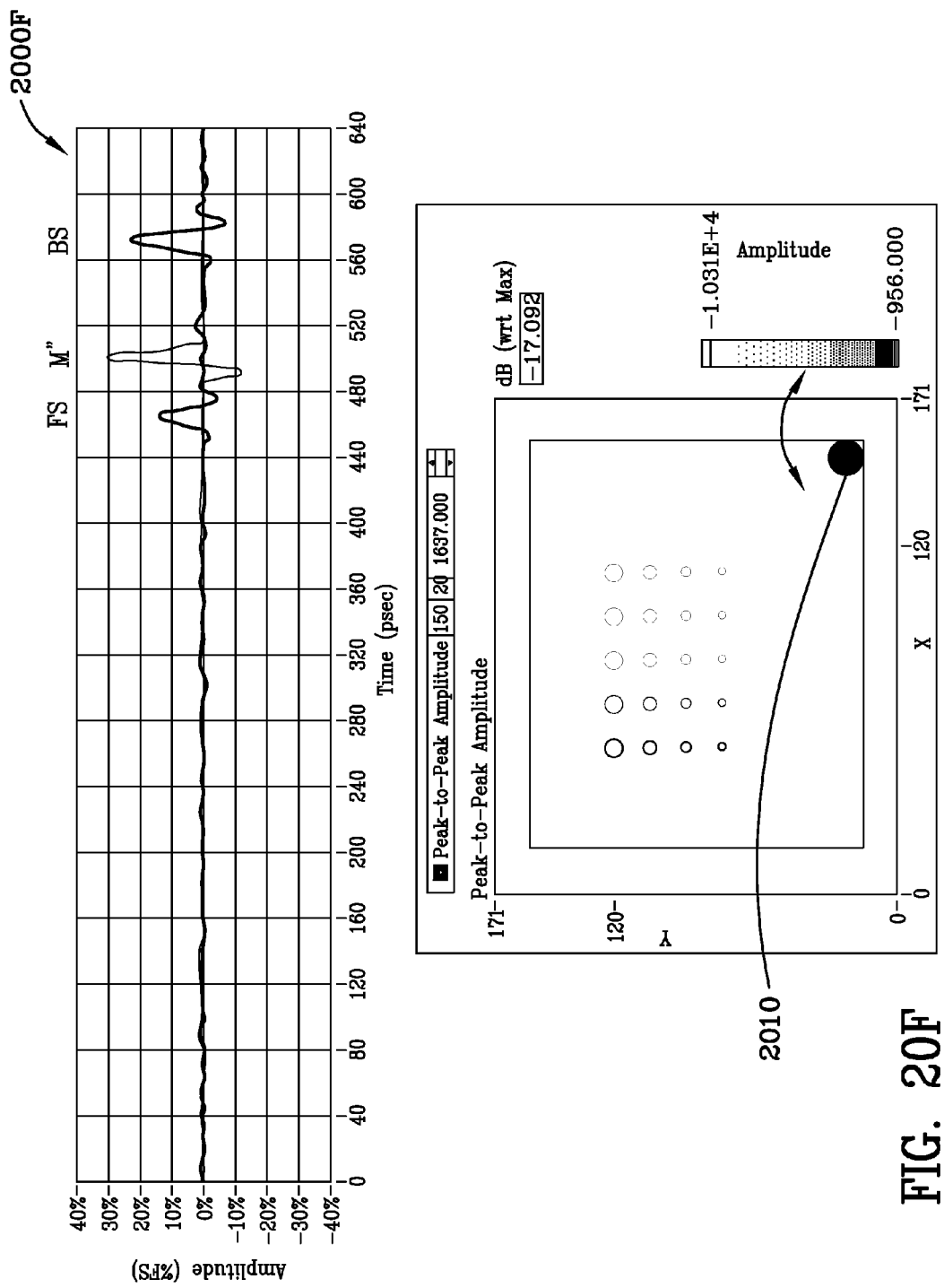
FIG. 20F is an image of the superimposed file for scan coordinates of x=150, y=20 and the corresponding oscilloscope-like trace of the superimposed files having the front surface (FS) echo waveform, the substrate echo (M") waveform superimposed into and onto the back surface (BS) echo waveform.
Figure 20G:
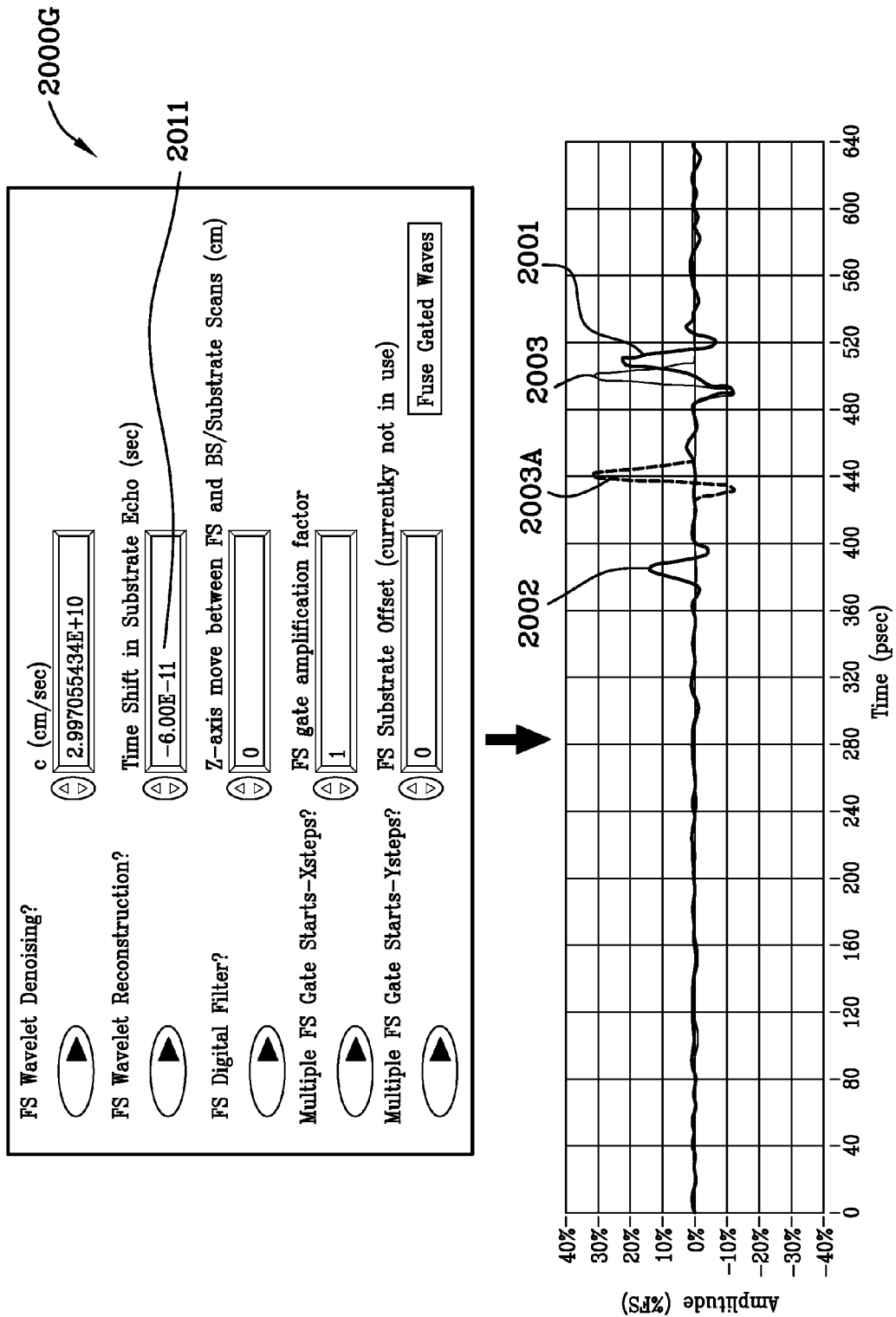
FIG. 20G is a screen shot from the software program implementing signal condition of the front surface (FS) echo waveform and delaying, by a specified amount of time, the substrate echo (M") waveform to facilitate gating of the substrate echo (M") waveform.
Figure 20H:
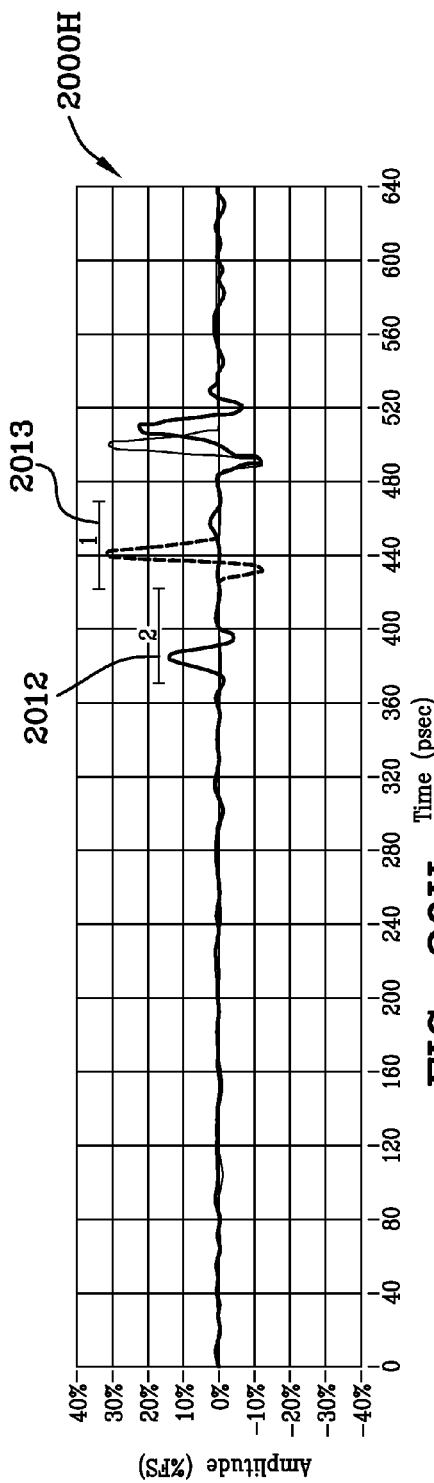
FIG. 20H is an oscilloscope-like trace of the time shifted substrate echo (M") waveform and gating of the front surface (FS) echo waveform and the time shifted substrate (M") waveform.
Figure 20I:
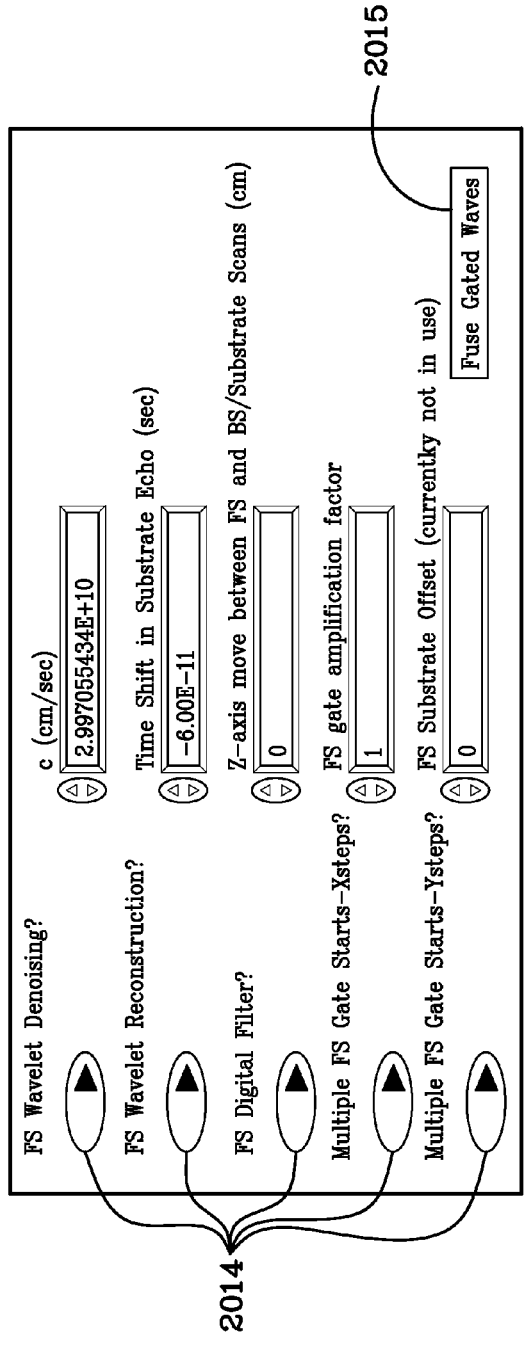
FIG. 20I is a screen shot similar to FIG. 20G from the software program implementing signal condition of the front surface (FS) echo waveform and delaying, by a specified amount of time, the substrate echo (M") waveform to facilitate gating of the substrate echo (M") waveform and in addition indicating the "fuse gated waves" boolean button.

The user then mouse clicks "Fuse Gated Waves," 2015, FIG. 20I, which will place substrate echo (M") waveform and front surface echo (FS) waveform into the back surface (BS) echo waveform or wavetrain that has been expanded to double the size of the original wavetrain (egs. original=2048 (320 psec), fused=4096 points (640 psec)). The code for fusing involves opening the three files and assembling the echoes using proper timing information and expanding the total number of positions in the waveform to twice the length of the individual waveform.

Instruction for using the fused files follows.

The software produces an image processing window when the file fusing procedure is completed and it will contain a peak-to-peak image. The cursor may be moved across the image processing window to recall the superimposed waves as needed. In effect, the user is canvassing areas of the sample to view the fused files for information as the range for later gating of the files. The time arrangement between substrate echo wave form (M") and back surface (BS) echo waveform will depend on whether evaluation involves electro-magnetic waves in air or ultrasound in water. For waves in air, the substrate echo M" waveform is always expected to occur earlier in time as the speed of light in air will be faster than that through a material.

The next step includes opening a fused echo waveforms file containing fused waveforms for each scan point. Using the mouse, the user clicks on the image container window to spawn the image processing window. The waveforms in the time-domain graph in the main window should now have three distinct echoes based on the original gating of the front surface echo (FS) waveform and the substrate echo (M") waveform to form the fused file. An oscilloscope trace is displayed and should look something like FIG. 20J after fusion. The user can move and release a cursor in the image processing window to recall fused waveforms at any scan point.

Gates are now used again and the selection "use gate" should be made as should the selection "multigate" under gate type menu. Two gates should be placed as follows: gate1, 2017, is placed on the front surface (FS) waveform echo and gate 2, 2018, is placed on the back surface (BS) waveform echo. See FIG. 20K. Form the delay image, an image of 2τ, between gates 1 and 2 ("peak to peak", or "cross correlation") under Form Image of Type/Calculate Time Domain Velocity-Thickness menus. If multiple front surface (FS) waveform times were gated during file fuse procedure, the front surface (FS) waveform gate (gate 1, 2017) should be made as long as needed to cover the movement of the front surface (FS) waveform echo determined by canvassing the waveforms in FIGS. 20D-20F. Then the image should be saved as a .bin or .txt file. Saving as .txt or .bin file is done using basic Lab VIEW functions. ".bin" files are binary files and ".txt" files are text files and can be opened by spreadsheet programs to view outside of the Lab View program.

Figure 20J:
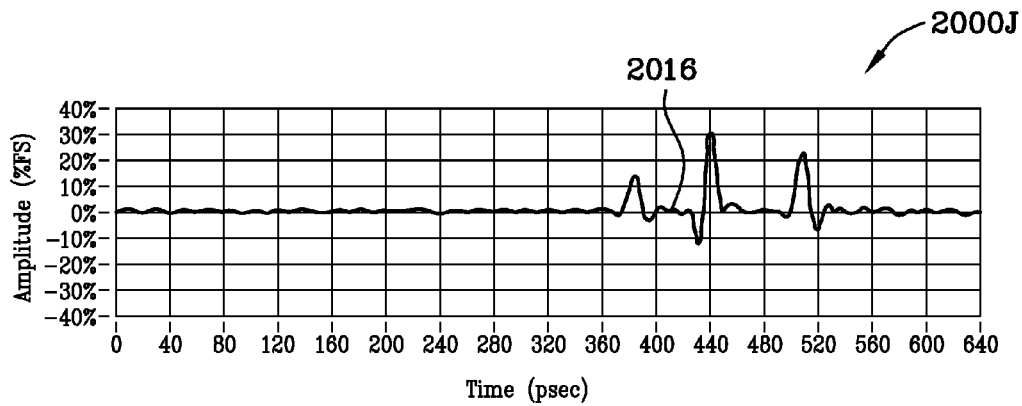
FIG. 20J is an oscilloscope-like trace of the fused waveform containing the front surface (FS) echo, the substrate echo (M") and the back surface (BS) echo.
Figure 20K:
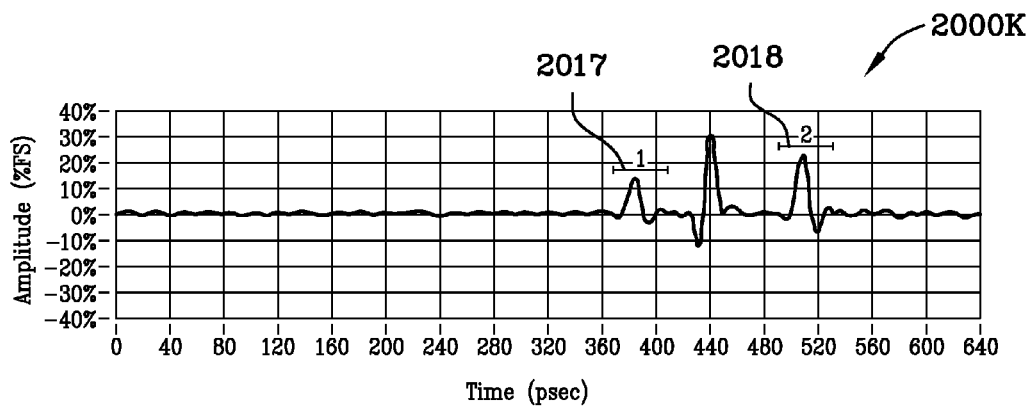
FIG. 20K is the oscilloscope-like trace of the fused waveform containing the front surface (FS) echo, the substrate echo (M") and the back surface (BS) echo of FIG. 20J illustrating gates placed over the front surface (FS) echo and the back surface (BS) echo.
Figure 20L:
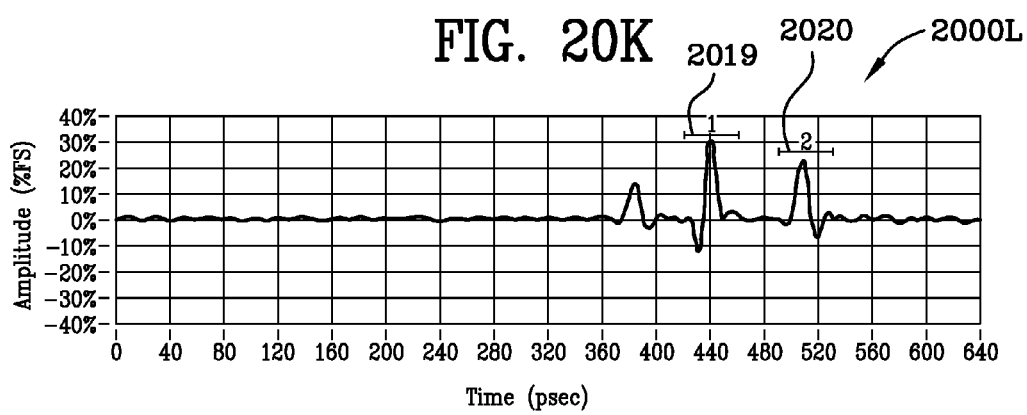
FIG. 20L is the oscilloscope-like trace of the fused waveform containing the front surface (FS) echo, the substrate echo (M") and the back surface (BS) echo of FIG. 20J illustrating gates placed over the substrate echo (M") and the back surface (BS) echo.

Referring to FIG. 20L, next form the Δt delay image between back surface echo (BS) waveform and substrate echo (M", M") waveform M" echoes. First select using a mouse the choice "multigate" under "Gate Type" menu to reset the gates selected. The gates should now be placed as follows: gate1 (2019) on substrate echo (M", M") waveform echo and gate 2 (2020) on back surface (BS) echo waveform. Form the delay image (using either the peak to peak or cross-correlation methods), then save the image as a .bin or .txt file.

To form thickness-independent velocity or microstructure independent thickness image perform the following steps.

Open the fused file and Select either Thickness-Independent Velocity or Microstructure-Independent Thickness Image Type under Form Image of Type Calculate Velocity Thickness. Open either .bin or .txt files for 2τ and Δt image files. The software algorithm uses the following equations and solves for V, velocity and d, thickness, as follows:

Thickness-independent velocity is given by the following equation:

$$d = \frac{c(2\tau - \Delta\tau)}{2}$$

Microstructure-independent Thickness is given by the following equation:

$$V = c\left(1 - \frac{\Delta\tau}{2\tau}\right)$$

Figure 20M:
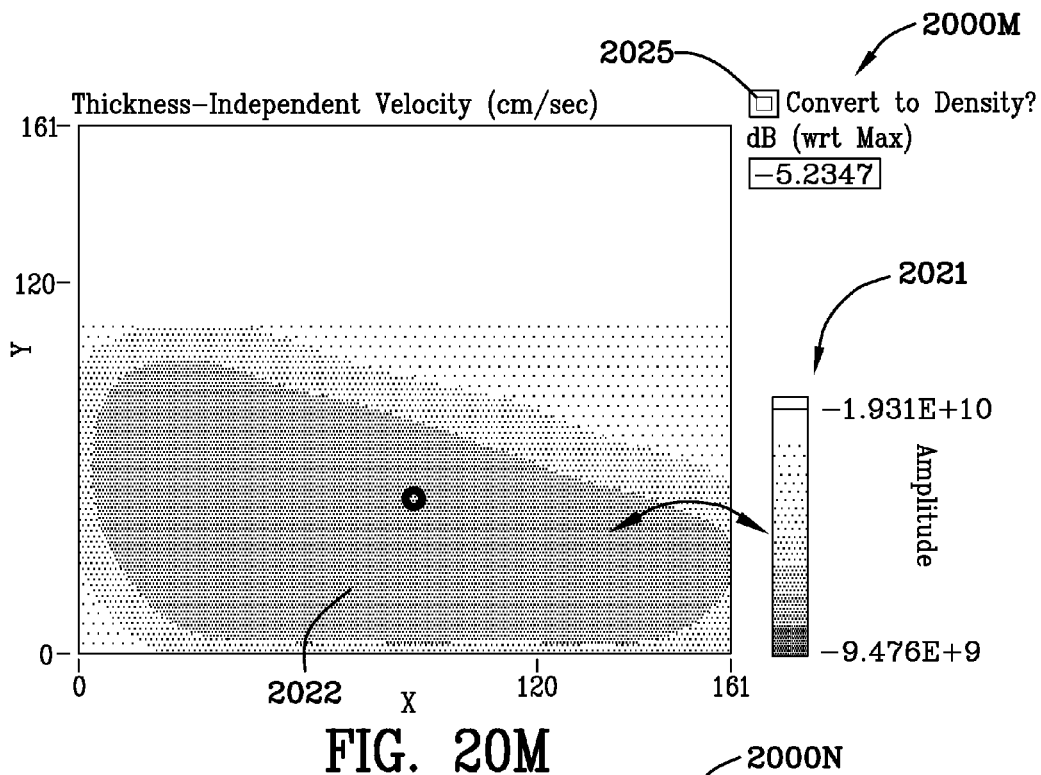
FIG. 20M is a computer generated image of the thickness-independent velocity image generated by the computer program.
Figure 20N:
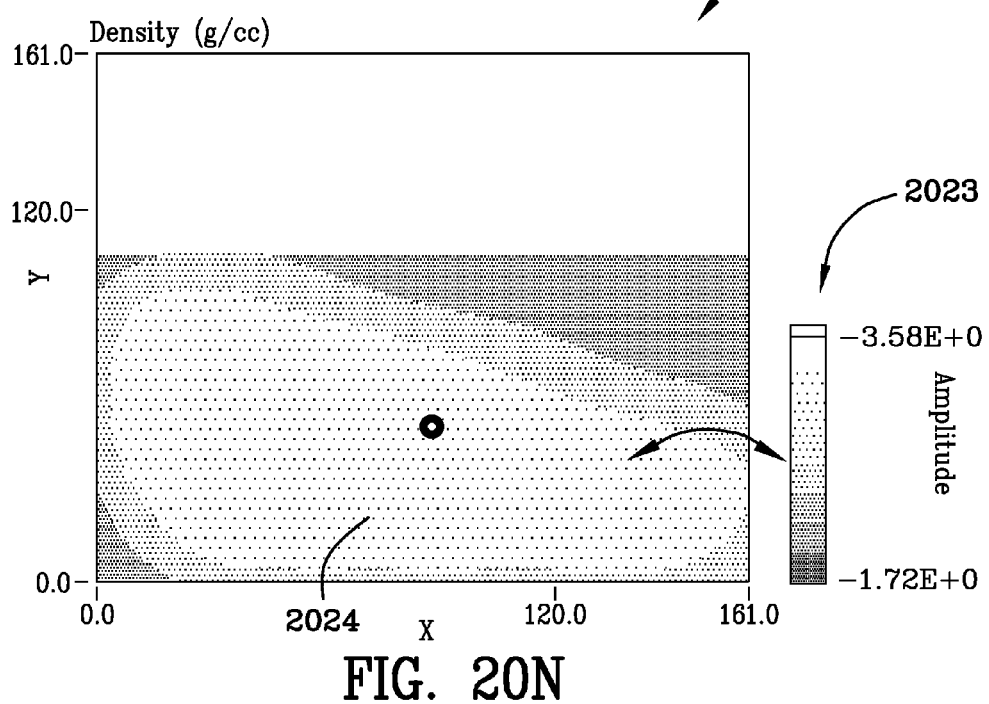
FIG. 20N is a computer generated image of the density image corresponding to the velocity image of FIG. 20M generated by the computer program.

FIG. 20M is a velocity image 2000M which represents the thickness-independent velocity in gray shade according to the x,y coordinates selected and is then compared to the bar graph (gray scale ramp) 2021. Reference numeral 2022 illustrates the present x-y coordinate in the approximate center of FIG. 20. To convert the images to a density image, the software prompts selection/conversion 2025 as illustrated in FIG. 20M. FIG. 20N illustrates 2000N the density corresponding to the x,y coordinates and reference numeral 2024 illustrates the present x, y coordinate.

To obtain the density maps/images from thickness-independent velocity maps/images, select the box on the graphical user interface "Convert to Density" which spawns a dialog prompting the entry of a slope (m) and intercept (b) of the best linear fit for the velocity-physical density relationship that has been determined through experiments and analysis of the material under test/evaluation.

The final density image may require post-processing using another software module within NDE Wave & Image Processor if background was obtained in the scan or if outlier data points from bad data are obtained. For example, contrast expansion/outlier removal of the sample area may need to be performed using histogram range-based contrast expansion module. Quantitative density and thickness maps are obtained. See FIG. 21.

One exemplary process for non-destructive evaluation of a sample using a computer, a computer display and a computer program includes implementing an algorithm for determining the velocity of terahertz electromagnetic radiation in the sample without prior knowledge of the thickness of the sample and determining the thickness of the sample without prior knowledge of the velocity of the terahertz electromagnetic radiation in the sample. The terahertz electromagnetic radiation is produced by a source spaced apart from said sample under test and propagated at the speed of light, c, in a medium located between the source and the sample, and is set forth in an example schematically illustrated in FIG. 18.

The first exemplary process comprises the steps of: emitting and scanning terahertz electromagnetic radiation from the source, the terahertz radiation applied to a plurality of scan points arranged according to x and y coordinates of the scanning, the plurality of scan points includes an area at least as large as the surface of the sample, 1801. The scan points may be arranged in an x-y matrix of 171 data points by 171 data points (or any arrangement of data points as dictated by the sample size and scan resolution desired).

This example of the process includes recording and storing, in a substrate echo waveform data set file, on a scan point by scan point basis, a substrate echo (M") waveform of the terahertz electromagnetic radiation received from the substrate without the sample present, and recording and storing the front surface (FS) waveform and the back surface (BS) waveform of the terahertz electromagnetic radiation received with the sample present, 1802. So, for example, if there are $171^2$ data points then there are 29,241 data points and each data point or data area has associated therewith a substrate echo (M") waveform, a back surface (BS) echo wave form and a front surface (FS) echo waveform. These waveforms are superimposed on a time line (abscissa) and display amplitude with respect to time. See FIG. 20B for an illustration of superimposed waveforms for scan point x=86, y=84. Reference numeral 2001 is the back surface (BS) echo waveform and the front surface echo waveform is indicated by reference numeral 2002 in FIGS. 20, 20A and 20B The substrate echo (M") waveform is illustrated in FIGS. 20A and 20B. Therefore, the step of superimposing the substrate echo (M") waveform, the front surface (FS) echo waveform, and the back surface (BS) echo waveform, 1803 accomplishes the superposition. Gating (2013, 2012) the substrate echo (M"), and gating and conditioning the front surface (FS) echo waveform are performed in the program as a precursor to fusing the echo waveforms together. See FIG. 20H which illustrates placing the first gate 2013 and the second gate 2012 over the substrate echo (M") waveform and the front surface (FS) echo waveform, respectively.

After superposition (FIG. 20B) has been performed an image container (FIG. 20C, display on the graphical user interface) appears and the user may interactively with the computer mouse or a touch screen interface canvas the sample under evaluation to determine the characteristics of the waveforms on a point by point basis (x,y coordinates). This canvassing or inspection gives the software user an idea of the breadth or variance of the front surface (FS) echo waveform over a given range. This range then determines the width of the gate over the front surface (FS) echo waveform. The range of the superimposed waveforms are illustrated in FIGS. 20D, 20E, and 20F. Movement of the superimposed waves is illustrated in comparing FIGS. 20D, 20E and 20F. FIG. 20D corresponds to x=20, y=150, FIG. 20E corresponds to x=86, y=84, and FIG. 20F corresponds to x=150, y=20. A single waveform is illustrated as an oscilloscope trace and it is this single waveform that is gated. See FIG. 20G which illustrates delaying the substrate echo (M") waveforms 2003 as indicated by the time shifted substrate echo (M") waveform 2003A. The substrate echo (M") waveform is also gated.

Signal conditioning of the front surface echo (FS), namely, applying digital filtering, wavelet denoising, and/or wavelet reconstruction, adjusting the front surface (FS) gate amplification factor, Z-axis move distance if refocusing on FS occurred (+value), FS Subtraction Offset, as needed may be applied. See FIG. 20I, reference numeral 2014 indicating possible selections of signal conditioning processes.

The step of fusing the substrate echo (M") waveform and the front surface echo (FS) waveform into the back surface (BS) echo waveform is performed 1804 and selecting signal conditioning is performed on the front surface echo (FS) waveforms for each of the data points as it is fused with its respective substrate echo (M") waveform and the back surface (BS) waveforms. Fusing is accomplished after gating the waveforms by selecting the "fuse gated waves" action, 2015. See FIG. 20I. Once all of the echo waveforms are fused into a fused data set the next step of this example is to gate the echo waveforms and determine the time difference between the front surface echo (FS) waveform and the back surface (BS) echo waveform, $2\tau$, and storing values of $2\tau$ for each scan point, 1805. The gates are interactively applied with the user of the software program, computer and computer display, actively dragging, dropping and adjusting the width (in pico seconds) of the gate 2017 over the respective front surface (FS) echo waveform and the gate 2018 over the back surface (BS) echo waveforms. Prior to selecting the position and width of the gates of the front surface (FS) waveform and the back surface waveform (BS) waveforms, the user may canvas the fused file (FIG. 20J) over the extent of the sample under evaluation to assist the user in deciding how wide the gates should be in time. The canvassing of the fused files is done in the image container in windows similar to those illustrated in FIGS. 20D-F.

Next, the step of this example includes interactively gating the echo (2019, 2020) waveforms and determining the time difference between the substrate echo wave (M") waveform and the back surface (BS) waveform, $\Delta t$, and storing values of $\Delta t$ for each scan point, 1806. Similarly to positioning the gates for the calculation and storing of the $2\tau$ data set file above, and prior to selecting the position and width of the gates for the front substrate echo (M") waveform and the back surface (BS) waveform echo, the user may canvas the fused file over the extent of the sample under evaluation to assist the user in deciding how wide (in time) the gates should be in time.

Next in this example of the process, the step of using the stored values of $2\tau$ and $\Delta t$ in accordance with the algorithm to determine the velocity of the terahertz electromagnetic radiation in the sample on a scan point by scan point basis is performed 1807. The algorithm includes the step of determining and storing, on a scan point by scan point basis, the velocity, V, of terahertz electromagnetic radiation in the sample without prior knowledge of the thickness. The velocity, V, is determined by solving the equation, $V=c(1-\Delta t/2\tau)$, for each the scan point and storing the determined velocity value in a velocity computer file on a scan point by scan point basis 1808.

Similarly, using the stored values of $2\tau$ and $\Delta t$ in the algorithm to determine the thickness of the sample on a scan point by scan point basis in accordance with the algorithm to determine on a scan point by scan point basis, the thickness, d, of the sample without prior knowledge of the velocity of the terahertz electromagnetic radiation in the sample. The thickness is determined by solving the equation, $d=c(2\tau-\Delta t)/2$, for each the scan point and storing the thickness value in a thickness computer file 1809.

Figure 17:
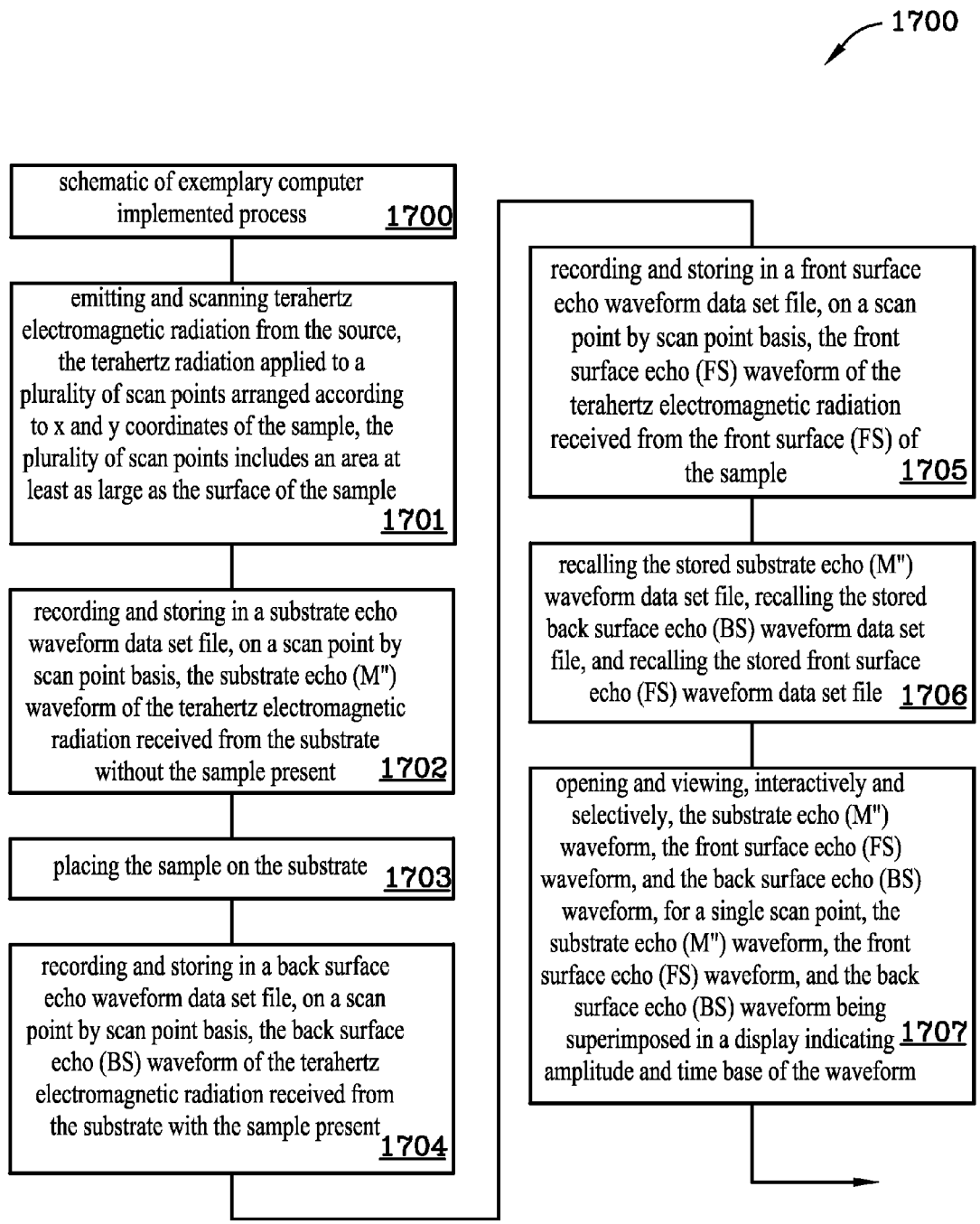
FIGS. 17-17C are a schematic of an exemplary computer implemented process for nondestructively determining terahertz electromagnetic radiation velocity without prior knowledge of thickness of a sample for determining thickness without prior knowledge of the terahertz electromagnetic radiation velocity in the sample.
Figure 17A:
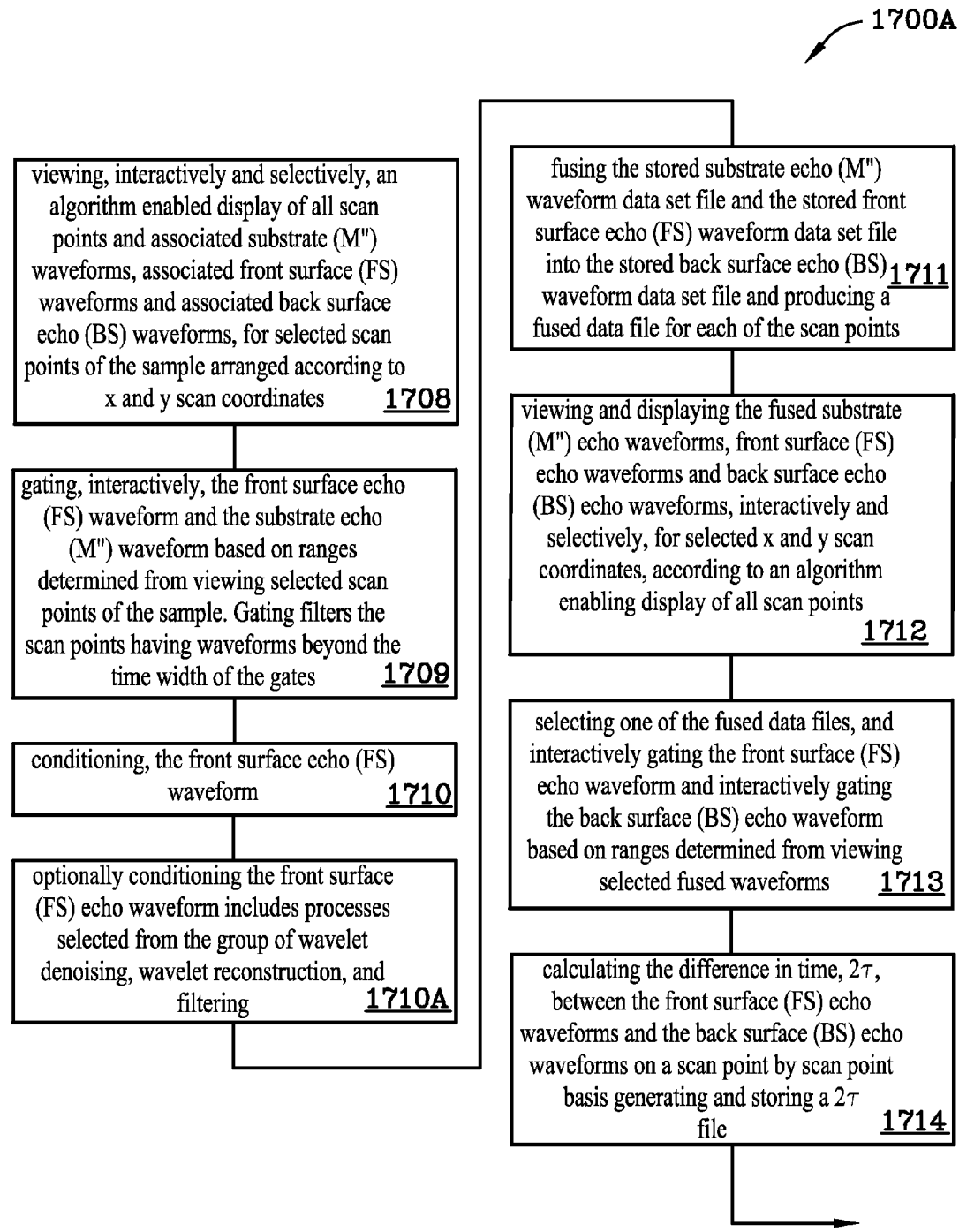
Figure 17B:
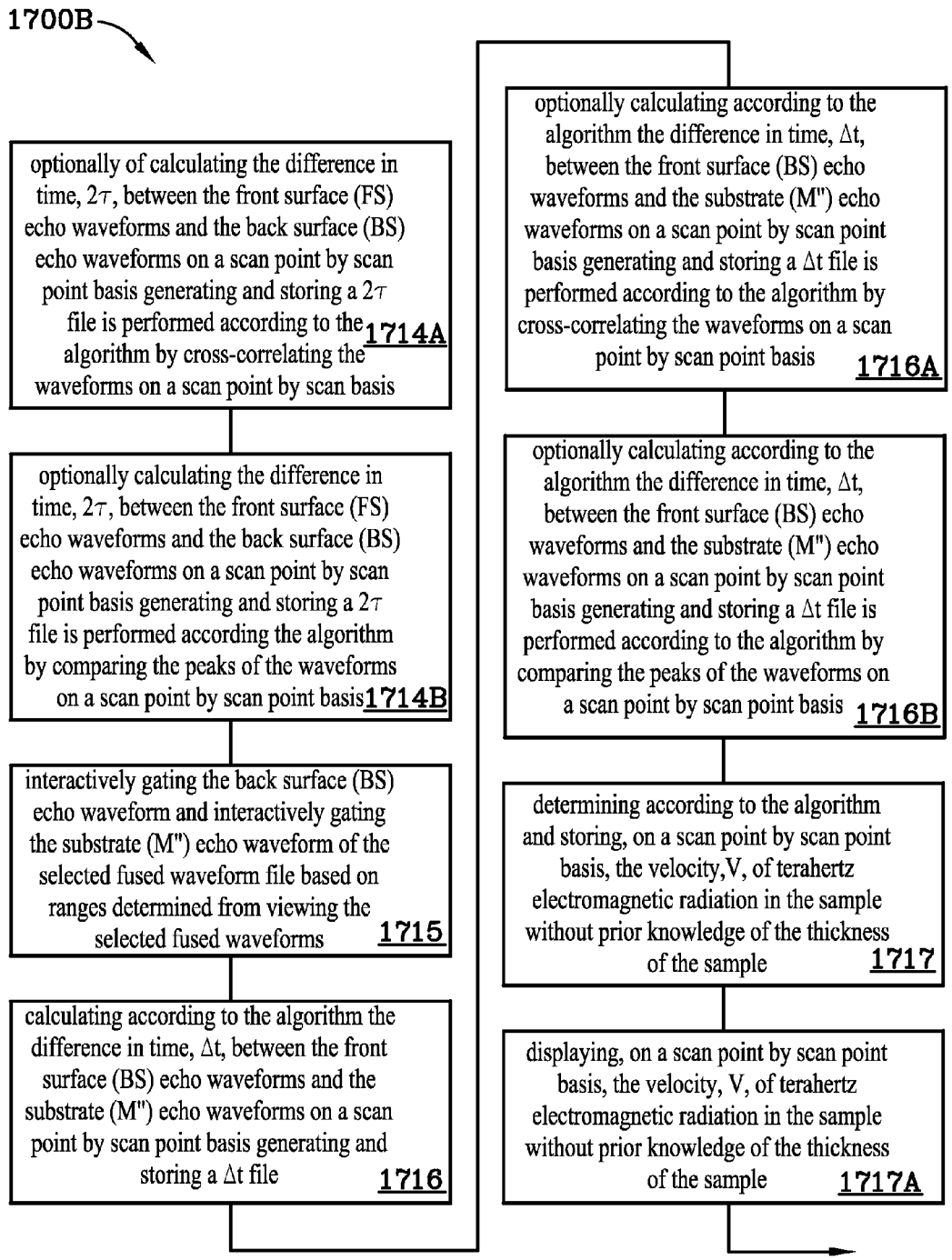

Another exemplary process for non-destructive evaluation of a sample using a computer, a display and a computer program implementing an algorithm is disclosed in a block diagram 1700 in FIGS. 17-17C. The algorithm includes determining the velocity, V, of terahertz electromagnetic radiation in the sample without prior knowledge of the thickness of the sample and determining the thickness of the sample without prior knowledge of the velocity of the terahertz electromagnetic radiation in the sample. The terahertz electromagnetic radiation produced by a source spaced apart from the sample under test and propagated at the speed of light, c, in a medium located between the source and the sample.

The exemplary process of FIGS. 17-17C includes the steps of: emitting and scanning terahertz electromagnetic radiation from the source, the terahertz radiation applied to a plurality of scan points arranged according to x and y coordinates of the sample, the plurality of scan points includes an area at least as large as the surface of the sample, 1701. Recording and storing in a substrate echo waveform data set file, on a scan point by scan point basis, the substrate echo (M") waveform of the terahertz electromagnetic radiation received from the substrate without the sample present is performed, 1702. Next, placing the sample on the substrate, 1703 is required so as to obtain front surface (FS) echo waveforms and back surface (BS) echo waveforms. Recording and storing in a back surface echo waveform data set file, on a scan point by scan point basis, the back surface echo (BS) waveform of the terahertz electromagnetic radiation received from the substrate with the sample present, 1704 is the next step performed. Further, the step of recording and storing in a front surface echo waveform data set file, on a scan point by scan point basis, the front surface echo (FS) waveform of the terahertz electromagnetic radiation received from the front surface (FS) of the sample, 1705 is performed.

In the exemplary process of FIGS. 17-17C, the next step is recalling the stored substrate echo (M") waveform data set file, recalling the stored back surface echo (BS) waveform data set file, and recalling the stored front surface echo (FS) waveform data set file, 1706. Next, the step of opening and viewing, interactively and selectively, the substrate echo (M") waveform, the front surface echo (FS) waveform, and the back surface echo (BS) waveform, for a single scan point, the substrate echo (M") waveform, the front surface echo (FS) waveform, and the back surface echo (BS) waveform being superimposed in a display indicating amplitude and time base of the waveform, 1707 is performed.

Next, viewing, interactively and selectively, an algorithm enabled display of all scan points and associated substrate (M") waveforms, associated front surface (FS) waveforms and associated back surface echo (BS) waveforms, for selected scan points of the sample arranged according to x and y scan coordinates, 1708 is performed. Gating, interactively, the front surface echo (FS) waveform and the substrate echo (M") waveform based on ranges determined from viewing selected scan points of the sample. Gating filters the waveform portions beyond the time width of the gates, 1709. Next, the step of conditioning, the front surface echo (FS) waveform, 1710 is performed. Optional steps of conditioning the front surface (FS) echo waveform may include processes selected from the group of wavelet denoising, wavelet reconstruction, and filtering, 1710A.

Next, the step of fusing the stored substrate echo (M") waveform data set file and the stored front surface echo (FS) waveform data set file into the stored back surface echo (BS) waveform data set file and producing a fused data file for each of the scan points, 1711 is performed. Once fused, the step of viewing and displaying the fused substrate (M") waveforms, front surface (FS) waveforms and associated back surface echo (BS) waveforms, interactively and selectively, for selected fused waveforms having x and y scan coordinates, according to an algorithm enabled display of all scan points, 1712 is performed. This interactively allows the user to view the fused file set according to a specific data point and that data point coordinate is viewable by the user.

Next, the exemplary process of FIGS. 17-17C includes the user selecting one of the fused data files, and interactively gating the front surface (FS) echo waveform and interactively gating the back surface (BS) echo waveform based on ranges determined from viewing the selected fused waveforms, 1713. The user selects the gates as aforestated to calculate the difference in time, $2\tau$, between the front surface (FS) echo waveforms and the back surface (BS) echo waveforms on a scan point by scan point basis generating and storing a $2\tau$ file, 1714. The step of calculating the difference in time, $2\tau$, between the front surface (FS) echo waveforms and the back surface (BS) echo waveforms on a scan point by scan point basis generating and storing a $2\tau$ file is performed according to the algorithm by cross-correlating the waveforms on a scan point by scan point basis 1714A.

Still referring to the process of FIGS. 17-17C, the step of calculating according to the algorithm the difference in time, $\Delta t$, between the front surface (BS) echo waveforms and the substrate (M") echo waveforms on a scan point by scan point basis generating and storing a $\Delta t$ file is optionally performed according to the algorithm by cross-correlating the waveforms on a scan point by scan point basis, 1714B.

Still referring to the process of FIGS. 17-17C, the step of interactively gating the back surface (BS) echo waveform and interactively gating the substrate (M") echo waveform of the selected fused waveform file based on ranges determined from viewing the selected fused waveforms, 1715 is performed. Next, the step of calculating according to the algorithm the difference in time, $\Delta t$, between the front surface (BS) echo waveforms and the substrate (M") echo waveforms on a scan point by scan point basis generating and storing a $\Delta t$ file, 1716 is performed. The step of calculating the difference in time, $2\tau$, between the front surface (FS) echo waveforms and the back surface (BS) echo waveforms on a scan point by scan point basis generating and storing a $2\tau$ file is performed by comparing the peaks of the waveforms on a scan point by scan point basis, 1716A. Still referring to the exemplary process of FIGS. 17-17C, the step of calculating according to the algorithm the difference in time, $\Delta t$, between the front surface (BS) echo waveforms and the substrate (M") echo waveforms on a scan point by scan point basis generating and storing a $\Delta t$ file is optionally performed by comparing the peaks of the waveforms on a scan point by scan point basis, 1716B.

Still referring to the exemplary process of FIGS. 17-17C, the next step is determining according to the algorithm and storing, on a scan point by scan point basis, the velocity of terahertz electromagnetic radiation in the sample without prior knowledge of the thickness of the sample 1717. Next the results are displayed, on a scan point by scan point basis, the velocity of terahertz electromagnetic radiation in the sample without prior knowledge of the thickness of the sample, 1717A. If the results are preferred in terms of density, the step of calculating, on a scan point by scan point basis, the density of the sample without prior knowledge of the thickness of the sample, 1717B is performed according to a look-up table based on known properties of the test sample under evaluation.

According to the exemplary process of FIGS. 17-17C, the next step of determining and storing according to an algorithm, on a scan point by scan point basis, the velocity of terahertz electromagnetic radiation in the sample without prior knowledge of the thickness, is performed according to the algorithm solving for V using the equation: $V=c(1-\Delta t/2\tau)$, 1717C. Next, the step of determining according to the algorithm and storing, on a scan point by scan point basis, the thickness of the sample without prior knowledge of the velocity of the terahertz electromagnetic radiation in the sample, 1718 is performed. Once the velocity is determined it is displayed, on a scan point by scan point basis, the thickness of the sample without prior knowledge of the velocity of the terahertz electromagnetic radiation in the sample, 1718A.

And finally, according to the exemplary process set forth in FIGS. 17-17C, the step of determining according to the algorithm and storing, on a scan point by scan point basis, the thickness of the sample without prior knowledge of the velocity of the terahertz electromagnetic radiation in the sample, is performed according to the algorithm solving for "d" using the equation: $d=c(2\tau-\Delta t)/2$, 1718C.

The step of fusing in the exemplary processes of FIGS. 17-17C and 18-18A includes doubling the time base of the fused data waveform, 1790.

Figure 18:
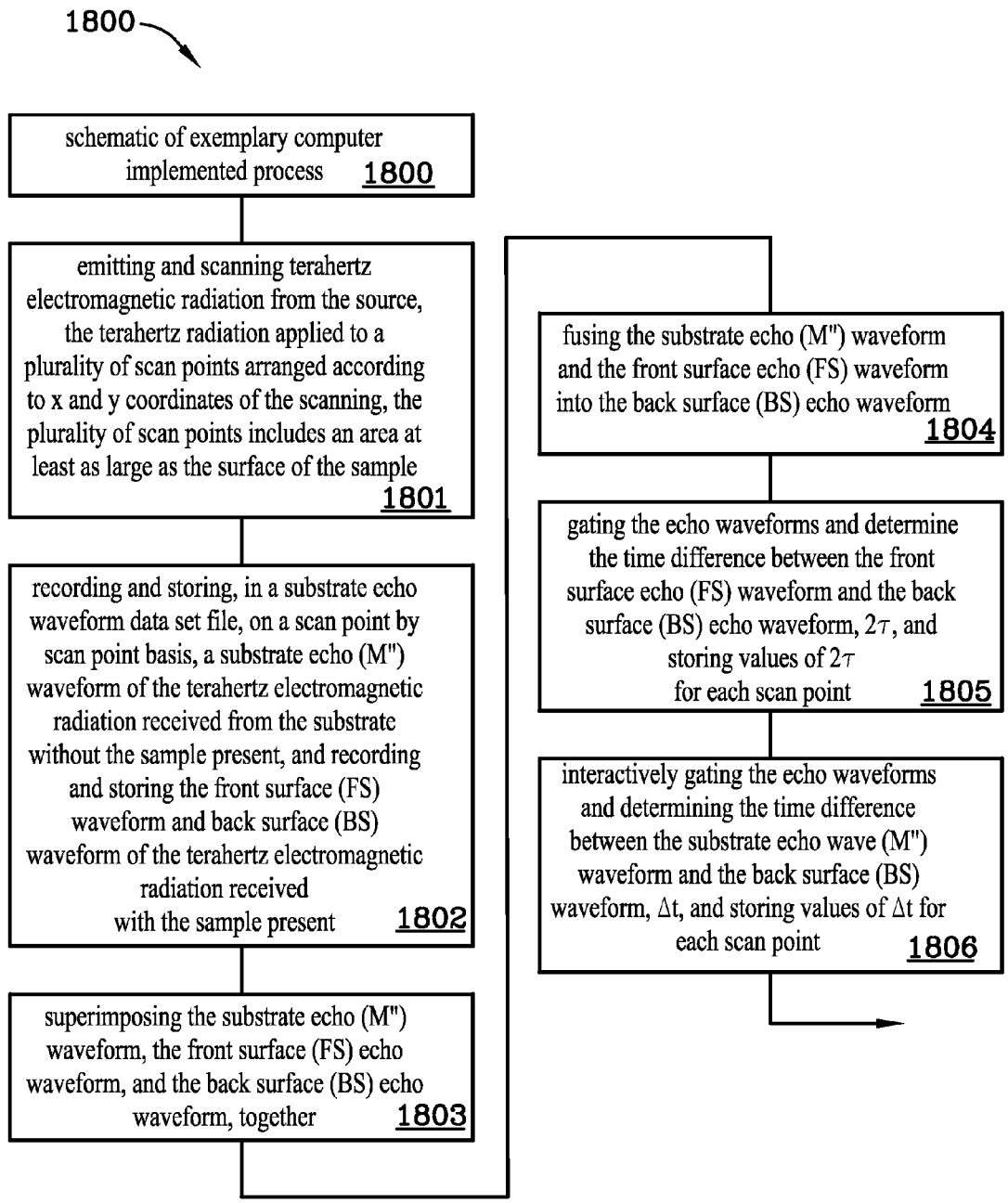

The steps of gating and conditioning the substrate echo (M") and the front surface (FS) echo waveforms in the exemplary process of FIGS. 17 and 18 include the step of delaying the substrate echo in time to better gate the substrate echo and then remove the delay when the step of fusing the substrate echo (M") waveform and the front side echo (FS) waveform into the back side echo waveform (BS) is performed, 1791.

Figure 19:
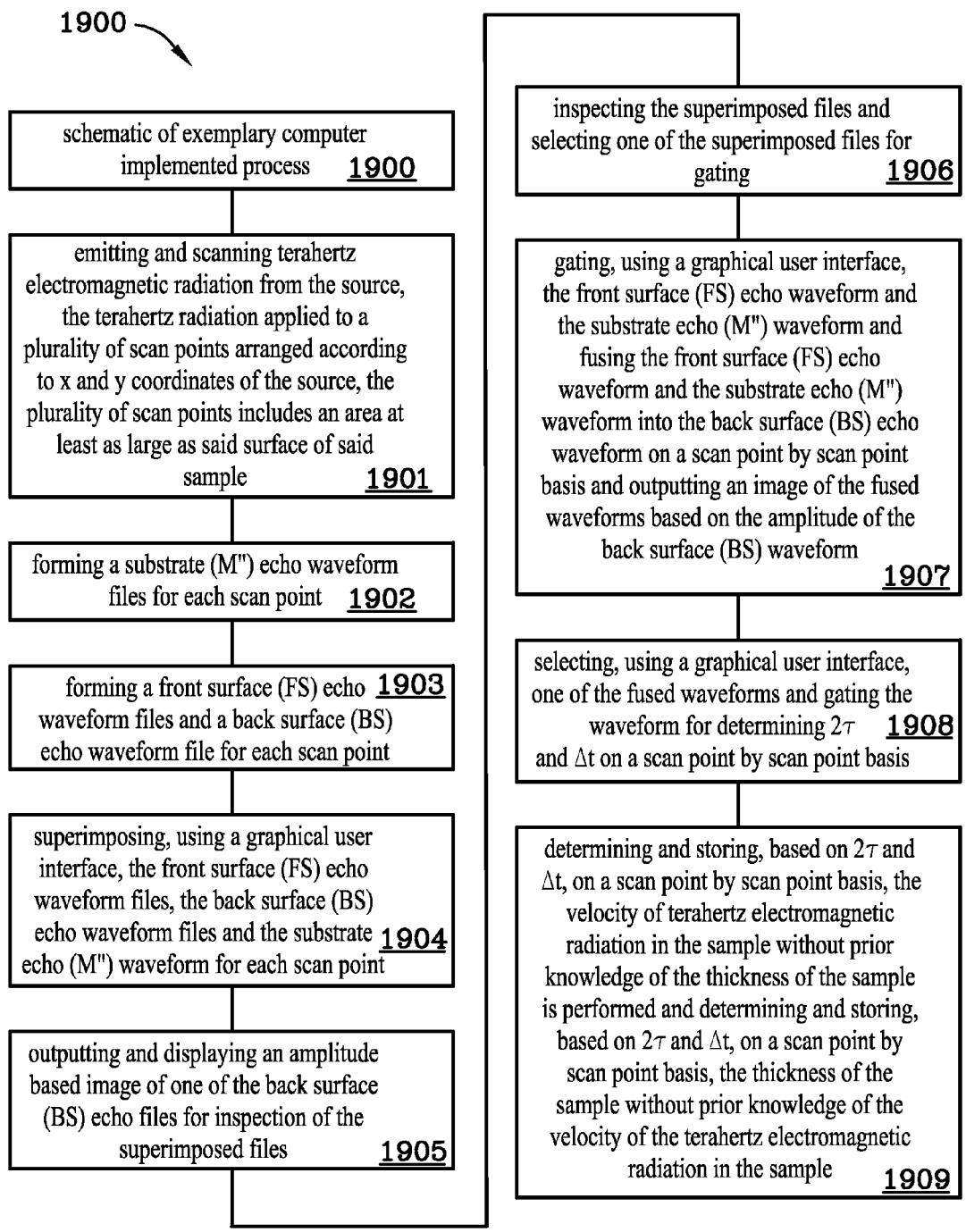
FIG. 19 is another schematic of an exemplary computer implemented process for nondestructively determining terahertz electromagnetic radiation velocity without prior knowledge of thickness of a sample for determining thickness without prior knowledge of the terahertz electromagnetic radiation velocity in the sample.

Another exemplary process for non-destructive evaluation of a sample using a computer, a display and a computer program implementing an algorithm is disclosed in a block diagram 1900 in FIG. 19. The process of FIG. 19 includes emitting and scanning terahertz electromagnetic radiation from said source, said terahertz radiation applied to a plurality of scan points arranged according to x and y coordinates of said source, said plurality of scan points includes an area at least as large as said surface of said sample, 1901. The process includes forming substrate (M") echo waveform files for each scan point 1902 and forming front surface (FS) echo waveform files and back surface (BS) echo waveform files for each scan point 1903.

According to the process of the example of FIG. 19, the next step includes superimposing, using a graphical user interface, said front surface (FS) echo waveform files, said back surface (BS) echo waveform files and said substrate echo (M") waveform for each scan point 1904. Next, the step of outputting and displaying an amplitude based image of one of said back surface (BS) echo files for inspection of said superimposed files 1905 is performed.

Interactively, through a graphical user interface, inspecting said superimposed files; and selecting one of said superimposed files for gating is performed 1906. Gating, using a graphical user interface, said front surface (FS) echo waveform and said substrate echo (M") waveform and fusing said front surface (FS) echo waveform and said substrate echo (M") waveform into said back surface (BS) echo waveform on a scan point by scan point basis and outputting a composite image of said fused waveforms based on said amplitude of said back surface (BS) waveform 1907 is performed next. Selecting, using a graphical user interface, one of said fused waveforms and gating said waveform for determining $2\tau$ and $\Delta t$ on a scan point by scan point basis, 1908 is performed. Next, using the algorithm, determining and storing, based on $2\tau$ and $\Delta t$, on a scan point by scan point basis, the velocity of terahertz electromagnetic radiation in said sample without prior knowledge of the thickness of said sample is performed. Finally, the step of determining and storing, based on $2\tau$ and $\Delta t$, on a scan point by scan point basis, said thickness of said sample without prior knowledge of said velocity of said terahertz electromagnetic radiation in said sample 1909 is performed.

FIG. 20 is an oscilloscope-like trace 2000 of a front surface (FS) echo waveform and a back surface (BS) echo waveform for the x=86, y=84 scan point coordinate. Reference numeral 2001 denotes back surface (BS) echo waveform for the x=86, y=84 scan point coordinate. Similarly, reference numeral 2002 denotes the front surface (FS) echo waveform for the x=86, y-84 scan point coordinate.

FIG. 20A is an oscilloscope-like trace 2000A of a substrate echo (M") waveform for the x=86, y=84 scan point coordinate. Reference numeral 2003 denotes the substrate echo (M") waveform for the x=86, y=84 scan point coordinate.

FIG. 20B is an oscilloscope-like trace 2000B of the front surface (FS) echo waveform 2002 and the substrate echo (M") 2003 waveform superimposed into the back surface (BS) echo waveform 2001 for the x=86, y=84 scan point coordinate.

FIG. 20C is an image 2000C of the back surface (BS) echo waveform illustrating the x-y scan points ranging from x=171 to y=171 allowing the user to canvas any of the scan points to produce superimposed files having the front surface (FS) echo waveform, the substrate echo (M") waveform superimposed into and onto the back surface (BS) echo waveform. Reference numeral 2004 denotes the x=86 scan coordinate, reference numeral 2005 denotes the y=84 scan coordinate, reference numeral 2006 denotes the cursor location/red circle and reference numeral 2007 indicates the gray scale amplitude meter. As such the present cursor position yields the information for the oscilloscope like traces illustrated in FIGS. 20, 20A and 20B.

FIG. 20D is an image 2000D of the superimposed file for scan coordinates of x=20, y=150 and the corresponding oscilloscope-like trace of the superimposed files having the front surface (FS) echo waveform, the substrate echo (M") waveform superimposed into and onto the back surface (BS) echo waveform. Reference numeral 2008 illustrate the corresponding oscilloscope trace for cursor location x=20, y=150.

FIG. 20E is an image 2000E of the superimposed file for scan coordinates of x=86, y=84 and the corresponding oscilloscope-like trace of the superimposed files having the front surface (FS) echo waveform, the substrate echo (M") waveform superimposed into and onto the back surface (BS) echo waveform. Reference numeral 2009 indicates the cursor location x=86, y=84 and the corresponding oscilloscope trace.

FIG. 20F is an image 2000F of the superimposed file for scan coordinates of x=150, y=20 and the corresponding oscilloscope-like trace of the superimposed files having the front surface (FS) echo waveform, the substrate echo (M") waveform superimposed into and onto the back surface (BS) echo waveform. Reference numeral 2010 illustrates the cursor location x=150, y=20 and the corresponding oscilloscope-like trace.

FIG. 20G is a screen shot 2000G from the software program implementing signal condition of the front surface (FS) echo waveform and delaying, by a specified amount of time, the substrate echo (M") waveform to facilitate gating of the substrate echo (M") waveform. Reference numeral 2011 denotes a time shift input dialog box where the operator inserts a time delay to separate the substrate echo (M") from the back surface (BS) echo waveform. Reference numeral 2003A indicates the position of the substrate echo which has been time shifted to separate it from the back surface (BS) echo waveform.

FIG. 20H is an oscilloscope-like trace 2000H of the time shifted substrate echo (M") waveform and gating of the front surface (FS) echo waveform and the time shifted substrate (M") waveform. Reference numeral 2012 denotes the front surface (FS) echo waveform gate and reference numeral 2013 indicates the substrate echo (M") waveform gate. These gates are placed as stated prior to fusing the waves as is illustrated in FIG. 20I.

FIG. 20I is a screen shot 2000I similar to FIG. 20G from the software program implementing signal condition of the front surface (FS) echo waveform and delaying, by a specified amount of time, the substrate echo (M") waveform to facilitate gating of the substrate echo (M") waveform and in addition indicating the "fuse gated waves" boolean button. Reference numeral 2014 globally denotes the boolean buttons for front surface (FS) echo wave form signal condition selectable options and reference numeral 2015 is the boolean button for fusing the gated waves.

FIG. 20J is an oscilloscope-like trace 2000J of the fused waveform 2016 containing the front surface (FS) echo, the substrate echo (M") and the back surface (BS) echo. FIG. 20K is the oscilloscope-like trace 2000K of the fused waveform containing the front surface (FS) echo, the substrate echo (M") and the back surface (BS) echo of FIG. 20J illustrating gates 2017, 2018 placed over the front surface (FS) echo and the back surface (BS) echo, respectively.

FIG. 20L is the oscilloscope-like trace 2000L of the fused waveform containing the front surface (FS) echo, the substrate echo (M") and the back surface (BS) echo of FIG. 20J illustrating gates 2019, 2020 placed over the substrate echo (M") and the back surface (BS) echo, respectively.

FIG. 20M is a computer generated image 2000M of the thickness-independent velocity image generated by the computer program. Reference numeral 2021 is the velocity amplitude gray scale indicator associated with the image of FIG. 20. Reference numeral 2022 denotes the cursor position of the velocity image. Check Box 2025 for converting velocity image to a density image is indicated in FIG. 20M enabling the user to convert from the velocity image to the density image of FIG. 20N.

FIG. 20N is a computer generated image 2000N of the density image corresponding to the velocity image of FIG. 20M generated by the computer program. Reference numeral 2023 indicates the density amplitude gray scale indicator and reference numeral 2024 indicates the cursor position of the density image. In both FIGS. 20M and 20N enable the user to canvas the images to obtain site specific information for the scan coordinates.

Figure 21:
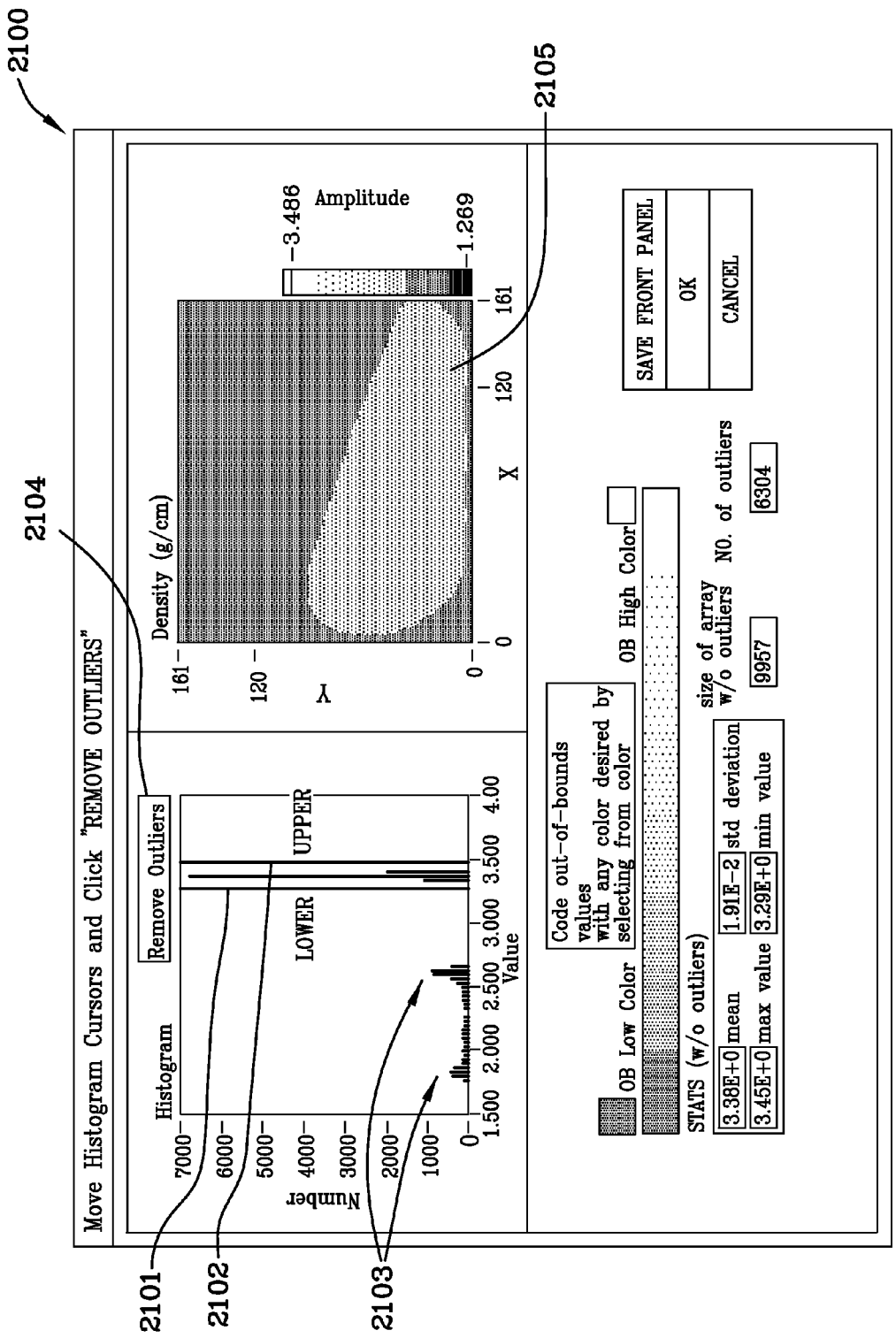
FIG. 21 is a screen shot of the program illustrating a histogram of the density plot and a density image after the outliers have been removed.

FIG. 21 is a screen shot 2100 of the program illustrating a histogram of the density plot and a density image after the outliers have been removed. The remove outliers button is illustrated in the screen shot. The screen shot 2100 is obtained from the density image wherein processing is selected followed by "advanced" and remove outliers. Reference numeral denotes 2101 is the minimum value of acceptable density data points and reference numeral 2102 indicates the maximum value of acceptable density data points. Outliers 2103 are indicated in the histogram and button 2104 prompts the program to remove outliers. Reference numeral 2105 denotes the true density image.

REFERENCE NUMERALS

100—schematic view of the terahertz measuring system
101—transceiver
102—terahertz source
103—terahertz receiver
104—front surface of metal substrate
104A—metal substrate
105—back surface of metal substrate
106—beginning of void
107—end of void/front surface of metal substrate
108—foam, silicon nitride or other dielectric
109—front surface of foam, silicon nitride or other dielectric
110—gate for signal analysis 200—density of sprayed on foam insulation versus velocity of terahertz electromagnetic radiation therein
200A—density of silicon nitride versus velocity of terahertz electromagnetic radiation therein
300—schematic view of terahertz measuring system and graph of output voltages of respective signals versus time
301—thin dielectric sheet
400—graph of uncertainty (in percent) of thickness independent velocities as a function of 2τ, Δt and V.
500—graph of uncertainty (in percent) of velocity as a function of thickness, d.
600—schematic of step wedge foam blocks
601—aluminum substrate
602—first foam block
603—second foam block
604—third foam block
605—fourth foam block
700—plot of 2τ as a function of thickness and density
700A—schematic illustration of thickness variation
700B—schematic illustration of density variation
800—physically measured density map for a 6 by 15 set of foam blocks
800A—density plot
801—comparison portion of physically measured density map
802—comparison portion of physically measured density map
900—terahertz density map
900A—terahertz density plot
901—comparison portion of thickness independent terahertz density map
902—comparison portion of thickness independent terahertz density map
1000—hand measured thickness map for a 6 by 15 set of foam blocks
1000A—illustrates the thickness in centimeters by shade of gray
1001—ellipse indicating an area of the hand measured thickness map to be compared to a terahertz thickness map
1100—a terahertz thickness image for the 6 by 15 set of foam blocks (determined independently of velocity) according to the methodology of the invention
1100A—thickness by shade of gray in centimeters for the terahertz thickness map of FIG. 11
1101—ellipse indicating an area of the terahertz thickness map to be compared to a physically measured thickness map
1200—schematic diagram of a process for measuring the velocity of terahertz electromagnetic radiation in a material sample without prior knowledge of the thickness of the sample, the terahertz electromagnetic radiation produced by a source spaced apart from the sample under test at the speed of light, c, in a medium located between the source and the sample, the sample residing on the substrate
1201—emitting terahertz electromagnetic radiation from the source
1202—measuring the travel time of the terahertz electromagnetic radiation to and from the substrate without the sample present, t" (t-double prime)
1203—placing the sample on the substrate
1204—measuring the travel time of the terahertz electromagnetic radiation to and from the substrate with the sample/dielectric present, t' (t-prime)
1205—subtracting t" from t' to determine the transmission time difference with the sample present and without the sample present, Δt
1206—measuring the travel time of the terahertz electromagnetic radiation to and from the sample, $2t_1$
1207—determining the time difference between the FS echo and the BS echo, 2τ
1208—placing a sheet of plastic paper onto the sample to create an adequate dielectric mismatch
1209—dividing Δt by 2τ and determining the quotient
1210—subtracting the quotient from 1 to obtain a factor
1211—multiplying the factor to determine the velocity of the terahertz electromagnetic radiation in the sample
1212—determining the microstructural variation of the sample
1213—determining the density of the material
1214—evaluating, in a plurality of locations, the sample for microstructural variations; and mapping the variations by location
1215—controlling the spacing between the source and the substrate
1216—determining, initially, the approximate time location of the sample from the terahertz radiation source
1300—schematic diagram of a process for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample, the sample residing on the substrate
1301—emitting terahertz electromagnetic radiation from the source;
1302—measuring the travel time of the terahertz electromagnetic radiation to and from the substrate without the sample present, t" (t-double prime)
1303—placing the sample on the substrate
1304—measuring the travel time of the terahertz electromagnetic radiation to and from the substrate with the sample present, t' (t-prime)
1305—subtracting t" from t' to determine the transmission time difference with the sample present and without the sample present, Δt
1306—measuring the travel time of the terahertz electromagnetic radiation to and from the sample, $2t_1$
1307—determining the time difference between the FS echo and the BS echo, 2τ
1308—subtracting Δt from 2τ to obtain a subtraction result
1309—dividing the subtraction result by 2 to obtain a quotient
1310—multiplying the quotient by, c, to obtain the thickness of the sample
1312—evaluating, in a plurality of locations, the sample for thickness variations; and mapping the thickness variations by location
1400—schematic diagram of a process for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample under test, the sample residing on the substrate
1401—emitting terahertz electromagnetic radiation from the source
1402—measuring the travel time of the terahertz electromagnetic radiation to and from the substrate with the sample present, t' (t-prime)

1403—placing the sample on the substrate
1404—measuring the travel time of the terahertz electromagnetic radiation to and from the substrate without the sample present, t" (t-double prime)
1405—subtracting t" from t' to determine the transmission time difference with the sample present and without the sample present, Δt
1406—measuring the travel time of the terahertz electromagnetic radiation to and from the sample, $2t_1$
1407—determining the time difference between the FS echo and the BS echo, 2τ 1408—dividing Δt by 2τ and determining the quotient
1409—subtracting the quotient from 1 to obtain a factor
1410—multiplying the factor to determine the velocity of the terahertz electromagnetic radiation in the sample
1412—subtracting Δt from 2τ to obtain a subtraction result
1413—dividing the subtraction result by 2 to obtain a quotient
1414—multiplying the quotient by, c, to obtain the thickness of the sample
1416—evaluating, in a plurality of locations, the sample for microstructural variations and for thickness variations, and mapping the microstructural and thickness variations by location.
1500—fused waveform from a "fused" data file produced by merging the FS, BS, and M" scan data sets for a set of foam blocks
1600—another process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the substrate and propagated at the speed of light, c, in a medium located between the source and the substrate.
1601—merging the FS, BS, and M" scan data sets into a fused data file.
1602—producing a "fused" waveform 1602.
1603—calculating time delays between echos.
1604—determining precision thickness-independent velocity images that map microstructure.
1605—determining precision microstructure-independent thickness images that map thickness.
1606—calculating the time delays and determining precision thickness and microstructure are performed by the step of cross-correlating entire waveforms FS, BS and M".
1607—calculating the time delays and determining precision thickness and microstructure are performed by precisely identifying peaks of FS, BS and M" signals.
1608—gating and processing the FS signal prior to merging the data into a fused data file to account for low FS signal (if needed)
1609—amplifying the processed FS signal prior to merging the data into a fused data file to account for FS signal (if needed)
1610—applying a dielectric sheet on the front surface, followed by processing and gating the FS signal prior to merging the data into a fused data file to account for low FS signal (if needed)
1700—schematic of exemplary computer implemented process
1701—emitting and scanning terahertz electromagnetic radiation from the source, the terahertz radiation applied to a plurality of scan points arranged according to x and y coordinates of the sample, the plurality of scan points includes an area at least as large as the surface of the sample
1702—recording and storing in a substrate echo waveform data set file, on a scan point by scan point basis, the substrate echo (M") waveform of the terahertz electromagnetic radiation received from the substrate without the sample present;
1703—placing the sample on the substrate
1704—recording and storing in a back surface echo waveform data set file, on a scan point by scan point basis, the back surface echo (BS) waveform of the terahertz electromagnetic radiation received from the substrate with the sample present
1705—recording and storing in a front surface echo waveform data set file, on a scan point by scan point basis, the front surface echo (FS) waveform of the terahertz electromagnetic radiation received from the front surface (FS) of the sample;
1706—recalling the stored substrate echo (M") waveform data set file, recalling the stored back surface echo (BS) waveform data set file, and recalling the stored front surface echo (FS) waveform data set file
1707—opening and viewing, interactively and selectively, the substrate echo (M") waveform, the front surface echo (FS) waveform, and the back surface echo (BS) waveform, for a single scan point, the substrate echo (M") waveform, the front surface echo (FS) waveform, and the back surface echo (BS) waveform being superimposed in a display indicating amplitude and time base of the waveform
1708—viewing, interactively and selectively, an algorithm generated display of all scan points and associated substrate (M") waveforms, associated front surface (FS) waveforms and associated back surface echo (BS) waveforms, for selected scan points of the sample arranged according to x and y scan coordinates
1709—gating, interactively, the front surface echo (FS) waveform and the substrate echo (M") waveform based on ranges determined from viewing selected scan points of the sample, the gating filters the scan points having waveforms beyond the time width of the gates;
1710—conditioning, the front surface echo (FS) waveform
1710A—optionally conditioning the front surface (FS) echo waveform includes processes selected from the group of wavelet denoising, wavelet reconstruction, and filtering
1711—fusing the stored substrate echo (M") waveform data set file and the stored front surface echo (FS) waveform data set file into the stored back surface echo (BS) waveform data set file and producing a fused data file for each of the scan points;
1712—viewing and displaying the fused substrate (M") waveforms, front surface (FS) waveforms and associated back surface echo (BS) waveforms, interactively and selectively, selected x and y scan coordinates, according to an algorithm generated display of all scan points;
1713—selecting one of the fused data files, and interactively gating the front surface (FS) echo waveform and interactively gating the back surface (BS) echo waveform based on ranges determined from viewing the selected fused waveforms;
1714—calculating the difference in time, 2τ, between the front surface (FS) echo waveforms and the back surface (BS) echo waveforms on a scan point by scan point basis generating and storing a 2τ file;
1714A—calculating the difference in time, 2τ, between the front surface (FS) echo waveforms and the back surface (BS) echo waveforms on a scan point by scan point basis generating and storing a 2τ file is performed according to the algorithm by cross-correlating the waveforms on a scan point by scan point basis 1714B—optionally calculating the difference in time, 2τ, between the front surface (FS) echo waveforms and the back surface (BS) echo waveforms on a scan point by scan point basis generating and storing a 2τ file is performed according the algorithm by comparing the peaks of the waveforms on a scan point by scan point basis 1715—interactively gating the back surface (BS) echo waveform and interactively gating the substrate (M") echo waveform of the selected fused waveform file based on ranges determined from viewing the selected fused waveforms;

1716—calculating according to the algorithm the difference in time, Δt, between the front surface (BS) echo waveforms and the substrate (M") echo waveforms on a scan point by scan point basis generating and storing a Δt file 1716A—optionally calculating according to the algorithm the difference in time, Δt, between the front surface (BS) echo waveforms and the substrate (M") echo waveforms on a scan point by scan point basis generating and storing a Δt file is performed according to the algorithm by cross-correlating the waveforms on a scan point by scan point basis 1716B—optionally calculating according to the algorithm the difference in time, Δt, between the front surface (BS) echo waveforms and the substrate (M") echo waveforms on a scan point by scan point basis generating and storing a Δt file is performed according to the algorithm by comparing the peaks of the waveforms on a scan point by scan point basis 1717—determining according to the algorithm and storing, on a scan point by scan point basis, the velocity of terahertz electromagnetic radiation in the sample without prior knowledge of the thickness of the sample 1717A—displaying, on a scan point by scan point basis, the velocity of terahertz electromagnetic radiation in the sample without prior knowledge of the thickness of the sample 1717B—calculating, on a scan point by scan point basis, the density of in the sample without prior knowledge of the thickness of the sample 1717C—determining and storing according to an algorithm, on a scan point by scan point basis, the velocity of terahertz electromagnetic radiation in the sample without prior knowledge of the thickness, according to the algorithm implementing the equation: $V=c(1-\Delta t/2\tau)$ 1718—determining according to the algorithm and storing, on a scan point by scan point basis, the thickness of the sample without prior knowledge of the velocity of the terahertz electromagnetic radiation in the sample 1718A—displaying, on a scan point by scan point basis, the thickness of the sample without prior knowledge of the velocity of the terahertz electromagnetic radiation in the sample 1718B—step of determining according to the algorithm and storing, on a scan point by scan point basis, the thickness of the sample without prior knowledge of the velocity of the terahertz electromagnetic radiation in the sample, is performed according to the algorithm implementing the equation: $d=c(2\tau-\Delta t)/2$ 1790—step of fusing in the exemplary processes of FIGS. 17 and 18 includes doubling the time base of the fused data waveform.

1791—steps of gating and conditioning the substrate echo (M") and the front surface (FS) echo waveforms in the exemplary process of FIGS. 17 and 18 include the step of delaying the substrate echo in time to better gate the substrate echo and then remove the delay when the step of fusing the substrate echo (M") waveform and the front side echo (FS) waveform into the back side echo waveform (BS) is performed.

1800—schematic of exemplary computer implemented process

1801—emitting and scanning terahertz electromagnetic radiation from the source, the terahertz radiation applied to a plurality of scan points arranged according to x and y coordinates of the scanning, the plurality of scan points includes an area at least as large as the surface of the sample, 1801.

1802—recording and storing in a substrate echo waveform data set file, on a scan point by scan point basis, a substrate echo (M") waveform of the terahertz electromagnetic radiation received from the substrate without the sample present, and recording and storing front surface (FS) waveform and back surface (BS) waveform of the terahertz electromagnetic radiation received with the sample present 1803—superimposing the substrate echo (M") waveform, the front surface (FS) echo waveform, and the back surface (BS) echo waveform together 1804—fusing the substrate echo (M") waveform and the front surface echo (FS) waveform into the back surface (BS) echo waveform 1805—gating the echo waveforms and determine the time difference between the front surface echo (FS) waveform and the back surface (BS) echo waveform, 2τ, and storing values of 2τ for each scan point 1806—interactively gating the echo waveforms and determining the time difference between the substrate echo wave (M") waveform and the back surface (BS) waveform, Δt, and storing values of Δt for each scan point 1807—using the stored values of 2τ and Δt in accordance with the algorithm to determine the velocity of the terahertz electromagnetic radiation in the sample on a scan point by scan point basis is performed 1808—determining and storing, on a scan point by scan point basis, the velocity, V, of terahertz electromagnetic radiation in the sample without prior knowledge of the thickness, velocity, V, is determined by solving the equation, $V=c(1-\Delta t/2\tau)$, for each the scan point and storing the determined velocity value in a velocity computer file on a scan point by scan point basis 1809—using the stored values of 2τ and Δt in the algorithm to determine the thickness of the sample on a scan point by scan point basis in accordance with the algorithm to determine on a scan point by scan point basis, the thickness, d, of the sample without prior knowledge of the velocity of the terahertz electromagnetic radiation in the sample, thickness is determined by solving the equation, $d=c(2\tau-\Delta t)/2$, for each the scan point and storing the thickness value in a thickness computer file 1900—schematic of exemplary computer implemented process 1901—emitting and scanning terahertz electromagnetic radiation from said source, the terahertz radiation applied to a plurality of scan points arranged according to x and y coordinates of the source, the plurality of scan points includes an area at least as large as the surface of the sample 1902—forming a substrate (M") echo waveform files for each scan point 1903—forming a front surface (FS) echo waveform file and a back surface (BS) echo waveform file for each scan point 1904—superimposing, using a graphical user interface, said front surface (FS) echo waveform files, the back surface (BS) echo waveform files and the substrate echo (M") waveform for each scan point

1905—outputting and displaying an amplitude based image of one of the superimposed files for inspection of the superimposed files

1906—inspecting said superimposed files and selecting one of said superimposed files for gating

1907—gating, using a graphical user interface, the front surface (FS) echo waveform and the substrate echo (M") waveform and fusing said front surface (FS) echo waveform and the substrate echo (M") waveform into the back surface (BS) echo waveform on a scan point by scan point basis and outputting an image of said fused waveforms

1908—selecting, using a graphical user interface, one of said fused waveforms and gating said waveform for determining $2\tau$ and $\Delta t$ on a scan point by scan point basis

1909—determining and storing, based on $2\tau$ and $\Delta t$, on a scan point by scan point basis, the velocity of terahertz electromagnetic radiation in the sample without prior knowledge of the thickness of the sample is performed and determining and storing, based on $2\tau$ and $\Delta t$, on a scan point by scan point basis, the thickness of the sample without prior knowledge of the velocity of the terahertz electromagnetic radiation in the sample

2000—oscilloscope-like trace of a front surface (FS) echo waveform and a back surface (BS) echo waveform for the x=86, y-84 scan point coordinate

2000A—oscilloscope-like trace of a substrate echo (M") waveform for the x=86, y-84 scan point coordinate

2000B—oscilloscope-like trace of the front surface (FS) echo waveform and the substrate echo (M") waveform superimposed into the back surface (BS) echo waveform for the x=86, y-84 scan point coordinate

2000C—image of the back surface (BS) echo waveform illustrating the x-y scan points ranging from x=171 to y=171 allowing the user to canvas any of the scan points to produce superimposed files having the front surface (FS) echo waveform, the substrate echo (M") waveform superimposed into and onto the back surface (BS) echo waveform

2000D—image of the superimposed file for scan coordinates of x=20, y=150 and the corresponding oscilloscope-like trace of the superimposed files having the front surface (FS) echo waveform, the substrate echo (M") waveform superimposed into and onto the back surface (BS) echo waveform

2000E—image of the superimposed file for scan coordinates of x=86, y=84 and the corresponding oscilloscope-like trace of the superimposed files having the front surface (FS) echo waveform, the substrate echo (M") waveform superimposed into and onto the back surface (BS) echo waveform

2000F—image of the superimposed file for scan coordinates of x=150, y=20 and the corresponding oscilloscope-like trace of the superimposed files having the front surface (FS) echo waveform, the substrate echo (M") waveform superimposed into and onto the back surface (BS) echo waveform

2000G—screen shot from the software program implementing signal condition of the front surface (FS) echo waveform and delaying, by a specified amount of time, the substrate echo (M") waveform to facilitate gating of the substrate echo (M") waveform

2000F—oscilloscope-like trace of the time shifted substrate echo (M") waveform and gating of the front surface (FS) echo waveform and the time shifted substrate (M") waveform

2000I—screen shot similar to FIG. 20G from the software program implementing signal condition of the front surface (FS) echo waveform and delaying, by a specified amount of time, the substrate echo (M") waveform to facilitate gating of the substrate echo (M") waveform and in addition indicating the "fuse gated waves" boolean button

2000J—oscilloscope-like trace of the fused waveform containing the front surface (FS) echo, the substrate echo (M") and the back surface (BS) echo

2000K—oscilloscope-like trace of the fused waveform containing the front surface (FS) echo, the substrate echo (M") and the back surface (BS) echo of FIG. 20J illustrating gates placed over the front surface (FS) echo and the back surface (BS) echo

2000L—oscilloscope-like trace of the fused waveform containing the front surface (FS) echo, the substrate echo (M") and the back surface (BS) echo of FIG. 20J illustrating gates placed over the substrate echo (M") and the back surface (BS) echo.

2000M—computer generated image of the thickness-independent velocity image generated by the computer program.

2000N—computer generated image of the density image corresponding to the velocity image of FIG. 2000M.

2001—back surface (BS) echo waveform for the x=86, y=84 scan point coordinate

2002—front surface (FS) echo waveform for the x=86, y=84 scan point coordinate

2003—substrate echo (M") waveform for the x=86, y=84 scan point coordinate

2003—time shifted substrate echo (M") waveform

2004—x=86 scan coordinate

2005—y=84 scan coordinate

2006—cursor location/red circle

2007—gray scale amplitude meter

2008—cursor location x=20, y=150

2009—cursor location x=86, y=84

2010—cursor location x=150, y=20

2011—time shift input dialog box

2012—front surface (FS) echo waveform gate

2013—substrate echo (M") waveform gate

2014—boolean buttons for front surface (FS) echo waveform signal condition selectable options

2015—boolean button for fusing gated waves

2016—fused waveform comprising front surface (FS) echo waveforms, substrate echo (M") waveforms, and back surface (BS) echo waveforms

2017—gate over the front surface (FS) echo waveform of the fused wavetrain

2018—gate over the back surface (BS) echo waveform of the fused wavetrain

2019—gate over the substrate echo (M") echo waveform of the fused wavetrain

2020—gate over the back surface (BS) echo waveform of the fused wavetrain

2021—velocity amplitude gray scale indicator

2022—cursor position of the velocity image

2023—density amplitude gray scale indicator

2024—cursor position of the density image

2025—check box for converting velocity image to a density image

2100—is a screen shot of the program illustrating a histogram of the density plot and a density image after the outliers have been removed.

2101—minimum value of acceptable density data points

2102—maximum value of acceptable density data points

2103—outliers

2104—remove outlier button
2105—true density image
BS—pulse that travels from the transceiver to the reflector plate and back to the transceiver with the sample present
FS—pulse that travels from the transceiver to the front surface of the sample and back to the transceiver
L—distance between transceiver and sample
M"—pulse that travels from the transceiver to the reflector plate and back to the transceiver without the sample present
c—speed of light in a medium located between the source of the terahertz radiation and the substrate
d—sample thickness
t' (t-prime)—travel time of the terahertz electromagnetic radiation to and from the substrate with the sample present;
t" (t-double prime)—travel time of the terahertz electromagnetic radiation to and from the substrate without the sample present;
$\Delta t$—transmission time difference (t' minus t") with the sample present and without the sample present;
$2t_1$—measuring the travel time of the terahertz electromagnetic radiation to and from the sample;
$2\tau$—time difference between the FS echo and the BS echo, $2\tau$
V—velocity Those skilled in the art will readily recognize that the invention has been set forth by way of example only. Accordingly, those skilled in the art will recognize that changes may be made to the invention without departing from the spirit and scope of the attached claims.

The invention claimed is:

1. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, a transceiver, and said sample, comprising the steps of:

emitting and scanning terahertz electromagnetic radiation from said source, namely, said transceiver, said terahertz radiation applied to a plurality of scan points arranged according to x and y coordinates of said sample, said plurality of scan points includes an area at least as large as said surface of said sample;

recording and storing in a substrate echo waveform data set file, on a scan point by scan point basis, said substrate echo (M") waveform of said terahertz electromagnetic radiation received from said substrate without said sample present;

placing said sample on said substrate;

recording and storing in a back surface echo waveform data set file, on a scan point by scan point basis, the back surface echo (BS) waveform of said terahertz electromagnetic radiation received from said substrate with said sample present;

recording and storing in a front surface echo waveform data set file, on a scan point by scan point basis, the front surface echo (FS) waveform of said terahertz electromagnetic radiation received from said front surface (FS) of said sample;

recalling said stored substrate echo (M") waveform data set file, recalling said stored back surface echo (BS) waveform data set file, and recalling said stored front surface echo (FS) waveform data set file;

opening and viewing, interactively and selectively, said substrate echo (M") waveform, said front surface echo (FS) waveform, and said back surface echo (BS) waveform, for a single scan point, said substrate echo (M") waveform, said front surface echo (FS) waveform, and said back surface echo (BS) waveform being superimposed in a display indicating amplitude and time base of said waveform;

viewing, interactively and selectively, an algorithm generated display of all scan points and associated substrate (M") waveforms, associated front surface (FS) waveforms and associated back surface echo (BS) waveforms, for selected scan points of said sample arranged according to x and y scan coordinates;

gating, interactively, said front surface echo (FS) waveform and said substrate echo (M") waveform based on ranges determined from viewing selected scan points of said sample, said gating filters said scan points having waveforms beyond the time width of said gates;

conditioning, said front surface echo (FS) waveform;

fusing said stored substrate echo (M") waveform data set file and said stored front surface echo (FS) waveform data set file into said stored back surface echo (BS) waveform data set file and producing a fused data file for each of said scan points;

viewing and displaying said fused substrate (M") waveforms, front surface (FS) waveforms and associated back surface echo (BS) waveforms, interactively and selectively, for selected x and y scan coordinates, according to an algorithm generated display of all scan points;

selecting one of said fused data files, and interactively gating said front surface (FS) echo waveform and interactively gating said back surface (BS) echo waveform of one said selected fused waveform file based on ranges determined from viewing said previously fused waveforms;

calculating the difference in time, $2\tau$, between said front surface (FS) echo waveforms and said back surface (BS) echo waveforms on a scan point by scan point basis generating and storing a $2\tau$ file;

interactively gating said back surface (BS) echo waveform and interactively gating said substrate (M") echo waveform of said selected fused waveform file based on ranges determined from viewing said selected fused waveforms;

calculating according to said algorithm the difference in time, $\Delta t$, between said front surface (BS) echo waveforms and said substrate (M") echo waveforms on a scan point by scan point basis generating and storing a $\Delta t$ file;

determining according to said algorithm and storing, on a scan point by scan point basis, the velocity of terahertz electromagnetic radiation in said sample without prior knowledge of the thickness of said sample; and, determining according to said algorithm and storing, on a scan point by scan point basis, said thickness of said sample without prior knowledge of said velocity of said terahertz electromagnetic radiation in said sample.

2. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 1, further comprising the steps of:

displaying, on a scan point by scan point basis, said velocity of terahertz electromagnetic radiation in said sample without prior knowledge of the thickness of said sample; and, displaying, on a scan point by scan point basis, said thickness of said sample without prior knowledge of said velocity of said terahertz electromagnetic radiation in said sample.

3. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 1, further comprising the steps of:

calculating, on a scan point by scan point basis, the density of terahertz electromagnetic radiation in said sample without prior knowledge of the thickness of said sample.

4. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 3, further comprising the steps of:

displaying, on a scan point by scan point basis, the density of terahertz electromagnetic radiation in said sample without prior knowledge of the thickness of said sample.

5. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 1, wherein the step of conditioning said front surface (FS) echo waveform includes processes selected from the group of wavelet denoising, wavelet reconstruction, and filtering.

6. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 1, wherein the step of determining and storing according to an algorithm, on a scan point by scan point basis, the velocity of terahertz electromagnetic radiation in said sample without prior knowledge of said thickness, is performed according to said algorithm solving for V using the equation: $V=c(1-\Delta t/2\tau)$ and the step of determining according to said algorithm and storing, on a scan point by scan point basis, said thickness of said sample without prior knowledge of said velocity of said terahertz electromagnetic radiation in said sample, is performed according to said algorithm solving for d using the equation: $d=c(2\tau-\Delta t)/2$.

7. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 1, wherein the step of calculating the difference in time, $2\tau$, between said front surface (FS) echo waveforms and said back surface (BS) echo waveforms on a scan point by scan point basis generating and storing a $2\tau$ file and the step of calculating according to said algorithm the difference in time, $\Delta t$, between said front surface (BS) echo waveforms and said substrate (M") echo waveforms on a scan point by scan point basis generating and storing a $\Delta t$ file is performed according to said algorithm by cross-correlating said waveforms on a scan point by scan point basis.

8. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 1, wherein the step of calculating the difference in time, $2\tau$, between said front surface (FS) echo waveforms and said back surface (BS) echo waveforms on a scan point by scan point basis generating and storing a $2\tau$ file and the step of calculating according to said algorithm the difference in time, $\Delta t$, between said front surface (BS) echo waveforms and said substrate (M") echo waveforms on a scan point by scan point basis generating and storing a $\Delta t$ file is performed by comparing the peaks of said waveforms on a scan point by scan point basis.

9. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 1, comprising the steps of:
wherein said step of fusing on a point by point basis includes fusing said gated substrate echo surface (M") waveform and said gated front surface echo (FS) waveform into said back surface echo (BS) waveform and doubling the time base of said fused data waveform.

10. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample, comprising the steps of:
emitting and scanning terahertz electromagnetic radiation from said source, namely, said transceiver, said terahertz radiation applied to a plurality of scan points arranged according to x and y coordinates of said source, namely, said transceiver, said plurality of scan points includes an area at least as large as said surface of said sample;
forming a substrate (M") echo waveform file for each scan point;
placing said sample on said substrate;
forming a front surface (FS) echo waveform file and a back surface (BS) echo waveform file for each scan point;
superimposing, using a graphical user interface, said front surface (FS) echo waveform files, said back surface (BS) echo waveform files and said substrate echo (M") waveform for each scan point;
outputting and displaying an image of one of said back surface (BS) echo files for inspection of said superimposed files;
interactively, through a graphical user interface, inspecting said superimposed files; and selecting one of said superimposed files for gating;
gating, using a graphical user interface, said front surface (FS) echo waveform and said substrate echo (M") waveform and fusing said front surface (FS) echo waveform and said substrate echo (M") waveform into said back surface (BS) echo waveform on a scan point by scan point basis and outputting an image of said fused waveforms;
selecting, using a graphical user interface, one of said fused waveforms and gating said waveform for determining $2\tau$ and $\Delta t$ on a scan point by scan point basis;
determining and storing, based on $2\tau$ and $\Delta t$, on a scan point by scan point basis, the velocity of terahertz electromagnetic radiation in said sample without prior knowledge of the thickness of said sample; and,
determining and storing, based on $2\tau$ and $\Delta t$, on a scan point by scan point basis, said thickness of said sample without prior knowledge of said velocity of said terahertz electromagnetic radiation in said sample.

11. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 10, further comprising the steps of:
displaying, on a scan point by scan point basis, the velocity of terahertz electromagnetic radiation in said sample without prior knowledge of the thickness of said sample; and,
displaying, on a scan point by scan point basis, said thickness of said sample without prior knowledge of said velocity of said terahertz electromagnetic radiation in said sample.

12. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 10, further comprising the steps of:
calculating, on a scan point by scan point basis, the density of terahertz electromagnetic radiation in said sample without prior knowledge of the thickness of said sample.

13. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 12, further comprising the steps of:
displaying, on a scan point by scan point basis, the density of terahertz electromagnetic radiation in said sample without prior knowledge of the thickness of said sample.

14. A process for non-destructive evaluation of a sample using a computer, a display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample as claimed in claim 10, comprising the steps of:
wherein said step of fusing on a point by point basis includes fusing said gated substrate echo surface (M") waveform and said gated front surface echo (FS) waveform into said back surface echo (BS) waveform and doubling the time base of said fused data waveform.

15. A process for non-destructive evaluation of a sample using a computer, a computer display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source, namely, said transceiver, spaced apart from said sample under test and propagated at the speed of light, c, in a medium located between said source, namely, said transceiver, and said sample, comprising the steps of:

emitting and scanning terahertz electromagnetic radiation from said source, namely, said transceiver, said terahertz radiation applied to a plurality of scan points arranged according to x and y coordinates of said source, namely, said transceiver, said plurality of scan points includes an area at least as large as said surface of said sample;

recording and storing in a substrate echo waveform data set file, on a scan point by scan point basis, said substrate echo (M") waveform of said terahertz electromagnetic radiation received from said substrate without said sample present;

placing said sample on said substrate;

recording and storing in a back surface echo waveform data set file, on a scan point by scan point basis, the back surface echo (BS) waveform of said terahertz electromagnetic radiation received from said substrate with said sample present;

recording and storing in a front surface echo waveform data set file, on a scan point by scan point basis, the front surface echo (FS) waveform of said terahertz electromagnetic radiation received from said front surface (FS) of the sample;

selecting and superimposing, according to said algorithm, said front surface (FS) echo waveform of said selected scan point, said back surface (BS) echo waveform of said selected scan point, and said substrate echo (M") waveform of said selected scan point;

gating, interactively, and fusing according to said algorithm said substrate echo (M") and said front surface (FS) echo waveform forming a fused waveform on a scan point by scan point basis;

selecting, interactively, one of said fused waveforms and gating said waveform for determining $2\tau$ and $\Delta t$ on a scan point by scan point basis;

determining, storing, and displaying, based on $2\tau$ and $\Delta t$, on a scan point by scan point basis, the velocity of terahertz electromagnetic radiation in said sample without prior knowledge of the thickness of said sample, said velocity, V, determined by solving the equation, $V=c(1-\Delta t/2\tau)$; and, determining, storing, and displaying, based on $2\tau$ and $\Delta t$, on a scan point by scan point basis, said thickness of said sample without prior knowledge of said velocity of said terahertz electromagnetic radiation in said sample, said thickness, d, determined by solving the equation, $d=c(2\tau-\Delta t)/2$.

16. A process for non-destructive evaluation of a sample using a computer, a computer display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source spaced apart from said sample under test and propagated at the speed of light, c, in a medium located between said source and said sample, comprising the steps of:

emitting and scanning terahertz electromagnetic radiation from said source said terahertz radiation applied to a plurality of scan points arranged according to x and y coordinates of said scanning, said plurality of scan points includes an area at least as large as said surface of said sample;

recording and storing in a substrate echo waveform data set file, on a scan point by scan point basis, a substrate echo (M") waveform of said terahertz electromagnetic radiation received from said substrate without said sample present, and recording and storing a front surface (FS) waveform and back surface (BS) waveform of said terahertz electromagnetic radiation received with the sample present;

superimposing said substrate echo (M") waveform, said front surface (FS) echo waveform, and said back surface (BS) echo waveform together;

gating and conditioning said substrate echo (M") and said front surface (FS) echo waveform;

fusing said substrate echo (M") waveform and said front surface echo (FS) waveform into said back surface (BS) echo waveform;

gating said echo waveforms and determining said time difference between said front surface echo (FS) waveform and said back surface (BS) echo waveform, $2\tau$, and storing values of $2\tau$ for each scan point;

gating said echo waveforms and determining said time difference between said substrate echo wave (M") waveform and said back surface (BS) waveform, $\Delta t$, and storing values of $\Delta t$ for each scan point;

using said stored values of $2\tau$ and $\Delta t$ in said algorithm to determine the velocity of the terahertz electromagnetic radiation in said sample on a scan point by scan point basis, said algorithm includes the step of determining and storing, on a scan point by scan point basis, the velocity of terahertz electromagnetic radiation in said sample without prior knowledge of said thickness, said velocity, V, is determined by solving the equation, $V=c(1-\Delta t/2\tau)$, for each said scan point and storing said velocity value in a velocity computer file on a scan point by scan point basis;

using said stored values of $2\tau$ and $\Delta t$ in said algorithm to determine the thickness of said sample on a scan point by scan point basis, said algorithm includes the step of determining on a scan point by scan point basis, said thickness, d, of said sample without prior knowledge of said velocity of said terahertz electromagnetic radiation in said sample, is determined by solving the equation, $d=c(2\tau-\Delta t)/2$, for each said scan point and storing said thickness value in a thickness computer file.

17. A process for non-destructive evaluation of a sample using a computer, a computer display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source spaced apart from said sample under test and propagated at the speed of light, c, in a medium located between said source and said sample, as claimed in claim 16, wherein the steps of gating and conditioning said substrate echo (M") and said front surface (FS) echo waveform include delaying said substrate echo in time to better gate said substrate echo and then remove said delay when said step of fusing said substrate echo (M″) waveform and said front side echo (FS) waveform into said back side echo waveform (BS) is performed.

18. A process for non-destructive evaluation of a sample using a computer, a computer display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source spaced apart from said sample under test and propagated at the speed of light, c, in a medium located between said source and said sample, as claimed in claim 17, wherein said steps of: gating said echo waveforms and determining said time difference between said front surface echo (FS) waveform and said back surface (BS) echo waveform, $2\tau$, and storing values of $2\tau$ for each scan point; and, gating said echo waveforms and determining said time difference between said substrate echo wave (M″) waveform and said back surface (BS) waveform, $\Delta t$, and storing values of $\Delta t$ are performed by said algorithm cross-correlating said waveforms for each scan point.

19. A process for non-destructive evaluation of a sample using a computer, a computer display and a computer program implementing an algorithm, said algorithm includes determining the velocity of terahertz electromagnetic radiation in said sample without prior knowledge of the thickness of said sample and determining said thickness of said sample without prior knowledge of said velocity of said terahertz electromagnetic radiation in said sample, said terahertz electromagnetic radiation produced by a source spaced apart from said sample under test and propagated at the speed of light, c, in a medium located between said source and said sample, as claimed in claim 17, wherein said steps of: gating said echo waveforms and determining said time difference between said front surface echo (FS) waveform and said back surface (BS) echo waveform, $2\tau$, and storing values of $2\tau$ for each scan point; and, gating said echo waveforms and determining said time difference between said substrate echo wave (M″) waveform and said back surface (BS) waveform, $\Delta t$, and storing values of $\Delta t$ are performed by said algorithm by comparison of peak to peak amplitudes for each scan point.

* * * * *